US008987316B2

United States Patent
Kalbe

(10) Patent No.: US 8,987,316 B2
(45) Date of Patent: Mar. 24, 2015

(54) ISOCYANATE AND ISOTHIOCYANATE COMPOUNDS FOR CANCER TREATMENT

(71) Applicant: Jochen Kalbe, Leichlingen (DE)

(72) Inventor: Jochen Kalbe, Leichlingen (DE)

(73) Assignee: DoubleHill GmbH, Zeithain (DE)

( * ) Notice: Subject to any disclaimer, the term of this patent is extended or adjusted under 35 U.S.C. 154(b) by 0 days.

(21) Appl. No.: 14/346,744

(22) PCT Filed: Sep. 18, 2012

(86) PCT No.: PCT/EP2012/003887
§ 371 (c)(1),
(2) Date: Mar. 24, 2014

(87) PCT Pub. No.: WO2013/041204
PCT Pub. Date: Mar. 28, 2013

(65) Prior Publication Data
US 2014/0228419 A1    Aug. 14, 2014

(30) Foreign Application Priority Data

Sep. 23, 2011    (EP) .................................... 11007772

(51) Int. Cl.
C07C 265/12    (2006.01)
C07C 331/28    (2006.01)
C07C 309/15    (2006.01)
C07D 233/64    (2006.01)

(52) U.S. Cl.
CPC ............ *C07D 233/64* (2013.01); *C07C 265/12* (2013.01); *C07C 331/28* (2013.01); *C07C 309/15* (2013.01)

USPC .......... 514/400; 514/514; 548/340.1; 558/17; 560/358

(58) Field of Classification Search
None
See application file for complete search history.

(56) References Cited

U.S. PATENT DOCUMENTS

2006/0241178 A1    10/2006    Chung

FOREIGN PATENT DOCUMENTS

EP    2248800    11/2010

OTHER PUBLICATIONS

Tohyama et al., caplus an 2001:432884.*
International Search Report for corresponding PCT/EP2012/003887 mailed Dec. 12, 2012, three pages.
International Preliminary Report on Patentability for corresponding PCT/EP2012/003887 issued Mar. 25, 2014, five pages.
Zhang, "Cancer-Preventive Isothiocyanates: Measurement of Human Exposure and Mechanism of Action", Mutation Research, Elsevier, Amsterdam, NL, vol. 555, No. 1-2, Nov. 2, 2004, 19 pages.

* cited by examiner

Primary Examiner — Sun Jae Yoo
(74) Attorney, Agent, or Firm — Rankin, Hill & Clark LLP

(57) ABSTRACT

The present invention relates to novel isocyanate and isothiocyanate compounds, to pharmaceutical compositions comprising them, and to the use thereof in the treatment of cancer diseases in humans and animals. The novel isocyanate and isothiocyanate compounds are distinguished, as compared with the known isocyanate and isothiocyanate compounds, by improved therapeutical breadth, i.e. fewer side effects while having high anti-tumor activity.

18 Claims, 4 Drawing Sheets

Selectivity of the anti-tumor activity of the compound of Example 2a (sodium salt) on different tumors Dose-dependent anti-tumor activity of the compound of Example 2a (sodium salt) in breast tumors (MAXF 401 – Xenograft in nude mice–treatment 2 x / week (ip-injection)

Dose-dependent anti-tumor activity of the compound of Example 2a (sodium salt) in a colon carcinoma Xenograft model (CXF 280 – treatment 2 x / week (ip-injection)

1H-NMR spectrum (400 MHz) of the compound of Example 2a.

ISOCYANATE AND ISOTHIOCYANATE COMPOUNDS FOR CANCER TREATMENT

The present invention relates to novel isocyanate and isothiocyanate compounds, to pharmaceutical compositions comprising them, and to the use thereof in the treatment of cancer diseases in humans and animals. The novel isocyanate and isothiocyanate compounds are distinguished, as compared with the known isocyanate and isothiocyanate compounds, by an improved therapeutic breadth, i.e. by fewer side-effects with a high anti-tumor action.

INTRODUCTION

From the prior art various isocyanate and isothiocyanate compounds for the use in the treatment of cancer diseases are already known.

For example, US 2006/241178 describes the treatment of lung cancer by administering isothiocyanate conjugates on the basis of phenyl, benzyl and alkyl isothiocyanates as well as sulforaphane

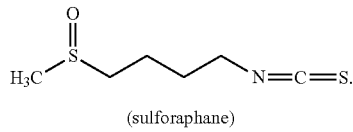

(sulforaphane)

Further, WO 1994/19948 describes the use of sulforaphane isothiocyanate compounds for the use in the treatment of cancer diseases.

From WO 2000/49013 isothiocyanate compounds with a heterocyclic 5-membered ring and their use in the treatment of cancer are known.

The object of WO 2008/008954 are further various isothiocyanate compounds, particularly isothiocyanate glucosinolates for the use in the treatment of cancer diseases.

Further, WO 2009/089889 describes the cytotoxic activity of glucomoringin:

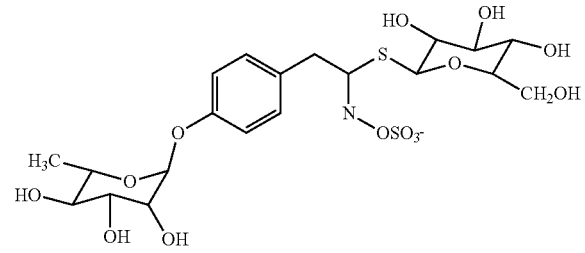

Isothiocyanate compounds of the formula SCN—R—X—R—NCS and their anti-carcinogenic activity are further described in WO 2008/082692.

US 2010/0312000 further relates to novel isothiocyanate compounds with a carboxylate group $(SCN)_m$-A-B—$(CO_2H)_n$) and their use as a medicament in general.

The disadvantage of such known compounds is, particularly, the low selectivity against tumor cells and therewith the low efficacy or higher rate of side effects.

However, none of these publications discloses isocyanate or isothiocyanate compounds of the general formula (I), as it is the subject of the present invention.

Further, from WO 2009/004060 novel triazene compounds are known, wherein instead of the isocyanate or isothiocyanate group a triazene group of the general formula —N=N—$NR_1R_2$ is bound to the basic skeleton according to the general formula (I) of the present invention, as well as their use for the treatment of cancer. Any hint for the possibility to replace the triazene group against an isothiocyanate group cannot be found therein.

The disadvantage of such known triazene compounds is the fast metabolism of the triazene group and thus the faster loss of the tumor killing compound. To achieve effective blood levels herein, the active agent must be administered via an elongated time period and very high doses must be chosen. This increases the rate of side effects. In addition, the triazene group exhibits a high reactivity and reacts nonselective with various healthy and ill cell components.

OBJECT OF THE INVENTION

Accordingly, the object of the present invention was to find novel effective cytostatic compounds having reduced toxicity and improved activity, in order to make them available for therapy in humans or in animals, in particular for the therapy of cancer diseases in humans.

BRIEF DESCRIPTION OF THE DRAWINGS

FIG. 4 depicts a $^1$H-NMR spectrum (400 MHz) of the compound of Example 2a.

DESCRIPTION OF THE INVENTION

Figure 1:
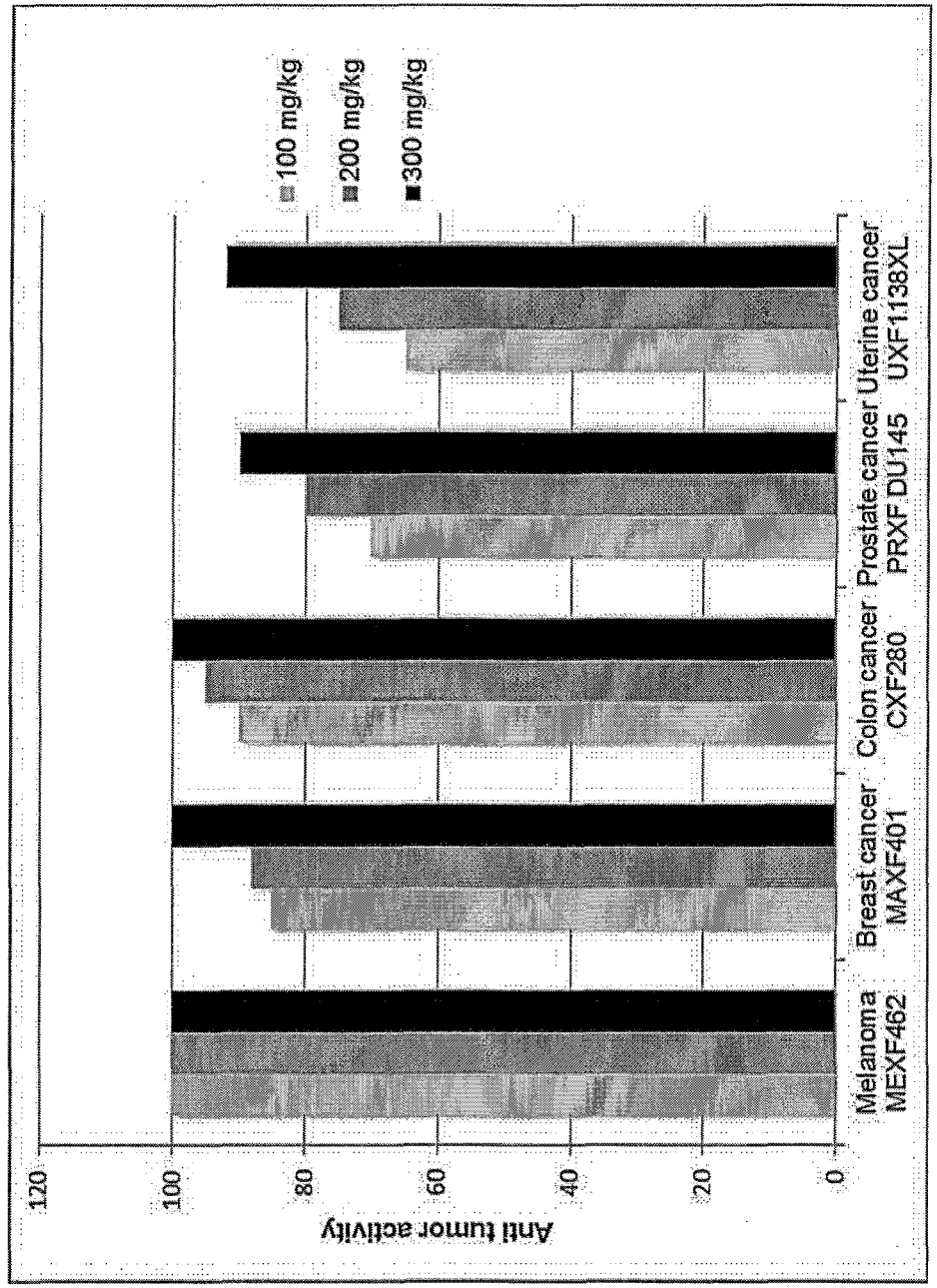
FIG. 1 depicts Selectivity of the anti-tumor activity of the compound of Example 2a (sodium salt) on different tumors.

The inventors have found novel isocyanate and isothiocyanate compounds having high cytostatic activity and the toxicity of which is markedly reduced. The invention accordingly provides compounds of formula (1):

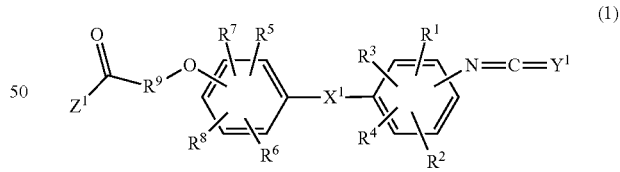

wherein
$Y^1$=S or O, and wherein
$R^1, R^2, R^3, R^4, R^5, R^6, R^7$ and $R^8$ are identical or different and are in each case selected from the group consisting of:
hydrogen,
hydroxy,
halogen,
cyano,
nitro,
carboxyl,
aminocarbonyl,
sulfonic acid radical (—$SO_3H$),
aminosulfonyl, optionally substituted alkyl,
optionally substituted alkoxy,
optionally substituted alkenyl,
optionally substituted aryl,
optionally substituted alkylaryl;

$R^9$ is optionally substituted linear, branched or cyclic alkanediyl, optionally substituted linear, branched or cyclic alkenediyl, aryl or heterocyclyl;

$Z^1$ is selected from
hydroxy (—OH) or
a radical of the formula (—$NR^{10}R^{11}$)

wherein
$R^{10}$ is hydrogen and $R^{11}$ is optionally substituted alkyl or hydroxy, or
$R^{11}$ is hydrogen and $R^{10}$ is optionally substituted alkyl or hydroxy, or
$R^{10}$ and $R^{11}$ are each alkyl, wherein at least one of the alkyl groups carries at least one substituent, or
$R^{10}$ and $R^{11}$, together with the nitrogen atom to which they are bonded, form a saturated or unsaturated, optionally substituted 5- to 8-membered ring which can optionally contain further heteroatoms; and wherein $X^1$ is selected from the group consisting of:
a single bond,
carbonyl,
sulfur,
oxygen,
sulfoxy,
sulfonyl,
azo and
an optionally substituted, saturated or unsaturated aliphatic radical having from 1 to 6 carbon atoms,
or pharmaceutically acceptable salts thereof.

Within the scope of the invention as a whole, i.e. also in connection with the other groups of substituents (wherein further possibilities can be included where indicated, as in the case of $R^{10}$ and $R^{11}$), optionally substituted alkyl preferably includes:

Linear or branched alkyl having from 1 to 8, preferably from 1 to 6, carbon atoms, cycloalkyl having from 3 to 8, preferably 5 or 6, carbon atoms, or alkyl having from 1 to 4 carbon atoms which is substituted by cycloalkyl, which in each case can optionally carry preferably from 1 to 3 substituents which are preferably selected from the group consisting of: hydroxy, halogen and cyano. Here and within the scope of the present invention, halogen includes fluorine, chlorine, bromine and iodine, preferably fluorine or chlorine. Furthermore, one or more, more preferably from 1 to 3, carbon atoms can be replaced by heteroanalogous groups containing nitrogen, oxygen or sulfur. This means in particular that, for example, one or more methylene groups in the alkyl radicals can be replaced by NH, O or S.

Examples of alkyl radicals having from 1 to 8 carbon atoms include: a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propylbutyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 5-ethylhexyl group, a 1,1-dimethylhexyl group, a 2,2-dimethylhexyl group, a 3,3-dimethylhexyl group, a 4,4-dimethylhexyl group, a 5,5-dimethylhexyl group, a 1-propylpentyl group, a 2-propylpentyl group, etc. Preference is given to those having from 1 to 6 carbon atoms, in particular methyl, ethyl and n-propyl. Methyl is most preferred.

Examples of alkyl groups which are formed by replacement with one or more heteroanalogous groups, such as —O—, —S— or —NH—, are preferably those in which one or more methylene groups have been replaced by —O— to form an ether group, such as methoxymethyl, ethoxymethyl, 2-methoxyethylene, etc. According to the invention, polyether groups are also included in the definition of alkyl.

Cycloalkyl radicals having from 3 to 8 carbon atoms preferably include: a cyclopropyl group, a cyclobutyl group, a cyclopentyl group, a cyclohexyl group, a cycloheptyl group, a cyclooctyl group, etc. Preference is given to a cyclopropyl group, a cyclobutyl group, a cyclopentyl group and a cyclohexyl group. Heterocyclic alkyl radicals which are formed from cycloalkyl by replacement of methylene by heteroanalogous groups are, for example, 5- or 6-membered heterocyclic radicals, such as tetrahydrofuryl, pyrrolidinyl, piperidinyl or tetrahydropyranyl, which can optionally be fused with aromatic rings, etc.

Examples of a halo-substituted linear or branched alkyl radical having from 1 to 8 carbon atoms include in particular: a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a 1-fluoroethyl group, a 1-chloroethyl group, a 1-bromoethyl group, a 2-fluoroethyl group, a 2-chloroethyl group, a 2-bromoethyl group, a 1,2-difluoroethyl group, a 1,2-dichloroethyl group, a 1,2-dibromoethyl group, a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4,4,4-trifluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 5-bromopentyl group, a perfluoropentyl group, a 2-fluorohexyl group, a 2-chlorohexyl group, a 2-bromohexyl group, a 6-fluorohexyl group, a 6-chlorohexyl group, a 6-bromohexyl group, a perfluorohexyl group, a 2-fluoroheptyl group, a 2-chloroheptyl group, a 2-bromoheptyl group, a 7-fluoroheptyl group, a 7-chloroheptyl group, a 7-bromoheptyl group, a perfluoroheptyl group, etc.

Examples of a hydroxy-substituted alkyl radical include the above-mentioned alkyl radicals having from 1 to 3 hydroxy radicals, such as, for example, hydroxymethyl, 2-hydroxyethyl, 3-hydroxypropyl, etc.

Within the scope of the invention as a whole, optionally substituted alkenyl preferably includes:

Linear or branched alkenyl having from 2 to 8 carbon atoms and cycloalkenyl having from 3 to 8 carbon atoms, which can optionally be substituted by preferably from 1 to 3 substituents, such as hydroxy, halogen or alkoxy. Examples include: vinyl, 1-methylvinyl, allyl, 1-butenyl, isopropenyl, cyclopropenyl, cyclobutenyl, cyclopentenyl, cyclohexenyl. Vinyl or allyl are preferred.

Within the scope of the invention as a whole, optionally substituted aryl preferably includes:

Aromatic hydrocarbon radicals having from 6 to 14 carbon atoms (wherein the carbon atoms of the substituents are not included) and 5- to 10-membered aromatic heterocyclic radicals having up to 3 heteroatoms from the group S, O, N, which can be mono- or bi-cyclic and which can be substituted by preferably from 1 to 3 substituents selected from hydroxy, halogen, cyano, alkyl, acyl and alkoxy. With regard to the definition of alkyl and halogen, reference may be made to the definitions and examples hereinbefore.

Here and in the following, alkoxy as a substituent of aryl includes, for example: An alkyl radical mentioned hereinbefore which is bonded to aryl via an oxygen atom, such as a linear or branched alkoxy radical having up to 6 carbon atoms, such as a methoxy group, an ethoxy group, an n-propoxy group, an isopropoxy group, an n-butoxy group, an isobutoxy group, a sec-butoxy group, a tert-butoxy group, an n-pentoxy group, an isopentoxy group, a sec-pentoxy group, a tert-pentoxy group, a 2-methylbutoxy group, an n-hexyloxy group, an isohexyloxy group, a tert-hexyloxy group, a sec-hexyloxy group, a 2-methylpentoxy group, a 3-methylpentoxy group, a 1-ethylbutoxy group, a 2-ethylbutoxy group, a 1,1-dimethylbutoxy group, a 2,2-dimethylbutoxy group, a 3,3-dimethylbutoxy group, a 1-ethyl-1-methylpropoxy group, etc. Preference is given to a methoxy group, an ethoxy group, an n-propoxy group, an isopropoxy group, an n-butoxy group, an isobutoxy group, a sec-butoxy group, a tert-butoxy group, etc.

Here and in the following, acyl as a substituent of aryl includes: aliphatic acyl, aromatic acyl, such as C1 to C6 alkanoyl, such as formyl, acetyl, propionyl, butyryl, isobutyryl, valeryl, isovaleryl, pivaloyl, hexanoyl, etc., and also C6 to C10 aroyl, such as benzoyl, toluolyl, xyloyl, etc.

Aromatic hydrocarbon radicals having from 6 to 14 carbon atoms include, for example: phenyl, naphthyl, phenanthrenyl and anthracenyl, which can optionally be substituted. Phenyl is preferred.

Heteroaromatic radicals include, for example: pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo(b)thienyl, benzo(b)furyl, indazolyl, quinolyl, isoquinolyl, naphthyridinyl, quinazolinyl. Preference is given to 5- or 6-membered aromatic heterocycles such as, for example, pyridyl, pyridyl N-oxide, pyrimidyl, pyridazinyl, furyl and thienyl.

Within the scope of the invention as a whole, optionally substituted alkylaryl preferably includes:

Linear or branched alkyl having from 1 to 8, preferably from 1 to 4, carbon atoms, as described above, which is substituted with aryl, as described above. The preferred arylalkyl is benzyl.

In addition, within the scope of the invention as a whole, aminocarbonyl is preferably carbamoyl ($H_2NCO-$) or mono or dialkylaminocarbonyl ($H(alkyl)NCO-$ or $(alkyl)_2NCO-$), wherein with regard to the definition of alkyl, reference may be made to the aforesaid explanations and further includes optionally substituted alkyl.

Furthermore, within the scope of the invention as a whole, aminosulfonyl in particularly sulfamoyl ($H_2N-SO_2-$) or mono or dialkylaminosulfonyl $(alkyl)_2N-SO_2$, wherein with regard to the definition of alkyl, reference may be made to the aforesaid explanations and further includes optionally substituted alkyl.

Optionally substituted alkoxy includes the aforesaid as a substituent of aryl exemplified alkoxy, which can optionally be substituted by preferably from 1 to 3 substituents, which are preferably selected from the group of halogen, hydroxy, and cyano.

Preferably, $R^1$, $R^2$, $R^3$, $R^4$, $R^5$, $R^6$, $R^7$ and $R^8$ are selected, from:
hydrogen,
hydroxy,
halogen,
cyano,
nitro,
carboxyl,
aminocarbonyl,
sulfonic acid ($-SO_3H$),
aminosulfonyl,
optionally substituted alkyl, and
optionally substituted alkoxy.

More preferably, $R^1$, $R^2$, $R^3$, $R^4$, $R^5$, $R^6$, $R^7$ and $R^8$ are selected from:
hydrogen,
hydroxy,
halogen, and
optionally substituted alkoxy.

Preferably at least 6, more preferably at least 7, of the radicals $R^2$, $R^3$, $R^4$, $R^5$, $R^6$, $R^7$ and $R^8$ represent hydrogen. Most preferably, all the radicals $R^1$, $R^2$, $R^3$, $R^4$, $R^5$, $R^6$, $R^7$ and $R^8$ represent hydrogen.

$R^9$ in the general formula (1) is optionally substituted linear, branched (branched-chained) or cyclic alkanediyl, optionally substituted linear, branched (branched-chained) or cyclic alkenediyl, optionally substituted aryl or optionally substituted heterocyclyl.

Optionally substituted alkanediyl is preferably a divalent linear or branched alkanediyl radical having from 1 to 7, preferably from 1 to 6, more preferably from 1 to 4, carbon atoms, which can optionally carry from 1 to 3 substituents selected from the group consisting of hydroxy, halogen and cyano. The following may be mentioned as preferred examples: methylene, 1,2-ethanediyl, ethane-1,1-diyl, 1,3-propylene, propane-1,1-diyl, propane-1,2-diyl, propane-2,2-diyl, 1,4-butylene, butane-1,2-diyl, butane-1,3-diyl, butane-2,3-diyl, pentane-1,5-diyl, pentane-2,4-diyl, 3-methylpentane-2,4-diyl and hexane-1,6-diyl. A preferred substituted alkanediyl radical is a hydroxy-substituted alkanediyl radical.

It is further preferred, that the alkanediyl radical is a cyclic alkanediyl radical having from 3 to 8, preferably 5 or 6 carbon atoms, as defined above in context with optionally substituted alkyl. With regard to the preferred cyclic alkanediyl radicals, reference can be made to the aforementioned preferred cycloalkyl radicals.

Optionally substituted alkenediyl is preferably a divalent linear or branched alkenediyl radical having from 2 to 7, more preferably from 2 to 6, still more preferably from 2 to 4, carbon atoms, which can optionally carry from 1 to 3 substituents selected from the group consisting of hydroxy, halogen and cyano. The following may be mentioned as preferred examples: ethene-1,1-diyl, ethene-1,2-diyl, propene-1,1-diyl, propene-1,2-diyl, propene-1,3-diyl, but-1-ene-1,4-diyl, but-1-ene-1,3-diyl, but-2-ene-1,4-diyl, buta-1,3-diene-1,4-diyl, pent-2-ene-1,5-diyl, hex-3-ene-1,6-diyl and hexa-2,4-diene-1,6-diyl.

It is further preferred that the alkenediyl radical is a cyclic alkenediyl radical having from 4 to 8, preferably 5 or 6 carbon atoms.

With regard to the definition of optionally substituted aryl as a substituent for $R^9$ reference is made to the definition of optionally substituted aryl above.

Within the scope of the invention as a whole, optionally substituted heterocyclyl preferably includes:

Aliphatic, saturated or unsaturated heterocyclic 5- to 8-membered cyclic radicals having from 1 to 3, preferably from 1 to 2 heteroatoms, selected from N, O or S, and which can optionally carry from 1 to 3 substituents, wherein with regard to possible substituents reference can be made to the definition of possible substituents of alkyl. Preferred are 5- or 6-membered saturated or unsaturated, optionally substituted heterocyclic radicals, such as tetrahydrofuran-2-yl, tetrahydrofuran-3-yl, tetrahydro-thiophene-2-yl, tetrahydro-thiophene-3-yl, pyrrolidin-1-yl, pyrrolidin-2-yl, pyrrolidin-3-yl, morpholin-1-yl, morpholin-2-yl, morpholin-3-yl, piperidin-1-yl, piperidin-2-yl, piperidin-3-yl, piperidin-4-yl, piperazin-1-yl, piperazin-2-yl, tetrahydropyran-2-yl, tetrahydropyran-3-yl, tetrahydropyran-4-yl, etc., which can optionally be fused with aromatic rings, etc.

Further, within the scope of the invention as a whole, optionally substituted heterocycly includes heteroaromatic hydrocarbon radicals having from 4 to 9 ring-carbon atoms, which additionally have preferably 1 to 3 identical or different heteroatoms from the group S, O, N in the ring, and which thus preferably form 5- to 12-membered heteroaromatic radicals, which may preferably be monocyclic but even bicyclic. Preferred aromatic heterocyclic radicals include: pyridinyl, such as pyridin-2-yl, pyridin-3-yl and pyridin-4-yl, pyridyl-N-oxid, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo[b]thienyl, benzo[b]furyl, indazolyl, chinolyl, isochinolyl, naphthyridinyl, chinazolinyl. 5- or 6-membered aromatic heterocycles such as e.g. pyridinyl, particularly pyridin-2-yl, pyridyl-N-oxid, pyrimidyl, pyridazinyl, furyl and thienyl are preferred.

The heterocyclyl radicals according to the invention may preferably be substituted by 1 to 3 identical or different substituents selected, for example, from hydroxy, halogen, as defined above, cyano, amino, as defined below, mercapto, alkyl, as defined above, acyl, as defined below, and alkoxy, as defined above, aryloxy, as defined above, heterocyclyloxy, as defined above, aryl, as defined above, heterocyclyl, as defined herein.

Heterocyclyl preferably includes: tetrahydrofuranyl, pyrrolidinyl, morpholinyl, piperidinyl or tetrahydropyranyl, pyridinyl, pyridyl-N-oxid, pyrimidyl, pyridazinyl, pyrazinyl, thienyl, furanyl, pyrrolyl, pyrazolyl, imidazolyl, thiazolyl, oxazolyl or isoxazolyl, indolizinyl, indolyl, benzo[b]thienyl, benzo[b]furyl, indazolyl, chinolyl, isochinolyl, naphthyridinyl, chinazolinyl, chinoxazolinyl. 5- or 6-membered heterocycles such as e.g. morpholinyl, as well as aromatic heterocycles such as e.g. pyridyl, pyridyl-N-oxid, pyrimidyl, pyridazinyl, furanyl, thienyl as well as chinolyl and isochinolyl are preferred. Preferred are mMorpholinyl, pyridyl, pyrimidyl and furanyl. A particularly preferred heterocyclyl includes: morpholinyl, pyridyl, such as pyridin-2-yl, pyridin-3-yl, pyridin-4-yl, pyrimidinyl, such as pyrimidin-2-yl and pyrimidin-5-yl, pyrazin-2-yl, thienyl, such as thien-2-yl and thien-3-yl as well as furanyl, such as furan-2-yl and furan-3-yl.

Within the scope of the present invention, $R^9$ is particularly preferably alkanediyl, more preferably alkanediyl having 1, 2 and 3 carbon atoms corresponding to methylene ($-CH_2-$), 1,2-ethanediyl ($-CH_2CH_2-$), 1,2-isopropanediyl ($-CH_2-C(CH_3)H-$ or $-C(CH_3)H-CH_2-$), respectively, or 1,3-propanediyl ($-CH_2CH_2CH_2-$). Preferably $R^9$ is 1,2-ethanediyl ($-CH_2CH_2-$), 1,3-propanediyl ($-CH_2CH_2CH_2-$) or 1,2-isopranediyl.

In the general formula (1), $X^1$ is selected from the group consisting of:
a single bond,
carbonyl ($-CO-$),
sulfur ($-S-$),
oxygen ($-O-$),
sulfoxy ($-SO-$),
sulfonyl ($-SO_2-$),
azo ($-N=N-$) and
an optionally substituted, saturated or unsaturated aliphatic radical having from 1 to 6 carbon atoms.

Within the scope of the present invention, an optionally substituted, saturated or unsaturated aliphatic radical having from 1 to 6 carbon atoms for $X^1$ includes: optionally substituted alkanediyl as defined above, optionally substituted alkenediyl as defined above, and alkynediyl. $X^1$ is preferably alkanediyl, alkenediyl or alkynediyl having up to 4, preferably having up to 2 carbon atoms, such as methylene ($-CH_2-$), which can optionally be substituted by hydroxyl (such as, for example, $-CH(OH)-$).

Compounds of the general formula (1) in which $X^1$ is carbonyl ($-CO-$) are most preferred.

In der general formula (1) $Y^1$ has the meaning of S, thus forming an isothiocyanate group ($-NCS$), or of O, thus forming an isocyanate group ($-NCO$). Preferred is the isothiocyanate group with $Y^1=S$.

In the general formula (1) $Z^1$ has the meaning of hydroxy ($-OH$) or of a radical of the formula $-NR^{10}R^{11}$.

Within the scope of the present invention, the groups $R^{10}$ and $R^{11}$ in the general formula (1) are selected from the following alternatives:
1) $R^{10}$ is hydrogen and $R^{11}$ is optionally substituted alkyl or hydroxyl, or
$R^{11}$ is hydrogen and $R^{10}$ is optionally substituted alkyl or hydroxyl.

The alternatives mentioned under 1) are equivalent. They correspond to the case in which one substituent of $R^{10}$ or $R^{11}$ is hydrogen and the other substituent is optionally substituted alkyl or hydroxyl.
2) $R^{10}$ und $R^{11}$ are each alkyl, wherein at least one of the alkyl groups has at least one substituent, that is to say $R^{10}$ and $R^{11}$ are substituted alkyl, or
3) $R^{10}$ und $R^{11}$, together with the nitrogen atom to which they are bonded, form a saturated or unsaturated, optionally substituted 5- to 8-membered ring which can optionally contain further heteroatoms.

Alternative 1):

Alternative 1) mentioned hereinbefore is a preferred alternative within the scope of the present invention. More preferably, within the scope of this alternative:

$R^{10}$ is hydrogen and $R^{11}$ is substituted alkyl, or
$R^{11}$ is hydrogen and $R^{10}$ is substituted alkyl.

Alkyl here includes linear or branched alkyl having from 1 to 8, preferably from 1 to 6, carbon atoms, cycloalkyl having from 3 to 8, preferably 5 or 6, carbon atoms, or alkyl having from 1 to 4 carbon atoms which is substituted by cycloalkyl. With regard to possible examples of alkyl, reference may be made to the examples mentioned above. Particularly preferably, alkyl is here a C1 to C6, preferably C1 to C5, alkyl group which can be branched or straight-chained, such as in particular methyl, ethyl, propyl, 2-methylpropane, butyl, such as n-butyl, 2-methylbutyl, 3-methylbutyl, pentyl, such as n-pentyl, or n-hexyl. Said alkyl groups are substituted by at least one substituent. Preferred substituents of alkyl are polar functional groups containing one or more heteroatoms, which are preferably selected from: N, O, S, halogen, such as Cl, F, Br and I. In the definition of $R^{10}$ and $R^{11}$, substituents of alkyl include in particular:

A group of the formula:

—$X^2$—$R^{12}$, wherein $X^2$ is selected from the group consisting of:
 carbonyl,
 sulfoxy and
 sulfonyl, and
$R^{12}$ is selected from the group consisting of:
 hydroxy,
 optionally substituted amino and
 optionally substituted alkoxy.

Preferably, $X^2$ is carbonyl and $R^{12}$ is hydroxy.

When $R^{12}$ is hydroxy, the substituent group —$X^2R^{12}$ is carboxy. When $R^{12}$ is optionally substituted amino, the substituent group —$X^2R^{12}$ is, for example, —$CONH_2$, that is to say carbamoyl in the case of $R^{12}$=amino, or —$X^2R^{12}$=mono- or di-alkylaminocarbonyl in the case of $R^{12}$=alkylamino or dialkylamino. When $R^{12}$ is optionally substituted alkoxy, the substituent group —$X^2R^{12}$ is, for example, alkoxycarbonyl in the case of $R^{12}$=alkoxy, that is to say an ester group. Substituents of alkyl in the definition of $R^{10}$ and $R^{11}$ preferably contain at least one group, preferably one or two groups, of the formula —$X^2R^{12}$.

In addition to the group —$X^2R^{12}$ that is preferably present, further preferred substituents of alkyl in the definition of $R^{10}$ and $R^{11}$ include the following substituents:
 guanidino,
 thiol (—SH),
 alkylthio, such as in particular methylthio,
 amino (—$NH_2$),
 mono- or di-alkylamino,
 acylamino, wherein acyl is in particular as defined above,
 saturated, unsaturated or aromatic, mono- or bi-cyclic, optionally substituted heterocyclic radicals, such as, for example, the optionally substituted heteroaromatic radicals mentioned hereinbefore, preferably imidazolyl, such as imidazol-5-yl, 1H-indolyl, such as 1H-indol-3-yl,
 optionally substituted aryl, as described above, in particular phenyl, hydroxyphenyl, such as 4-hydroxyphenyl, alkoxyphenyl, such as methoxyphenyl,
 hydroxyl,
 alkoxy, as described hereinbefore.

Alkyl in the definition of $R^{10}$ and $R^{11}$ preferably has one or two substituents, of which preferably at least one substituent is the group —$X^2R^{12}$.

In a preferred embodiment of alternative 1) mentioned hereinbefore:

$R^{10}$ is hydrogen and $R^{11}$ is a radical A of a compound of the formula $H_2$N-A, or
$R^{11}$ is hydrogen and $R^{10}$ is a radical A of a compound of the formula $H_2$N-A, wherein
A is a radical which is derived formally by cleavage of an amino group (—$NH_2$) from a natural or synthetic amino acid, a natural or synthetic amino acid derivative or a polyamino acid or polyamino acid derivative.

For the purposes of illustration:
If the amino acid $H_2$N-A is, for example, glycine:

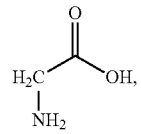

then A=$R^{10}$ or $R^{11}$ is a radical of the formula:

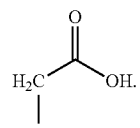

More preferred are compounds according to the invention wherein A is the radical derived formally by cleavage of the amino group from an amino acid or amino acid derivative (for clarification: The formal cleavage of the amino group from an amino acid does not mean the cleavage of an amino group from an amide group ($H_2$N—CO—) that is optionally present but of an amino group bonded to a carbon atom that does not carry further substituents other than H or C. That is to say, the corresponding radical $R^{10}$ or $R^{11}$ formed by cleavage of an amino group from asparagine would be:

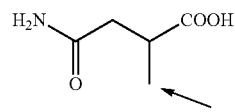

(the arrow denotes the binding site) and not:

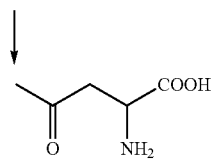

(the arrow denotes the binding site).

Still more preferably, the radical A is formed from the cleavage of a $H_2$N group from the group of the following amino acids:
 alanine, corresponding to the case where $R^{10}$ or $R^{11}$ is ethyl substituted by carboxy, arginine (less preferred), corresponding to the case where $R^{10}$ or $R^{11}$ is butyl substituted by carboxy and guanidino, asparagine, corresponding to the case where $R^{10}$ or $R^{11}$ is ethyl substituted by aminocarbonyl (carbamoyl) and carboxy, aspartic acid, corresponding to the case where $R^{10}$ or $R^{11}$ is ethyl substituted by two carboxy groups, cysteine (less preferred), corresponding to the case where $R^{10}$ or $R^{11}$ is ethyl substituted by thio (—SH) and carboxy, glutamine, corresponding to the case where $R^{10}$ or $R^{11}$ is propyl substituted by aminocarbonyl (carbamoyl) and carboxy, glutamic acid, corresponding to the case where $R^{10}$ or $R^{11}$ is propyl substituted by two carboxy groups, glycine, corresponding to the case where $R^{10}$ or $R^{11}$ is methyl substituted by carboxy, histidine, corresponding to the case where $R^{10}$ or $R^{11}$ is ethyl substituted by carboxy and imidazolyl, isoleucine, corresponding to the case where $R^{10}$ or $R^{11}$ is 2-methylbutyl substituted by carboxy, leucine, corresponding to the case where $R^{10}$ or $R^{11}$ is 3-methylbutyl substituted by carboxy, lysine, corresponding to the case where $R^{10}$ or $R^{11}$ is n-pentyl substituted by carboxy and amino, wherein binding can take place via the amino group adjacent to the carboxyl group:

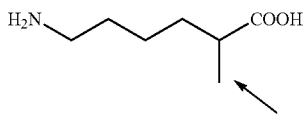

(arrow indicates the bond line or binding site) or via the terminal amino group:

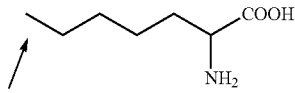

(arrow indicates the bond line or binding site) so that the corresponding compounds of formula (1) look like this:

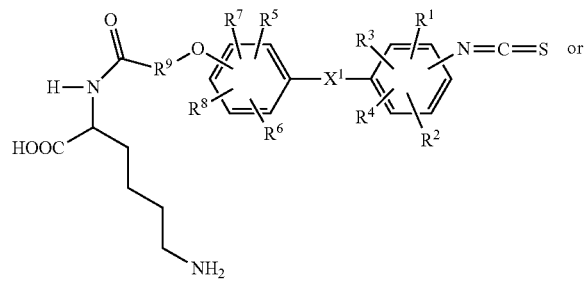

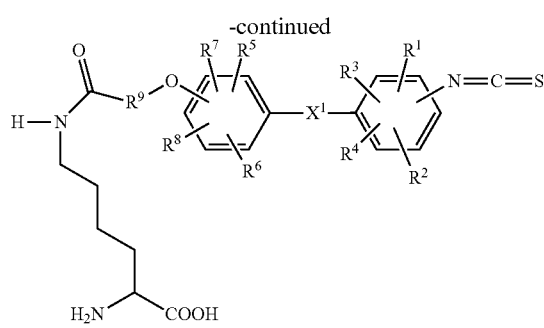

(this applies analogously to other basic amino acids having more than one amino group), methionine, corresponding to the case where $R^{10}$ or $R^{11}$ is n-propyl substituted by carboxy and methylthio, phenylalanine, corresponding to the case where $R^{10}$ or $R^{11}$ is ethyl substituted by carboxy and phenyl, serine, corresponding to the case where $R^{10}$ or $R^{11}$ is ethyl substituted by carboxy and hydroxy, threonine, corresponding to the case where $R^{10}$ or $R^{11}$ is n-propyl substituted by carboxy and hydroxy, tryptophan, corresponding to the case where $R^{10}$ or $R^{11}$ is ethyl substituted by carboxy and indolyl, tyrosine, corresponding to the case where $R^{10}$ or $R^{11}$ is ethyl substituted by carboxy and hydroxyphenyl, and valine, corresponding to the case where $R^{10}$ or $R^{11}$ is 2-methylpropyl substituted by carboxy, or derivatives, such as in particular esters or amides, thereof, corresponding to the case where $R^{12}$ is alkoxy or optionally substituted amino, or derivatives or polyamino acids thereof, which are formed by peptidic linking with one or more further amino acids to the amino acids mentioned hereinbefore or hereinafter.

Further amino acid compounds, or derivatives thereof, from which a radical $R^{10}$ or $R^{11}$ is formed formally by cleavage of an amino group include: creatine (less preferred), creatinine, taurine, or derivatives or polyamino acids thereof, which are formed by peptidic linking with one or more further amino acids to the amino acids mentioned hereinbefore or hereinafter. Also included are so-called non-proteinogenic amino acids, such as, for example: 4-aminobutyric acid (GABA), L-homoserine (2-amino-4-hydroxybutyric acid), ornithine (2,5-diaminovaleric acid), L-(+)-citrulline (N5-(aminocarbonyl)-L-ornithine), 5-hydroxytryptophan (5-HTP), β-alanine (3-aminopropionic acid), β-methylamino-alanine, D-valine, D-alanine, D-glutamic acid and 2,6-diaminopimelic acid.

The derivatives of the above-mentioned amino acid compounds $H_2N$-A are in particular those which have been formed by replacement of a hydrogen atom by a hydroxyl function.

Very preferred are compounds according to the invention wherein the radical A is derived formally by cleavage of the $H_2N$ group from the group of the amino acids glycine and its derivatives and histidine and its derivatives.

Most preferred are compounds according to the invention wherein the radical A is derived by cleavage of the $H_2N$ group from the group of the following amino acids or amino acid derivatives:

glycine:

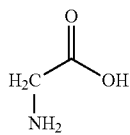

corresponding to $R^{10}$ or $R^{11}=$

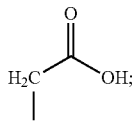

glycineamide:

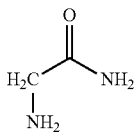

(2-amino-acetamide), corresponding to $R^{10}$ or $R^{11}=$

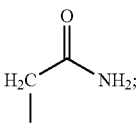

glycine ethyl ester:

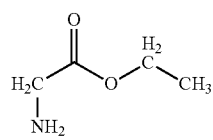

(amino-acetic acid ethyl ester), corresponding to $R^{10}$ or $R^{11}=$

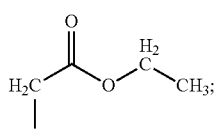

histidine:

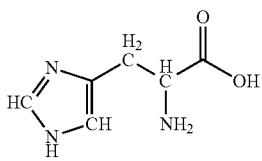

corresponding to $R^{10}$ or $R^{11}=$

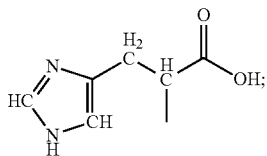

or the histidineamide:

(2-amino-3-(1H-imidazol-4-yl)-propionamide), corresponding to $R^{10}$ or $R^{11}=$ With the exception of glycine, all amino acids contain asymmetric carbon atoms. The compounds according to the invention in which $R^{10}$ or $R^{11}$ is a radical A which is formed formally by cleavage of an amino group from a natural amino acid therefore have the natural configuration (L configuration) of the amino acid. This is also true of compounds that are formed formally by cleavage of an amino group from an amino acid derivative, a polyamino acid and polyamino acid derivatives. According to the invention, however, the case where the amino acids have the non-natural D configuration, such as D-alanine, D-glutamic acid, etc., is also included.

Preference is given according to the invention to compounds wherein the amino acids $H_2N$-A have the L configuration, or wherein $R^{10}$ or $R^{11}$ represents the radical A of such an amino acid, and to those compounds wherein the underlying amino acid derivatives, the polyamino acids and the polyamino acid derivatives are derived from amino acids $H_2N$-A having the L configuration.

In view of their better water solubility, preference is further given to compounds in which the radical $R^{10}$ or $R^{11}$ is formed formally by cleavage of a $NH_2$ group from an acidic amino acid having at least two carboxyl groups, such as aspartic acid, glutamic acid. The use of hydroxyl-group-containing amino acids, such as, for example, threonine, can also be preferred from this point of view.

Alternative 2:

In alternative 2) mentioned hereinbefore, wherein $R^{10}$ and $R^{11}$ are each alkyl, wherein at least one of the alkyl groups has at least one substituent, preferably one or two substituents, reference may be made with regard to the definitions and examples of alkyl to those given above in alternative 1). Substituents of alkyl accordingly include examples given for "optionally substituted alkyl", such as hydroxy, halogen and cyano. In addition, possible substituents of alkyl in alternative 2) also include the examples given for $R^{10}$ and $R^{11}$ in alternative 1) described hereinbefore, such as
guanidino,
thiol (—SH),
alkylthio, such as in particular methylthio,
amino (—$NH_2$),
mono- or di-alkylamino,
acylamino, wherein acyl is in particular as defined above,
saturated, unsaturated or aromatic, mono- or bi-cyclic, optionally substituted heterocyclic radicals, such as, for example, the above-mentioned optionally substituted heteroaromatic radicals, preferably imidazolyl, such as imidazol-5-yl, 1H-indolyl, such as 1H-indol-3-yl,
optionally substituted aryl, as described above, in particular phenyl, hydroxyphenyl, such as 4-hydroxyphenyl, alkoxyphenyl, such as methoxyphenyl,
hydroxy,
alkoxy, as described hereinbefore, and
a group of the formula:

—$X^2$—$R^{12}$, wherein $X^2$ and $R^{12}$ are as defined above, and, in particular, also the radicals which result formally from the cleavage of the $NH_2$ group from the amino acids $NH_2$-A.

Alternative 3):

In alternative 3) mentioned hereinbefore, wherein $R^{10}$ and $R^{11}$, together with the nitrogen atom to which they are bonded, form a saturated or unsaturated, optionally substituted 5- to 8-membered ring which can optionally contain further heteroatoms, possible ring systems consisting of $R^{10}$ and $R^{11}$ and the nitrogen atom to which they are bonded preferably include 5- or 6-membered, optionally substituted rings, such as piperidin-1-yl, morpholin-4-yl, thiomorpholin-4-yl, pyrrolidin-1-yl, oxazolidin-3-yl, thiazolidin-3-yl, 2-carboxyl-pyrrolidin-1-yl (prolyl), 3- or 4-hydroxy-carboxyl-pyrrolidin-1-yl (3- or 4-hydroxy-prolyl), etc. Prolyl and hydroxy-prolyl are particularly preferred.

In context of the present invention compounds wherein $Z^1$ has the meaning of hydroxy (—OH), or pharmaceutically acceptable salts thereof, such as particularly sodium, potassium or calcium salts, are particularly preferred.

Isocyanate and isothiocyanate compounds that are particularly preferred according to the invention are those wherein $R^1$, $R^2$, $R^3$, $R^4$, $R^5$, $R^6$, $R^7$ and $R^8$ are in each case hydrogen.

Isocyanate and isothiocyanate compounds that are particularly preferred according to the invention are those wherein $X^1$ is carbonyl.

Isocyanate and isothiocyanate compounds that are particularly preferred according to the invention are those wherein $R^9$ is a linear, branched or cyclic alkanediyl, preferably linear alkanediyl having from 1 to 6 carbon atoms, still more preferably methylene (—$CH_2$—) or ethane-1,2-diyl or 1,3-propanediyl or 1,2-isopropanediyl.

Isocyanate and isothiocyanate compounds that are particularly preferred according to the invention are those wherein $Z^1$ is hydroxy.

Isocyanate and isothiocyanate compounds that are particularly preferred according to the invention are those wherein the radicals $X^1$ and the radical

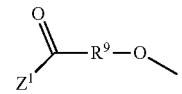

on the phenylene radical are in the para-position relative to one another.

Isocyanate and isothiocyanate compounds that are particularly preferred according to the invention are those wherein the radicals $X^1$ and the radical

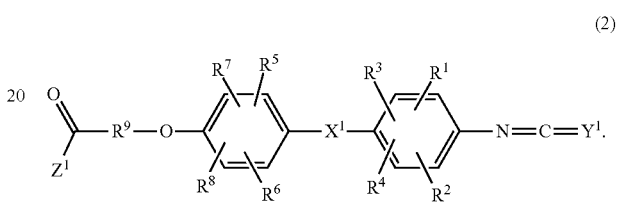

on the phenylene radical are in the para-position relative to one another.

Particular preference is given according to the invention to compounds of formula (2):

(2)

Particular preference is given according to the invention to compounds of formula (1) or (2) wherein
$Y^1$=S or O,
$R^1$, $R^2$, $R^3$, $R^4$, $R^5$, $R^6$, $R^7$ and $R^8$ are in each case hydrogen,
$R^9$ is linear, branched or cyclic alkanediyl,
$Z^1$ is hydroxy or a radical of the formula —$NR^{10}R^{11}$, wherein
$R^{10}$ is hydrogen and $R^{11}$ is a radical A of a compound of the formula $H_2$N-A, or
$R^{11}$ is hydrogen and $R^{10}$ is a radical A of a compound of the formula $H_2$N-A, wherein
A in each case is a radical derived by cleavage of the amino group (—$NH_2$) from a natural or synthetic amino acid, a natural or synthetic amino acid derivative or a polyamino acid or polyamino acid derivative, and
$X^1$ is carbonyl (—CO—).

According to the invention most preferred are compounds of the formula (1) or (2), wherein
$Y^1$=S or O,
$R^1$, $R^2$, $R^3$, $R^4$, $R^5$, $R^6$, $R^7$ and $R^8$ in each case are hydrogen,
$R^9$ is linear, branched or cyclic alkanediyl,
$Z^1$ is hydroxy, and
$X^1$ is carbonyl (—CO—).

Most preferred are compounds, selected from the group as illustrated in the following examples 1 to 70, or pharmaceutically acceptable salts thereof, particularly the sodium salts thereof.

(In these structural formulae, a structural element of the formula

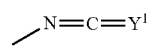

for example, denotes a dimethylamino group, that is to say the methyl groups are represented by single lines, a notation which is well known to the person skilled in the art.

Analogously,

represents an abbreviated notation for a methylene radical (—CH$_2$—)).

Further, according to the invention are particularly preferred compounds of the formula (1) wherein R$^{10}$ is hydrogen and R$^{11}$ is substituted alkyl, or R$^{11}$ is hydrogen and R$^{10}$ is substituted alkyl, wherein substituted alkyl is an alkyl group having at least one sulfonic acid radical, sulfonic acid ester radical or sulfonamido radical. Particular preference is given in this connection to compounds in which substituted alkyl in the definition of R$^{10}$ or R$^{11}$ is a radical of the formula:

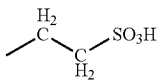

which is derived from taurine (2-aminoethanesulfonic acid).

Isocyanate and isothiocyanate compounds according to the invention that contain basic groups can be used in the form of their pharmaceutically acceptable salts with pharmaceutically acceptable acids, such as, for example, salts with mineral acids, carboxylic acids and sulfonic acids, such as, for example, with hydrochloric acid, hydrobromic acid, hydroiodic acid, sulfuric acid, phosphoric acid, tartaric acid, methanesulfonic acid, hydroxyethanesulfonic acid, aceturic acid (acetylglycine), maleic acid, propionic acid, fumaric acid, toluenesulfonic acid, benzenesulfonic acid, trifluoroacetic acid, naphthalene-1,5-disulfonic acid, salicylic acid, benzoic acid, lactic acid, malic acid, 3-hydroxy-2-naphthoic acid, citric acid or acetic acid.

Isocyanate and isothiocyanate compounds according to the invention that contain acidic groups can be used in the form of their pharmaceutically acceptable salts with pharmaceutically acceptable bases, such as, for example, salts with alkali or alkaline earth hydroxides, such as NaOH, KOH, Ca(OH)$_2$, Mg(OH)$_2$, etc., amine compounds, such as ethylamine, diethylamine, triethylamine, ethyldiisopropylamine, ethanolamine, diethanolamine, triethanolamine, methylglucamine, dicyclohexylamine, dimethylaminoethanol, procaine, dibenzylamine, N-methylmorpholine, arginine, lysine, ethylenediamine, N-methylpiperidine, 2-amino-2-methyl-1-propanol, 2-amino-2-methyl-1,3-propanediol, 2-amino-2-hydroxylmethyl-1,3-propanediol (TRIS), etc.

The water solubility, or the solubility in physiological saline, and accordingly optionally also the activity, of the compounds according to the invention can be influenced significantly by salt formation in general, specifically also by the choice of counter-ion.

However, the water solubility or the solubility in physiological saline, and accordingly optionally also the activity, of the compounds according to the invention is also significantly dependent under certain circumstances on the basic structure of the compounds themselves. By varying the structure of the substituent group R$^9$ the water solubility and thus the physiological compatibility can be specifically varied.

A high degree of water solubility of the compounds according to the invention is not absolutely critical because the predominant proportion of the substance is probably in protein-bound form in the bloodstream. Rather, it is generally important that the substances are recognized as substrate for a transport system in the body. In connection with the present invention, the so-called OATs (organic anion transporters) and OATPs (organic anion transporter proteins) are presumably of particular importance. However, these do not have 100% specificity for anions. An example thereof of digitoxin. Peptide transporters can also be discussed as relevant uptake and excretion mechanisms which recognize the amino acid or amino acid amide radical.

The use of 2-amino-2-hydroxyl-methyl-1,3-propanediol (TRIS) and sodium salts is preferred against the background of increasing the water solubility of the compounds according to the invention.

Depending on their structure, the compounds according to the invention can exist in stereoisomeric forms (enantiomers, diastereoisomers) when asymmetric carbon atoms are present. The invention therefore also includes the use of the enantiomers or diastereoisomers and mixtures thereof. The enantiomerically pure forms can optionally be obtained by conventional processes of optical resolution, such as by fractional crystallisation of diastereoisomers thereof by reaction with optically active compounds. Where the compounds according to the invention can occur in tautomeric forms, the present invention includes the use of all tautomeric forms.

The present invention relates further to compounds of formula (1) for use as medicaments, and to the use of the compounds of formula (1) in the preparation of a medicament, in particular for the treatment of cancer diseases.

The compounds according to the invention can be used, for example, in the treatment of the following types of tumour: adenocarcinoma, uveal melanoma, acute leukaemia, acoustic neuroma, ampullary carcinoma, anal carcinoma, astrocytomas, basalioma, pancreatic cancer, connective tissue tumor, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, ependymoma, epithelial cancer types, Ewing's tumors, gastrointestinal tumors, gallbladder cancer, gallbladder carcinomas, uterine cancer, cervical cancer, glioblastoma, gynaecological tumors, neck, nose and ear tumors, haematological neoplasias, hairy cell leukaemia, urethral cancer, skin cancer, brain tumors (gliomas), brain metastases, testicular cancer, hypophysis tumor, carcinoids, Kaposi's sarcoma, laryngeal cancer, germ cell tumor, bone cancer, colorectal carcinoma, head/neck tumors (tumors of the neck, nose and ear region), colon carcinoma, craniopharyngeoma, cancer in the mouth region and on the lip, liver cancer, liver metastases, leukaemia, lid tumor, lung cancer, lymph gland cancer (Hodgkin's/non-Hodgkin's), lymphomas, stomach cancer, malignant melanoma, malignant neoplasma, malignomas of the gastrointestinal tract, mammary carcinoma, rectal cancer, medulloblastomas, melanoma, meningeomas, Merkel cell carcinoma, Hodgkin's disease, Mycosis fungoides, cancer of the nose, neurinoma, neuroblastoma, kidney cancer, renal cell carcinomas, non-Hodgkin's lymphomas, oligodendroglioma, oesophageal carcinoma, osteolytic carcinomas and osteoplastic carcinomas, osteosarcoma, ovarian carcinoma, pancreatic carcinoma, penile cancer, plasmocytoma, squamous cell carcinomas of the head and neck, prostate cancer, pharyngeal cancer, rectal carcinoma, retinoblastoma, vaginal cancer, thyroid carcinoma, Schneeberg lung disease, oesophageal cancer, spinalioma, T-cell lymphoma (Mycosis fungoides), thymoma, tube carcinoma, tumors of the eye, urethral cancer, urological tumors, urothelial carcinoma, vulval cancer, wart involvement, tumors of soft parts, soft part sarcoma, Wilms' tumor, cervical carcinoma and tongue cancer. Reference can additionally be made to the list of cancer types in, for example, WO2007061978 (page 16, line 22 to page 18, line 2) or in US2007135424A1 (page 9, left-hand column, section 122), which are to be regarded as part of the disclosure of the present invention. The compounds of the present invention can also be used in further indications, such as those mentioned in US2007135424A1 in sections 123 to 142.

The compounds according to the invention are used particularly preferably for the treatment of breast cancer, intestinal cancer or melanomas.

The compounds according to the invention are used particularly preferably for the treatment of breast cancer.

The invention relates further to the use of the compounds of formula (1) in combination with at least one further chemotherapeutic agent for the treatment of cancer.

The compounds of the present invention can accordingly also be used in combination with further chemotherapeutic agents known in the treatment of cancer or tumors and/or in combination with medicaments which are administered together with the chemotherapeutic agents during chemotherapy. Examples of such chemotherapeutic agents which can be used in combination and of other medicaments used in chemotherapy will be found, for example, in WO2007061978 under the heading "Combination Therapy" (page 23, line 1 to page 30, line 18) or in US2007135424A1 (sections 153 to 171), to the whole of the contents of which reference is accordingly made.

The present invention relates further to pharmaceutical compositions comprising at least one of the compounds of formula (1) together with at least one pharmacologically acceptable carrier, auxiliary substance or solvent. These are conventional pharmaceutical carriers, auxiliary substances or solvents. The mentioned pharmaceutical compositions are, for example, suitable for inhalation or for intravenous, intraperitoneal, intramuscular, intravaginal, intrabuccal, percutaneous, subcutaneous, mucocutaneous, oral, rectal, transdermal, topical, intradermal, intragastral or intracutaneous administration and are in the form of, for example, pills, tablets, enteric-coated tablets, film-coated tablets, layered tablets, retard formulations for oral, subcutaneous or cutaneous administration (in particular in plaster form), depot formulation, dragées, suppositories, gels, ointments, syrup, powders for inhalation, granules, suppositories, emulsions, dispersions, microcapsules, microformulations, nanoformulations, liposomal formulations, capsules, enteric-coated capsules, powders, powders for inhalation, microcrystalline formulations, sprays for inhalation, powders, drops, nasal drops, nasal sprays, aerosols, ampoules, solutions, juices, suspensions, emulsions, infusion solutions or injection solutions, etc.

The compounds according to the invention can be administered in pharmaceutical compositions that can comprise various organic or inorganic carriers and/or auxiliary materials as are conventionally used for pharmaceutical purposes, in particular for solid medicament forms, such as, for example, excipients (such as sucrose, starch, mannitol, sorbitol, lactose, glucose, cellulose, talc, calcium phosphate, calcium carbonate), binders (such as cellulose, methylcellulose, hydroxypropylcellulose, polypropylpyrrolidone, gelatin, gum arabic, polyethylene glycol, sucrose, starch), disintegrators (such as starch, hydrolysed starch, carboxymethylcellulose, calcium salt of carboxymethylcellulose, hydroxypropyl starch, sodium glycol starch, sodium bicarbonate, calcium phosphate, calcium citrate), glidants and lubricants (such as magnesium stearate, talc, sodium lauryl sulfate), an agent that forms a good taste (such as citric acid, menthol, glycine, orange powder), preservatives (such as sodium benzoate, sodium bisulfite, methylparaben, propylparaben), stabilisers (such as citric acid, sodium citrate, acetic acid, and multicarboxylic acids from the Titriplex group, such as, for example, diethylenetriaminepentaacetic acid (DTPA)), suspending agents (such as methylcellulose, polyvinylpyrrolidone, aluminium stearate), dispersing agents, diluents (such as water, organic solvents), beeswax, cocoa butter, polyethylene glycol, white petrolatum, etc.

Liquid medicament forms, such as solutions, suspensions and gels, conventionally comprise a liquid carrier, such as water and/or pharmaceutically acceptable organic solvents. Such liquid formulations can also comprise pH-adjusting agents, emulsifiers or dispersing agents, buffering agents, preservatives, wetting agents, gelling agents (for example methylcellulose), colourings and/or flavourings. The compositions can be isotonic, that is to say they can have the same osmotic pressure as blood. The isotonicity of the composition can be adjusted by the use of sodium chloride or other pharmaceutically acceptable agents, such as, for example, dextrose, maltose, boric acid, sodium tartrate, propylene glycol or other inorganic or organic soluble substances. The viscosity of the liquid compositions can be adjusted using a pharmaceutically acceptable thickener, such as methylcellulose. Other suitable thickeners include, for example, xanthan, carboxymethylcellulose, hydroxypropylcellulose, carbomer and the like. The preferred concentration of the thickener will depend on the chosen agent. Pharmaceutically acceptable preservatives can be used to increase the life of the liquid composition. Benzyl alcohol can be suitable, although a large number of preservatives including, for example, paraben, thimerosal, chlorobutanol or benzalkonium chloride can likewise be used.

Diethylenetriaminepentaacetic acid (DTPA) in particular is found to be a suitable stabiliser for the solid or liquid pharmaceutical formulations of the compounds according to the invention, such as in particular the compound of Example 2a).

The active ingredient can be administered, for example, in a unit dose of from 0.01 mg/kg to 500 mg/kg body weight, for example up to 1 to 4 times per day. However, the dosage can be increased or reduced according to the age, weight and condition of the patient, the severity of the disease or the mode of administration.

The invention is illustrated in detail by the following examples. The examples merely constitute exemplifications, and the person skilled in the art is able to extend the specific examples to further claimed compounds.

EXAMPLES

Object of the invention are in particular the following example compounds:

| No | Isothiocyanate Compound |
|---|---|
| 1a | 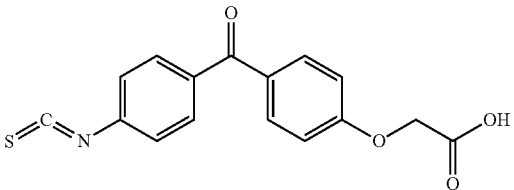 [SMILES: O=C(O)COc1ccc(C(=O)c2ccc(N=C=S)cc2)cc1] |
| 2a | 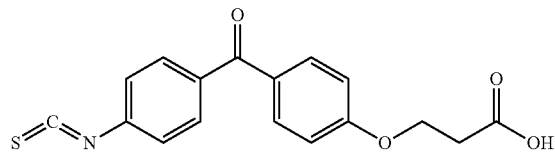 [SMILES: O=C(O)CCOc1ccc(C(=O)c2ccc(N=C=S)cc2)cc1] |
| 3a | 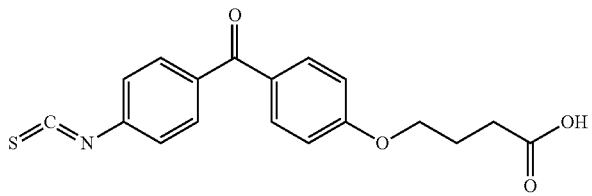 |
| 4a | 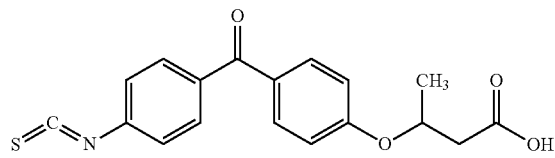 [SMILES: CC(CC(=O)O)Oc1ccc(C(=O)c2ccc(N=C=S)cc2)cc1] |
| 5a | 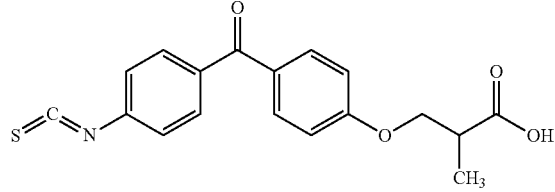 [SMILES: CC(COc1ccc(C(=O)c2ccc(N=C=S)cc2)cc1)C(=O)O] |
| 6a | 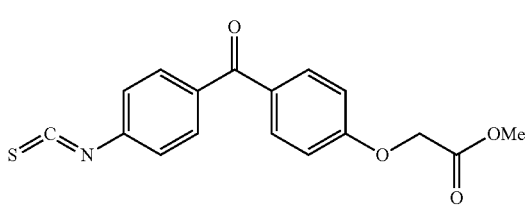 [SMILES: COC(=O)COc1ccc(C(=O)c2ccc(N=C=S)cc2)cc1] |
| 7a | 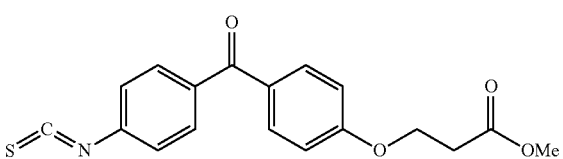 [SMILES: COC(=O)CCOc1ccc(C(=O)c2ccc(N=C=S)cc2)cc1] |
| 8a | 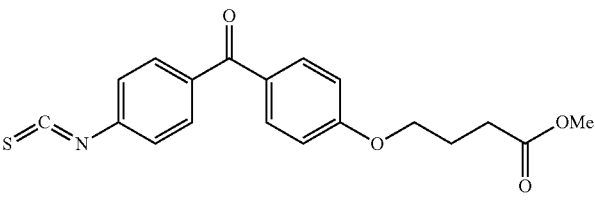 [SMILES: COC(=O)CCCOc1ccc(C(=O)c2ccc(N=C=S)cc2)cc1] |

9a 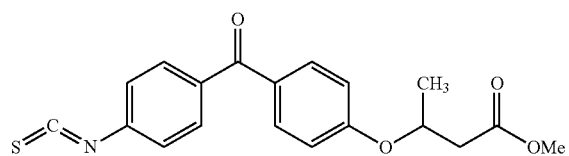 [SMILES: COC(=O)CC(C)Oc1ccc(C(=O)c2ccc(N=C=S)cc2)cc1]
10a 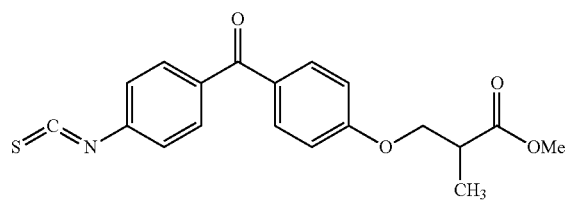
11a 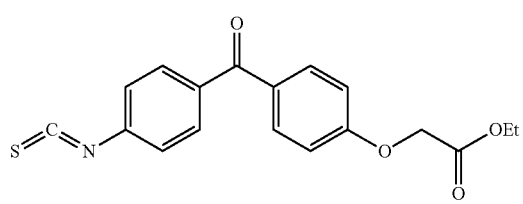 [SMILES: CCOC(=O)COc1ccc(C(=O)c2ccc(N=C=S)cc2)cc1]
12a 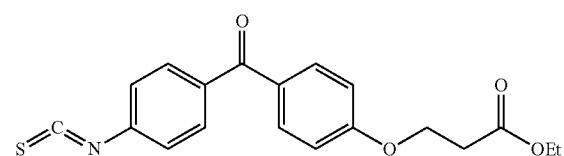
13a 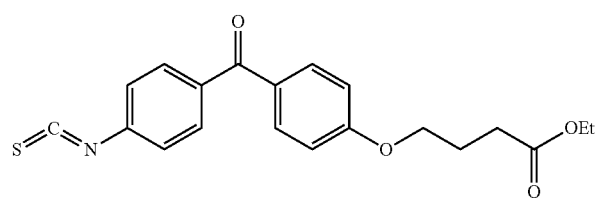 [SMILES: CCOC(=O)CCCOc1ccc(C(=O)c2ccc(N=C=S)cc2)cc1]
14a 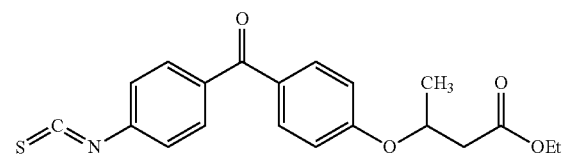 [SMILES: CCOC(=O)CC(C)Oc1ccc(C(=O)c2ccc(N=C=S)cc2)cc1]
15a 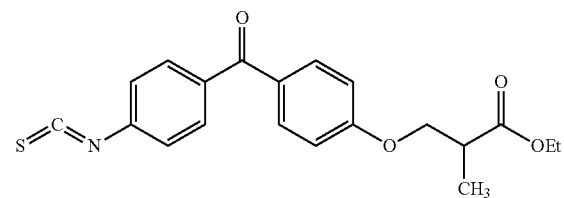 [SMILES: CCOC(=O)C(C)COc1ccc(C(=O)c2ccc(N=C=S)cc2)cc1]
16a 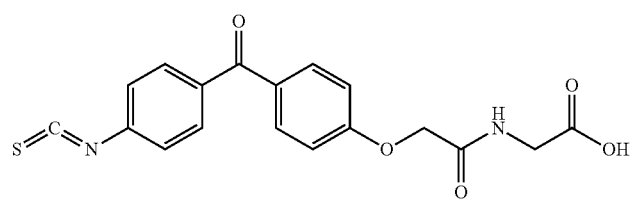 [SMILES: O=C(O)CNC(=O)COc1ccc(C(=O)c2ccc(N=C=S)cc2)cc1]

-continued
17a
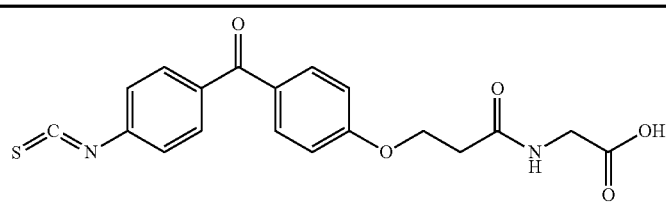
18a
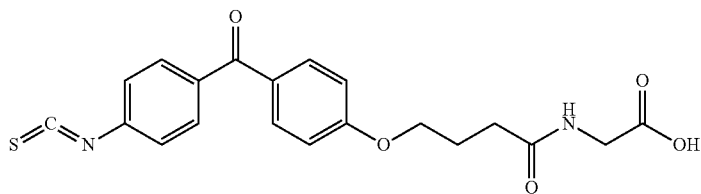 [SMILES: O=C(O)CNC(=O)CCCOc1ccc(C(=O)c2ccc(N=C=S)cc2)cc1]
19a
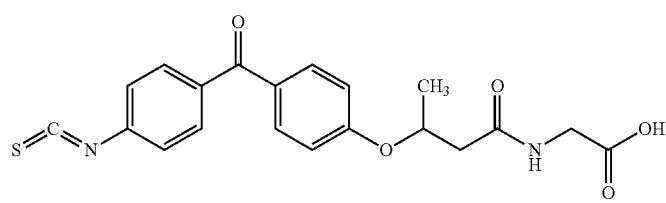 [SMILES: CC(CC(=O)NCC(=O)O)Oc1ccc(C(=O)c2ccc(N=C=S)cc2)cc1]
20a
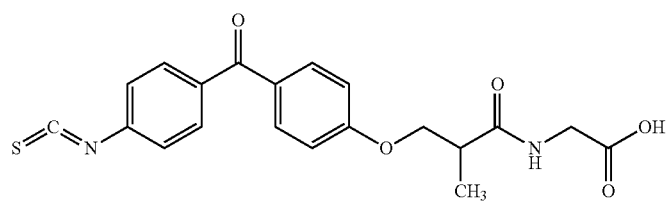 [SMILES: CC(COc1ccc(C(=O)c2ccc(N=C=S)cc2)cc1)C(=O)NCC(=O)O]
21a
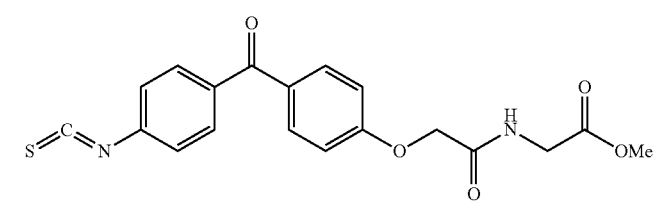 [SMILES: COC(=O)CNC(=O)COc1ccc(C(=O)c2ccc(N=C=S)cc2)cc1]
22a
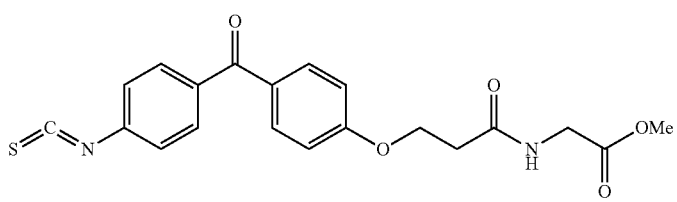 [SMILES: COC(=O)CNC(=O)CCOc1ccc(C(=O)c2ccc(N=C=S)cc2)cc1]
23a
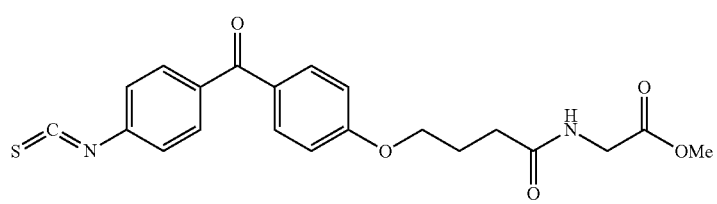 [SMILES: COC(=O)CNC(=O)CCCOc1ccc(C(=O)c2ccc(N=C=S)cc2)cc1]
24a
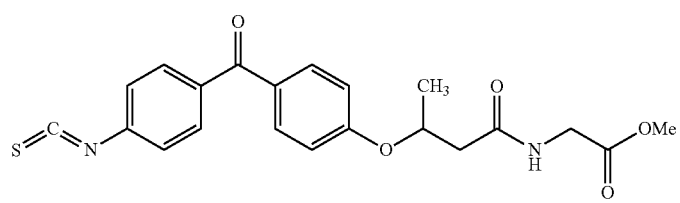 [SMILES: COC(=O)CNC(=O)CC(C)Oc1ccc(C(=O)c2ccc(N=C=S)cc2)cc1]

25a 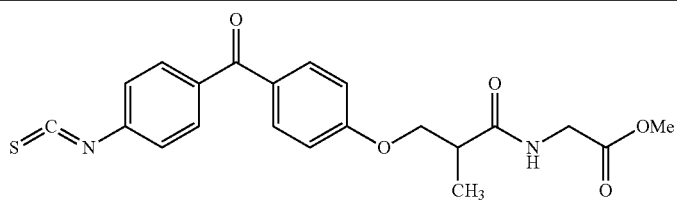
26a 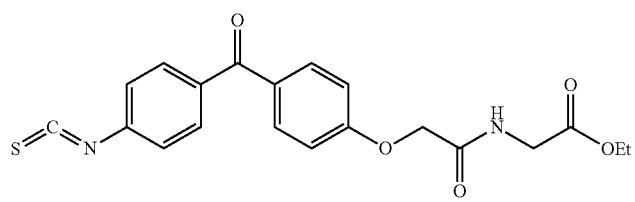 [SMILES: CCOC(=O)CNC(=O)COc1ccc(C(=O)c2ccc(N=C=S)cc2)cc1]
27a 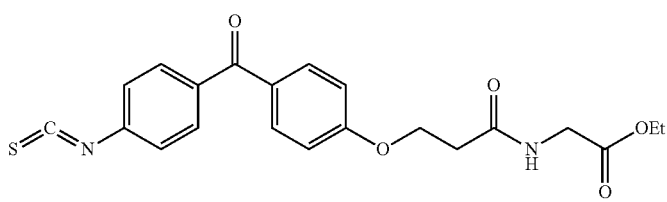 [SMILES: CCOC(=O)CNC(=O)CCOc1ccc(C(=O)c2ccc(N=C=S)cc2)cc1]
28a 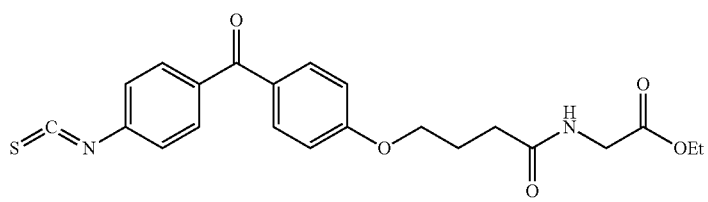 [SMILES: CCOC(=O)CNC(=O)CCCOc1ccc(C(=O)c2ccc(N=C=S)cc2)cc1]
29a 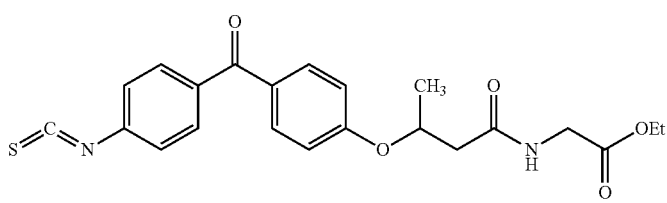 [SMILES: CCOC(=O)CNC(=O)CC(C)Oc1ccc(C(=O)c2ccc(N=C=S)cc2)cc1]
30a 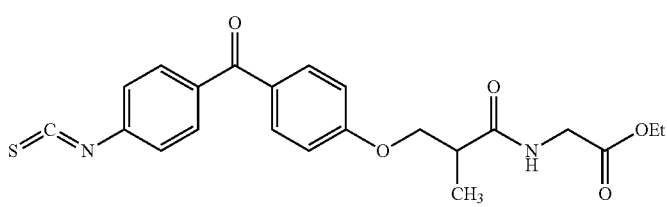 [SMILES: CCOC(=O)CNC(=O)C(C)COc1ccc(C(=O)c2ccc(N=C=S)cc2)cc1]
31a 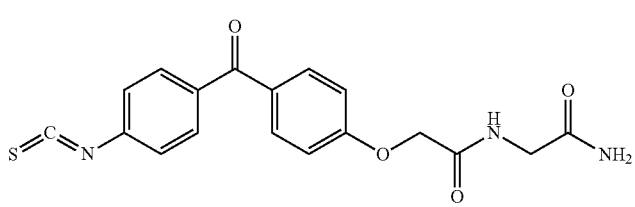 [SMILES: NC(=O)CNC(=O)COc1ccc(C(=O)c2ccc(N=C=S)cc2)cc1]
32a 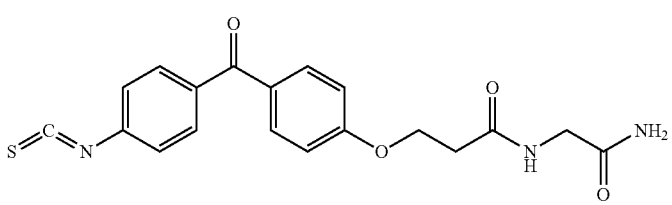 [SMILES: NC(=O)CNC(=O)CCOc1ccc(C(=O)c2ccc(N=C=S)cc2)cc1]

33a 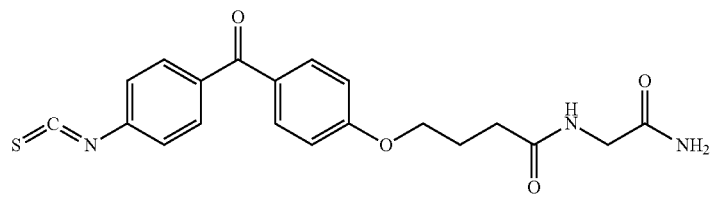 [SMILES: NC(=O)CNC(=O)CCCOc1ccc(C(=O)c2ccc(N=C=S)cc2)cc1]
34a 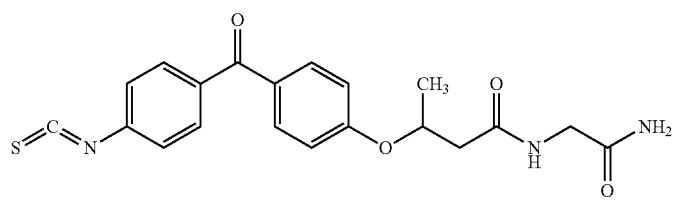 [SMILES: CC(CC(=O)NCC(N)=O)Oc1ccc(C(=O)c2ccc(N=C=S)cc2)cc1]
35a 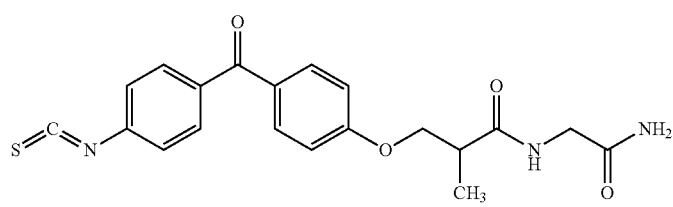 [SMILES: CC(COc1ccc(C(=O)c2ccc(N=C=S)cc2)cc1)C(=O)NCC(N)=O]
36a 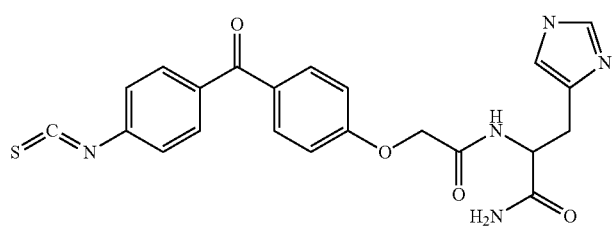 [SMILES: NC(=O)C(Cc1c[nH]cn1)NC(=O)COc1ccc(C(=O)c2ccc(N=C=S)cc2)cc1]
37a 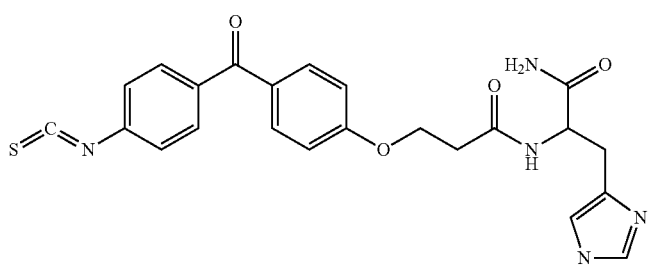 [SMILES: NC(=O)C(Cc1c[nH]cn1)NC(=O)CCOc1ccc(C(=O)c2ccc(N=C=S)cc2)cc1]
38a 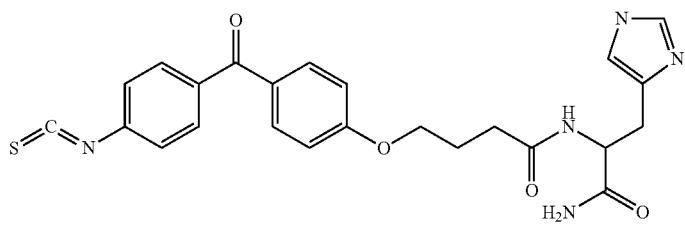 [SMILES: NC(=O)C(Cc1c[nH]cn1)NC(=O)CCCOc1ccc(C(=O)c2ccc(N=C=S)cc2)cc1]
39a 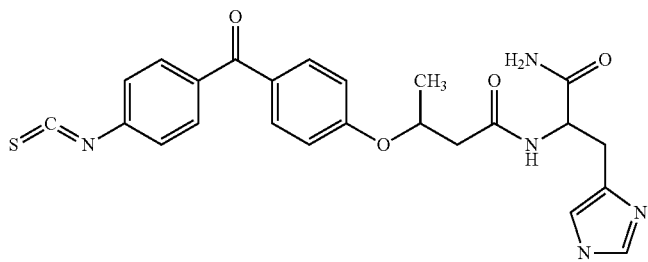 [SMILES: CC(CC(=O)NC(Cc1c[nH]cn1)C(N)=O)Oc1ccc(C(=O)c2ccc(N=C=S)cc2)cc1]

-continued
40a
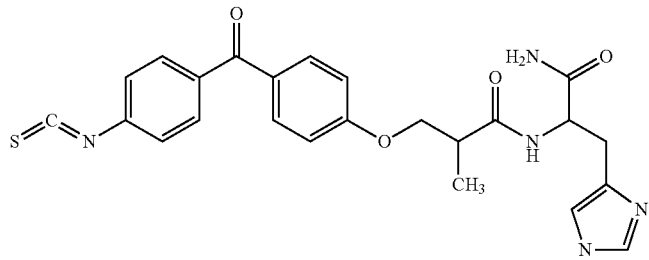 [SMILES: CC(COc1ccc(C(=O)c2ccc(N=C=S)cc2)cc1)C(=O)NC(Cc1c[nH]cn1)C(N)=O]
41a
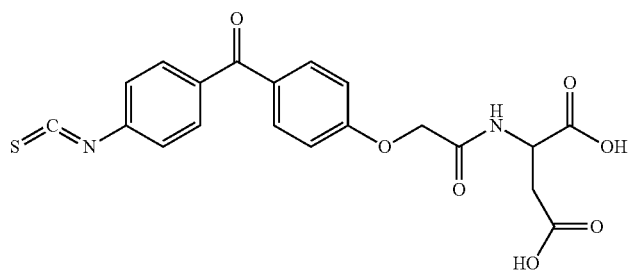 [SMILES: O=C(O)CC(NC(=O)COc1ccc(C(=O)c2ccc(N=C=S)cc2)cc1)C(=O)O]
42a
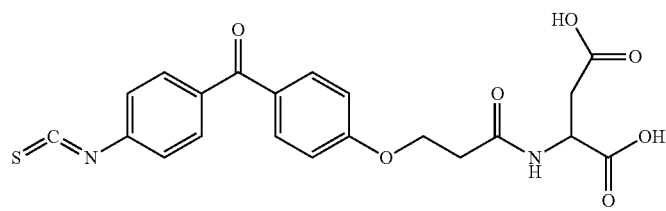 [SMILES: O=C(O)CC(NC(=O)CCOc1ccc(C(=O)c2ccc(N=C=S)cc2)cc1)C(=O)O]
43a
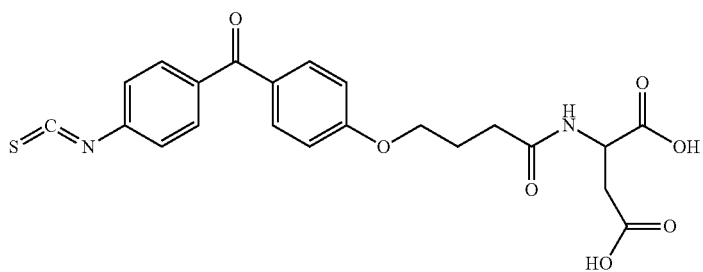 [SMILES: O=C(O)CC(NC(=O)CCCOc1ccc(C(=O)c2ccc(N=C=S)cc2)cc1)C(=O)O]
44a
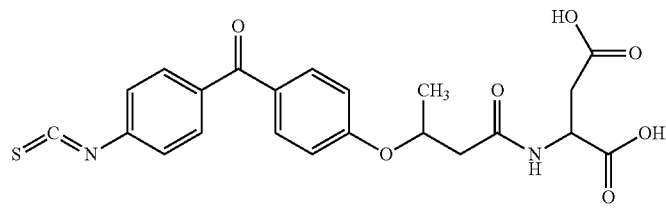 [SMILES: CC(CC(=O)NC(CC(=O)O)C(=O)O)Oc1ccc(C(=O)c2ccc(N=C=S)cc2)cc1]
45a
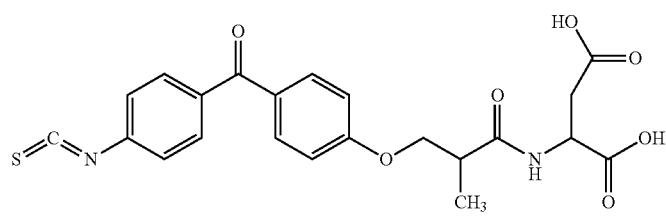 [SMILES: CC(COc1ccc(C(=O)c2ccc(N=C=S)cc2)cc1)C(=O)NC(CC(=O)O)C(=O)O]

-continued
46a
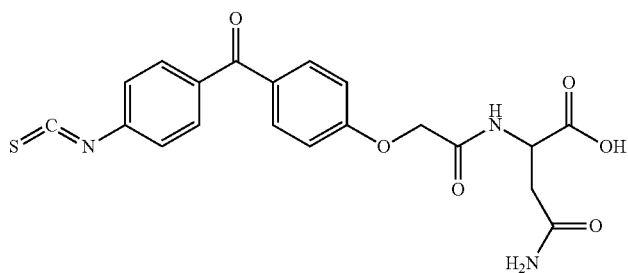 [SMILES: NC(=O)CC(NC(=O)COc1ccc(C(=O)c2ccc(N=C=S)cc2)cc1)C(=O)O]
47a
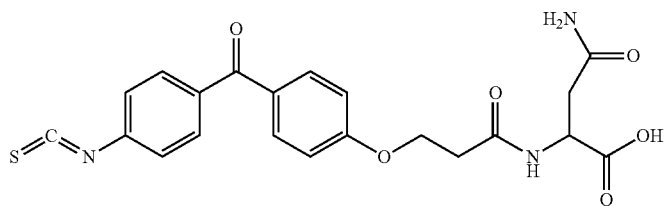 [SMILES: NC(=O)CC(NC(=O)CCOc1ccc(C(=O)c2ccc(N=C=S)cc2)cc1)C(=O)O]
48a
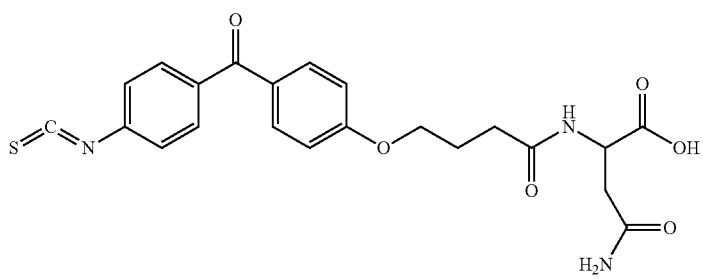 [SMILES: NC(=O)CC(NC(=O)CCCOc1ccc(C(=O)c2ccc(N=C=S)cc2)cc1)C(=O)O]
49a
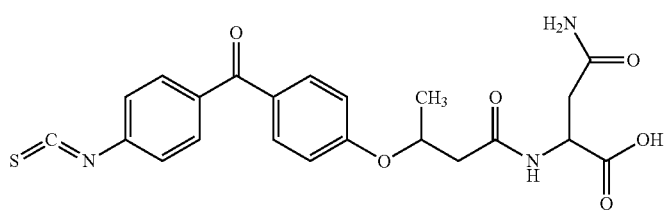 [SMILES: CC(CC(=O)NC(CC(N)=O)C(=O)O)Oc1ccc(C(=O)c2ccc(N=C=S)cc2)cc1]
50a
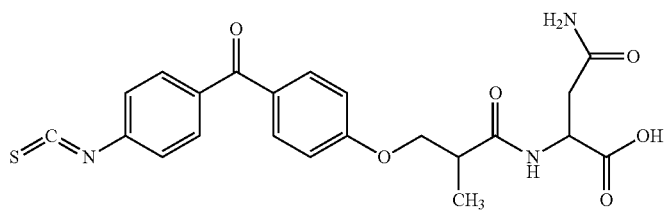 [SMILES: CC(COc1ccc(C(=O)c2ccc(N=C=S)cc2)cc1)C(=O)NC(CC(N)=O)C(=O)O]
51a
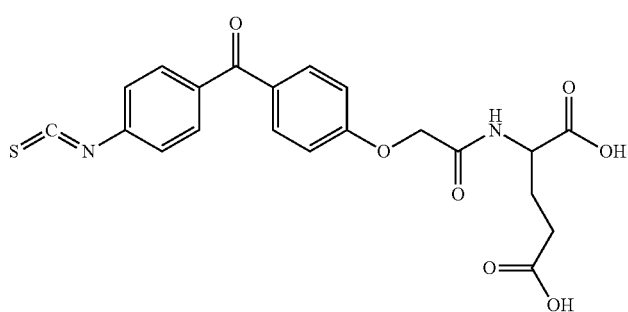 [SMILES: O=C(O)CCC(NC(=O)COc1ccc(C(=O)c2ccc(N=C=S)cc2)cc1)C(=O)O]

-continued
52a
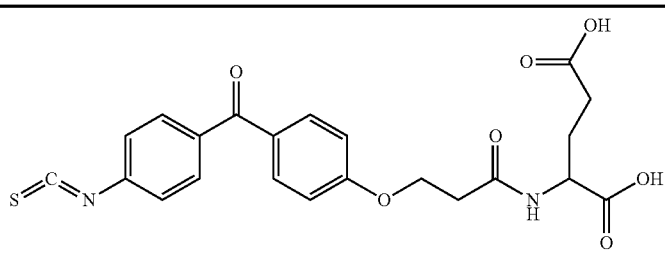
53a
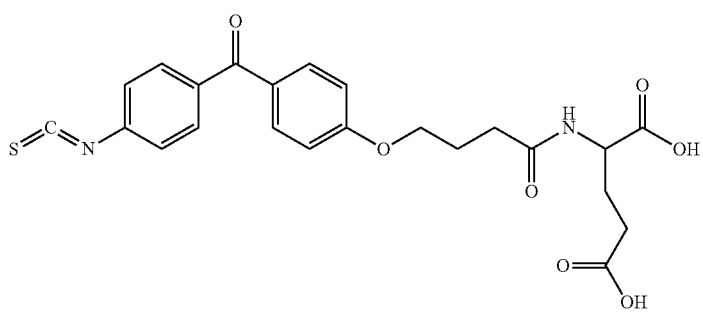 [SMILES: O=C(O)CCC(NC(=O)CCCOc1ccc(C(=O)c2ccc(N=C=S)cc2)cc1)C(=O)O]
54a
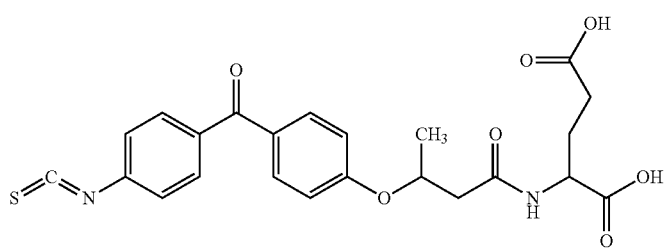 [SMILES: CC(CC(=O)NC(CCC(=O)O)C(=O)O)Oc1ccc(C(=O)c2ccc(N=C=S)cc2)cc1]
55a
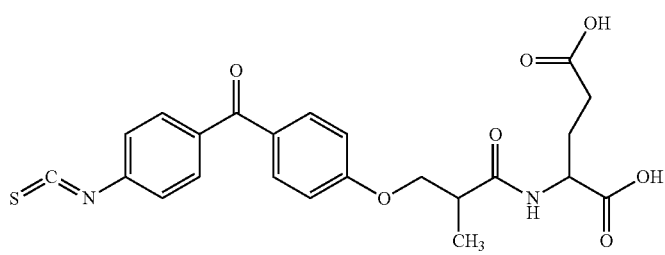 [SMILES: CC(COc1ccc(C(=O)c2ccc(N=C=S)cc2)cc1)C(=O)NC(CCC(=O)O)C(=O)O]
56a
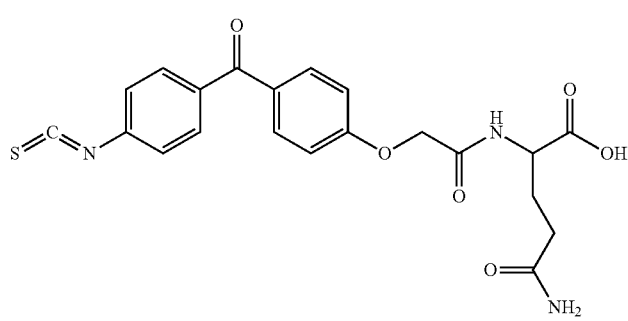 [SMILES: NC(=O)CCC(NC(=O)COc1ccc(C(=O)c2ccc(N=C=S)cc2)cc1)C(=O)O]
57a
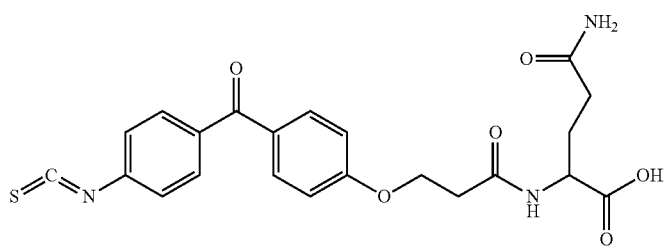

-continued
58a
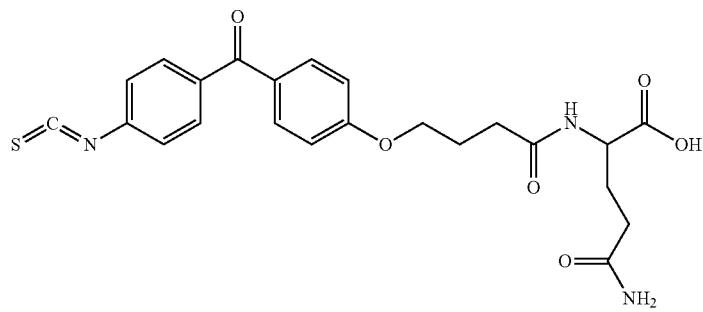 [SMILES: NC(=O)CCC(NC(=O)CCCOc1ccc(C(=O)c2ccc(N=C=S)cc2)cc1)C(=O)O]
59a
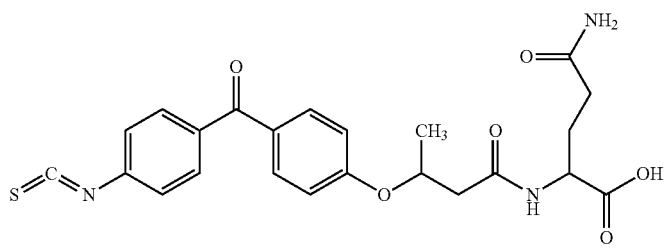 [SMILES: CC(CC(=O)NC(CCC(N)=O)C(=O)O)Oc1ccc(C(=O)c2ccc(N=C=S)cc2)cc1]
60a
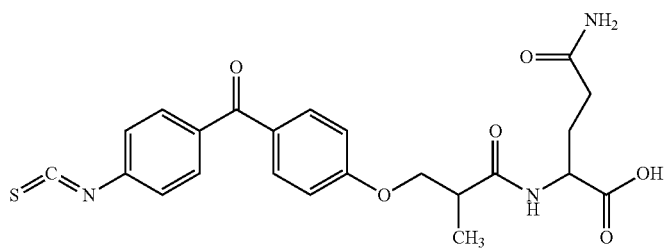 [SMILES: CC(COc1ccc(C(=O)c2ccc(N=C=S)cc2)cc1)C(=O)NC(CCC(N)=O)C(=O)O]
61a
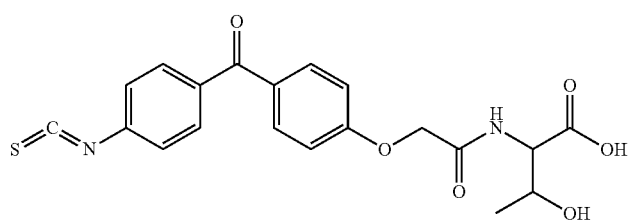 [SMILES: CC(O)C(NC(=O)COc1ccc(C(=O)c2ccc(N=C=S)cc2)cc1)C(=O)O]
62a
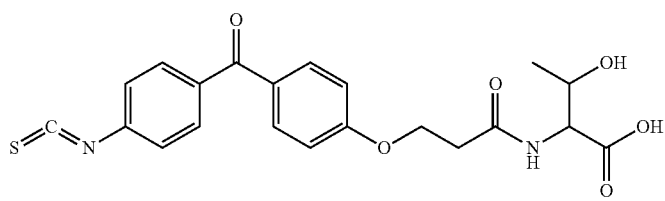 [SMILES: CC(O)C(NC(=O)CCOc1ccc(C(=O)c2ccc(N=C=S)cc2)cc1)C(=O)O]
63a
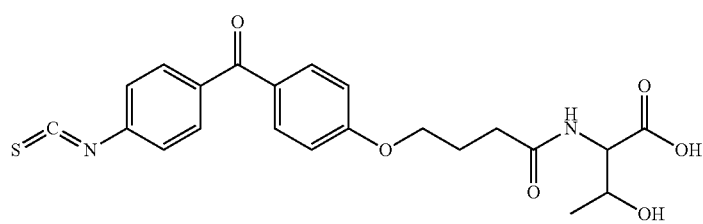 [SMILES: CC(O)C(NC(=O)CCCOc1ccc(C(=O)c2ccc(N=C=S)cc2)cc1)C(=O)O]

-continued
| | |
|---|---|
| 64a | 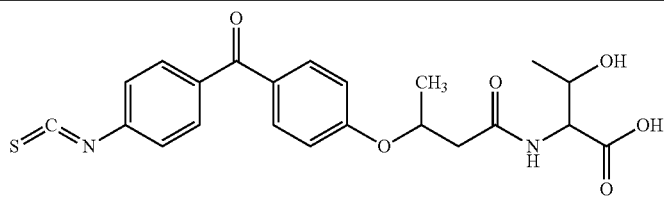 |
| 65a | 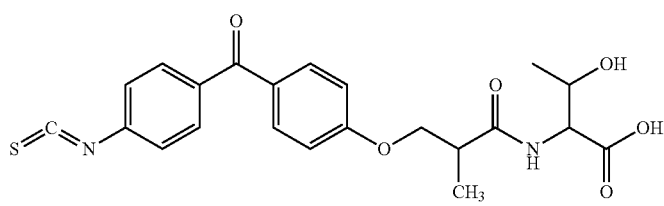 [SMILES: CC(COc1ccc(C(=O)c2ccc(N=C=S)cc2)cc1)C(=O)NC(C(=O)O)C(C)O] |
| 66a | 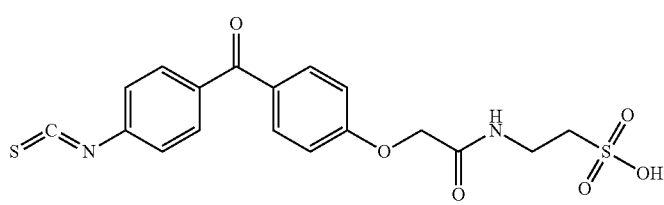 [SMILES: O=C(COc1ccc(C(=O)c2ccc(N=C=S)cc2)cc1)NCCS(=O)(=O)O] |
| 67a | 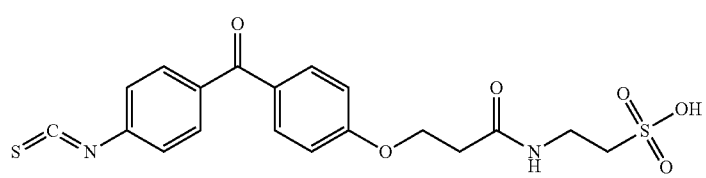 [SMILES: O=C(CCOc1ccc(C(=O)c2ccc(N=C=S)cc2)cc1)NCCS(=O)(=O)O] |
| 68a | 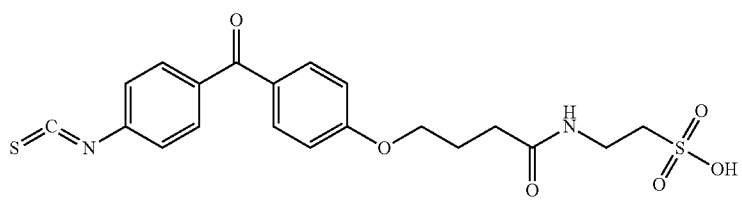 [SMILES: O=C(CCCOc1ccc(C(=O)c2ccc(N=C=S)cc2)cc1)NCCS(=O)(=O)O] |
| 69a | 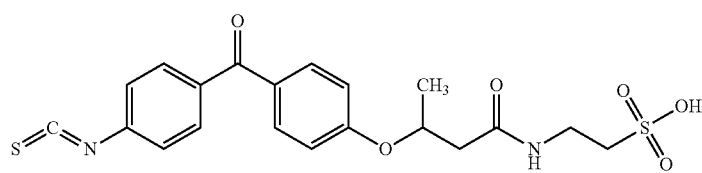 [SMILES: CC(CC(=O)NCCS(=O)(=O)O)Oc1ccc(C(=O)c2ccc(N=C=S)cc2)cc1] |
| 70a | 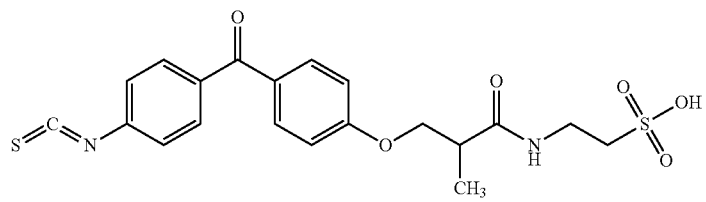 [SMILES: CC(COc1ccc(C(=O)c2ccc(N=C=S)cc2)cc1)C(=O)NCCS(=O)(=O)O] |
| No | Isocyanate Compound |
|---|---|
| 1b | 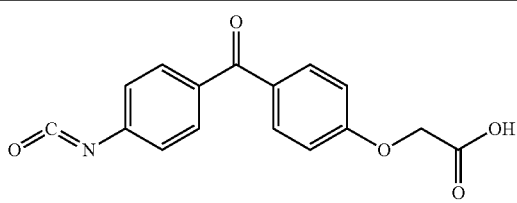 |

-continued
2b
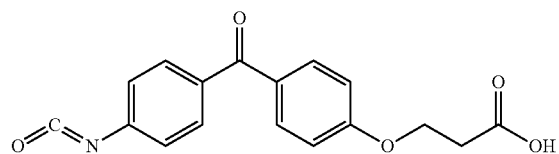
3b
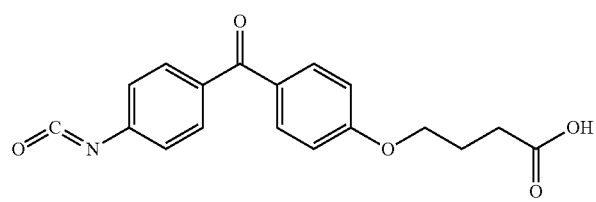 [SMILES: O=C=Nc1ccc(C(=O)c2ccc(OCCCC(=O)O)cc2)cc1]
4b
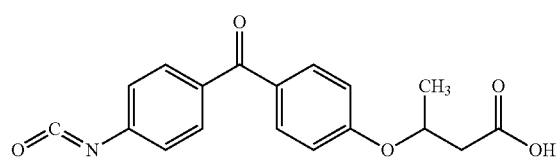
5b
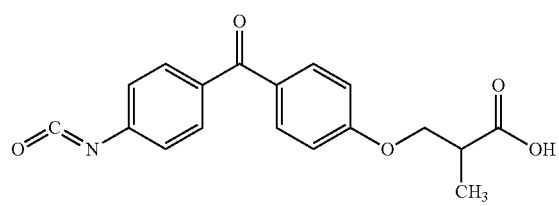
6b
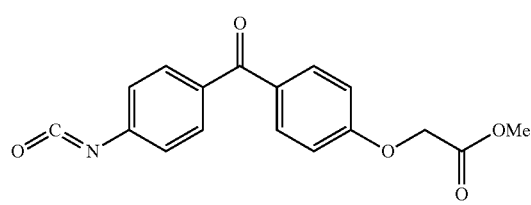 [SMILES: COC(=O)COc1ccc(C(=O)c2ccc(N=C=O)cc2)cc1]
7b
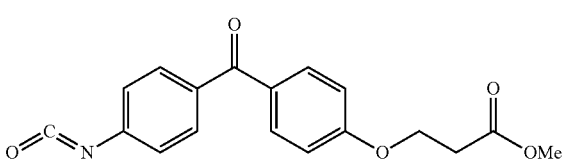 [SMILES: COC(=O)CCOc1ccc(C(=O)c2ccc(N=C=O)cc2)cc1]
8b
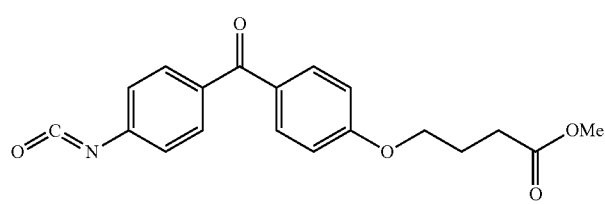 [SMILES: COC(=O)CCCOc1ccc(C(=O)c2ccc(N=C=O)cc2)cc1]
9b
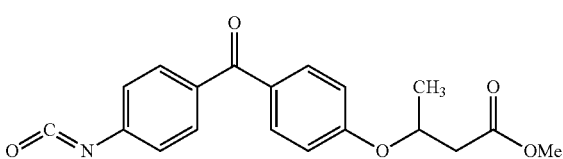 [SMILES: COC(=O)CC(C)Oc1ccc(C(=O)c2ccc(N=C=O)cc2)cc1]

10b 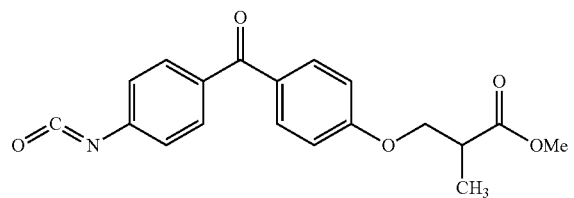 [SMILES: COC(=O)C(C)COc1ccc(C(=O)c2ccc(N=C=O)cc2)cc1]
11b 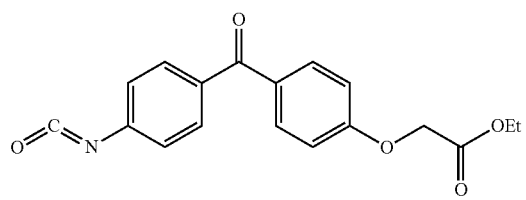 [SMILES: CCOC(=O)COc1ccc(C(=O)c2ccc(N=C=O)cc2)cc1]
12b 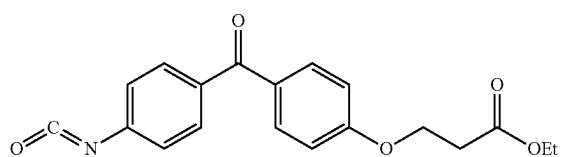 [SMILES: CCOC(=O)CCOc1ccc(C(=O)c2ccc(N=C=O)cc2)cc1]
13b 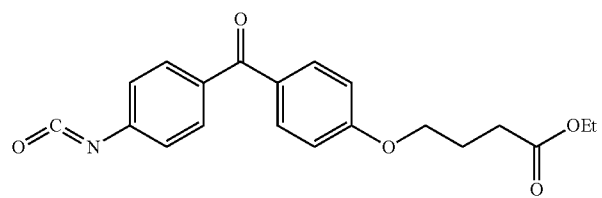 [SMILES: CCOC(=O)CCCOc1ccc(C(=O)c2ccc(N=C=O)cc2)cc1]
14b 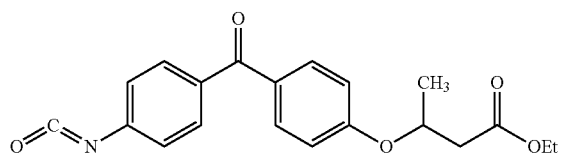 [SMILES: CCOC(=O)CC(C)Oc1ccc(C(=O)c2ccc(N=C=O)cc2)cc1]
15b 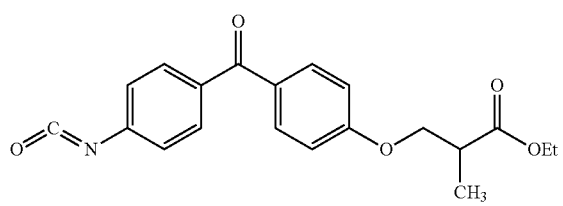 [SMILES: CCOC(=O)C(C)COc1ccc(C(=O)c2ccc(N=C=O)cc2)cc1]
16b 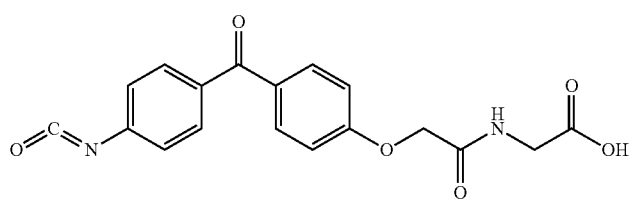 [SMILES: O=C=Nc1ccc(C(=O)c2ccc(OCC(=O)NCC(=O)O)cc2)cc1]
17b 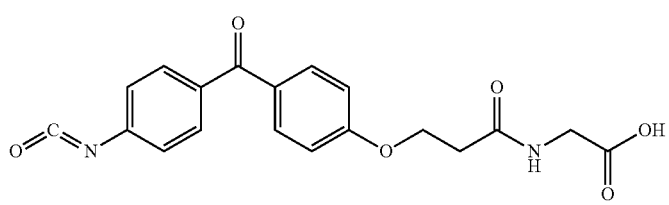 [SMILES: O=C=Nc1ccc(C(=O)c2ccc(OCCC(=O)NCC(=O)O)cc2)cc1]

-continued
18b 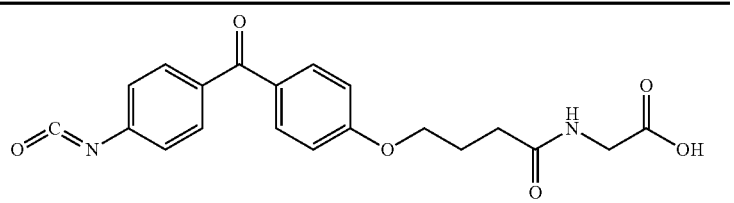
19b 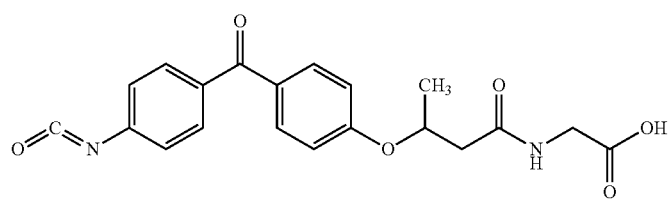 [SMILES: CC(CC(=O)NCC(=O)O)Oc1ccc(C(=O)c2ccc(N=C=O)cc2)cc1]
20b 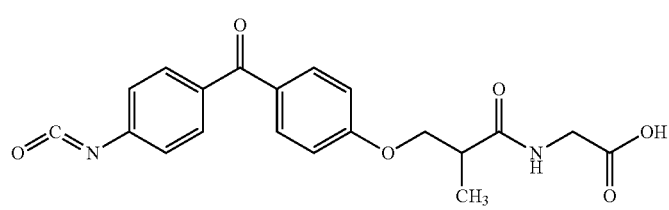 [SMILES: CC(COc1ccc(C(=O)c2ccc(N=C=O)cc2)cc1)C(=O)NCC(=O)O]
21b 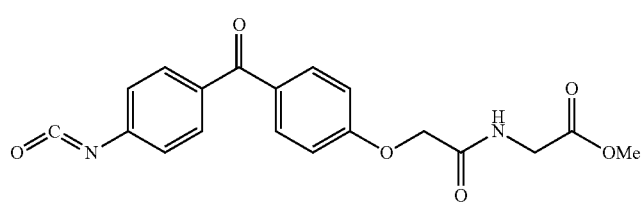 [SMILES: COC(=O)CNC(=O)COc1ccc(C(=O)c2ccc(N=C=O)cc2)cc1]
22b 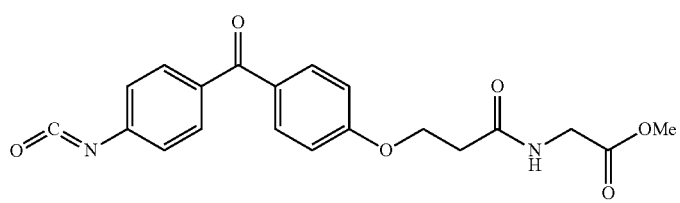 [SMILES: COC(=O)CNC(=O)CCOc1ccc(C(=O)c2ccc(N=C=O)cc2)cc1]
23b 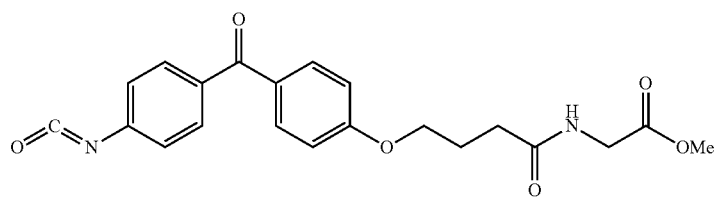 [SMILES: COC(=O)CNC(=O)CCCOc1ccc(C(=O)c2ccc(N=C=O)cc2)cc1]
24b 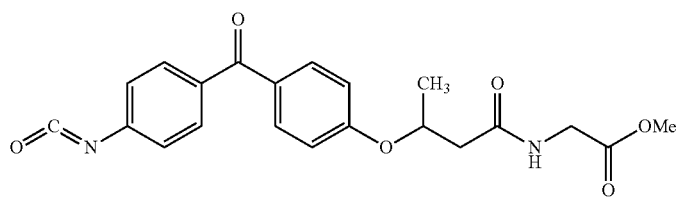 [SMILES: COC(=O)CNC(=O)CC(C)Oc1ccc(C(=O)c2ccc(N=C=O)cc2)cc1]
25b 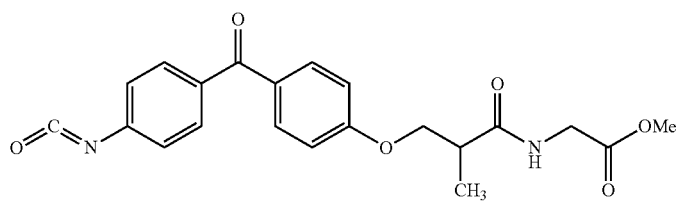 [SMILES: COC(=O)CNC(=O)C(C)COc1ccc(C(=O)c2ccc(N=C=O)cc2)cc1]

-continued
26b 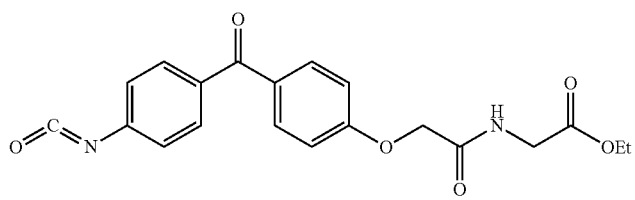 [SMILES: CCOC(=O)CNC(=O)COc1ccc(C(=O)c2ccc(N=C=O)cc2)cc1]
27b 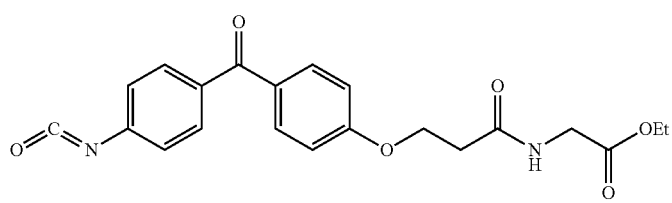 [SMILES: CCOC(=O)CNC(=O)CCOc1ccc(C(=O)c2ccc(N=C=O)cc2)cc1]
28b 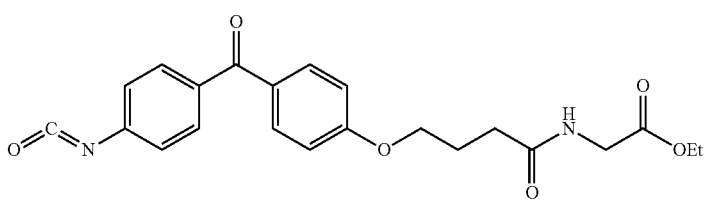 [SMILES: CCOC(=O)CNC(=O)CCCOc1ccc(C(=O)c2ccc(N=C=O)cc2)cc1]
29b 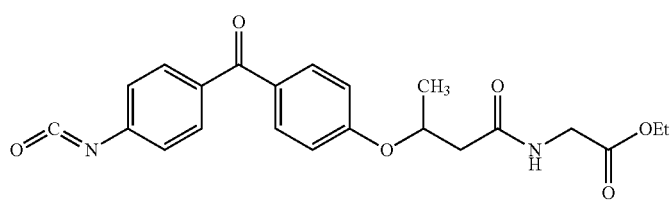 [SMILES: CCOC(=O)CNC(=O)CC(C)Oc1ccc(C(=O)c2ccc(N=C=O)cc2)cc1]
30b 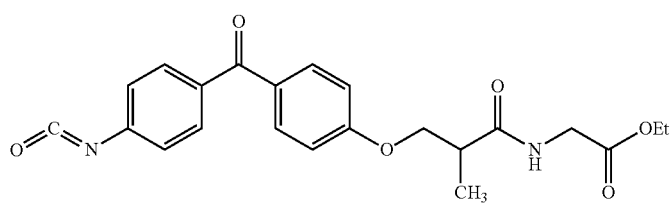 [SMILES: CCOC(=O)CNC(=O)C(C)COc1ccc(C(=O)c2ccc(N=C=O)cc2)cc1]
31b 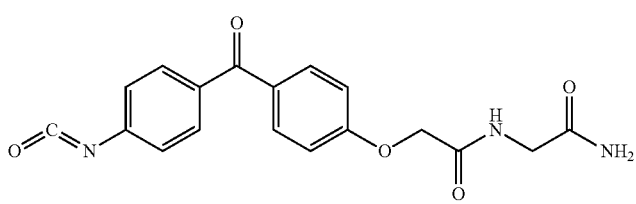 [SMILES: NC(=O)CNC(=O)COc1ccc(C(=O)c2ccc(N=C=O)cc2)cc1]
32b 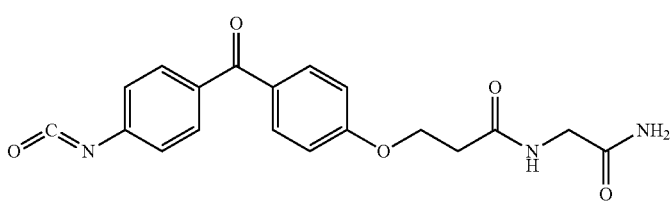 [SMILES: NC(=O)CNC(=O)CCOc1ccc(C(=O)c2ccc(N=C=O)cc2)cc1]

-continued
33b
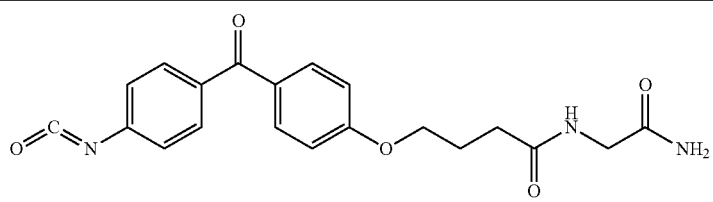
34b
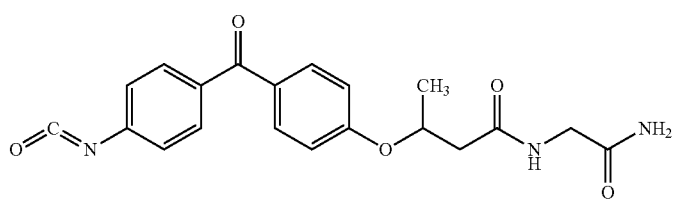 [SMILES: CC(CC(=O)NCC(N)=O)Oc1ccc(C(=O)c2ccc(N=C=O)cc2)cc1]
35b
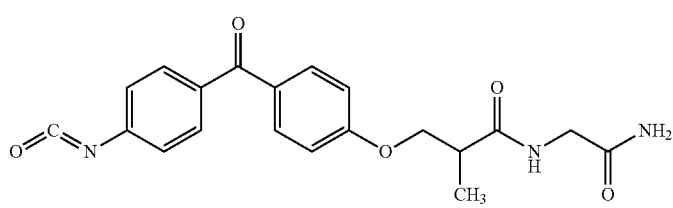 [SMILES: CC(COc1ccc(C(=O)c2ccc(N=C=O)cc2)cc1)C(=O)NCC(N)=O]
36b
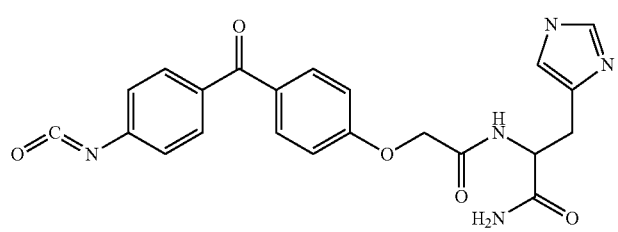 [SMILES: NC(=O)C(Cc1c[nH]cn1)NC(=O)COc1ccc(C(=O)c2ccc(N=C=O)cc2)cc1]
37b
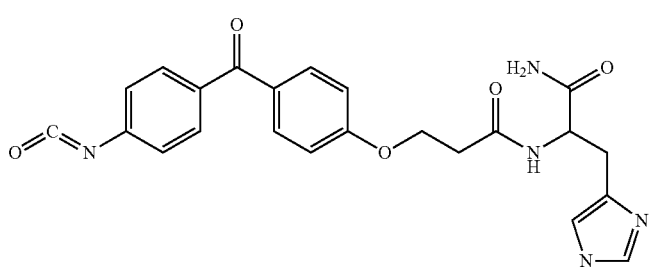 [SMILES: NC(=O)C(Cc1c[nH]cn1)NC(=O)CCOc1ccc(C(=O)c2ccc(N=C=O)cc2)cc1]
38b
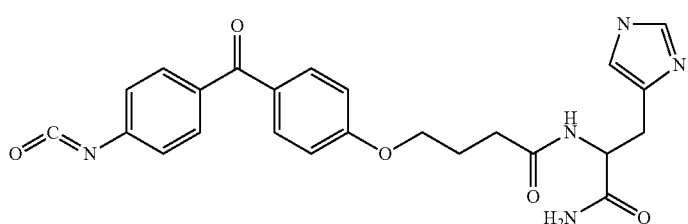
39b
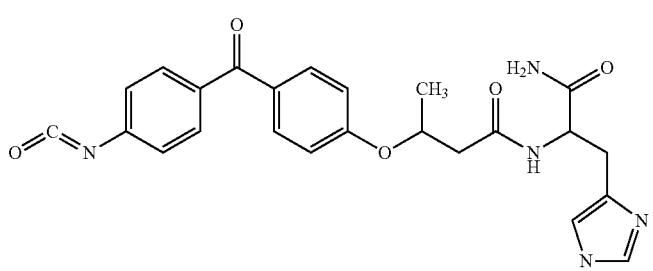 [SMILES: CC(CC(=O)NC(Cc1c[nH]cn1)C(N)=O)Oc1ccc(C(=O)c2ccc(N=C=O)cc2)cc1]

-continued
40b
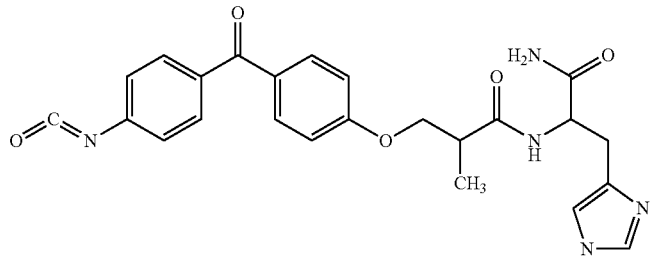 [SMILES: CC(COc1ccc(C(=O)c2ccc(N=C=O)cc2)cc1)C(=O)NC(Cc1c[nH]cn1)C(N)=O]
41b
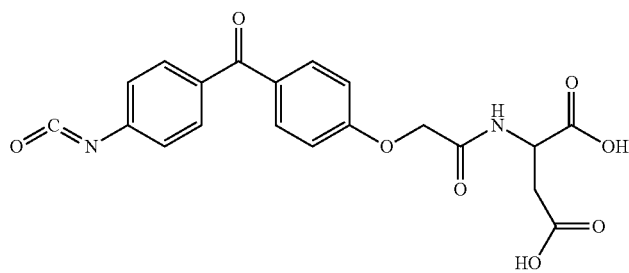 [SMILES: O=C=Nc1ccc(C(=O)c2ccc(OCC(=O)NC(CC(=O)O)C(=O)O)cc2)cc1]
42b
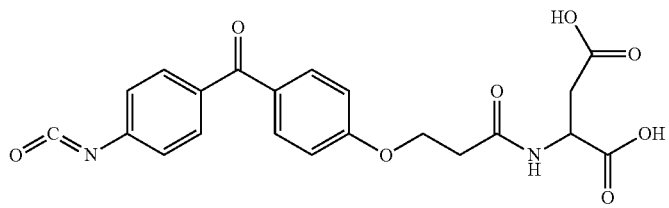 [SMILES: O=C=Nc1ccc(C(=O)c2ccc(OCCC(=O)NC(CC(=O)O)C(=O)O)cc2)cc1]
43b
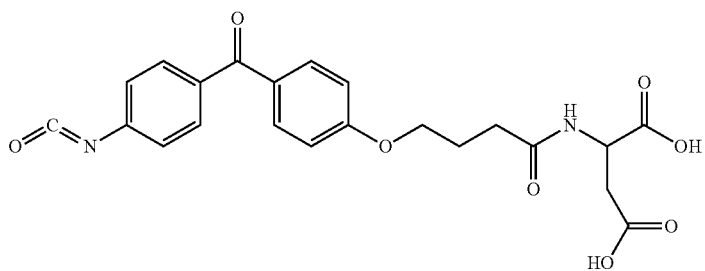 [SMILES: O=C=Nc1ccc(C(=O)c2ccc(OCCCC(=O)NC(CC(=O)O)C(=O)O)cc2)cc1]
44b
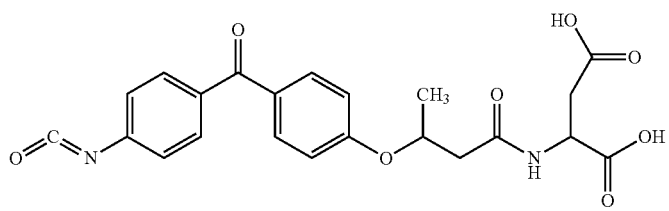 [SMILES: CC(CC(=O)NC(CC(=O)O)C(=O)O)Oc1ccc(C(=O)c2ccc(N=C=O)cc2)cc1]
45b
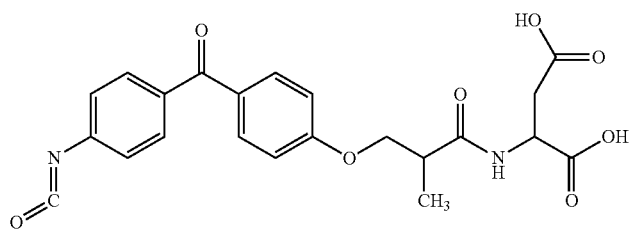 [SMILES: CC(COc1ccc(C(=O)c2ccc(N=C=O)cc2)cc1)C(=O)NC(CC(=O)O)C(=O)O]

46b 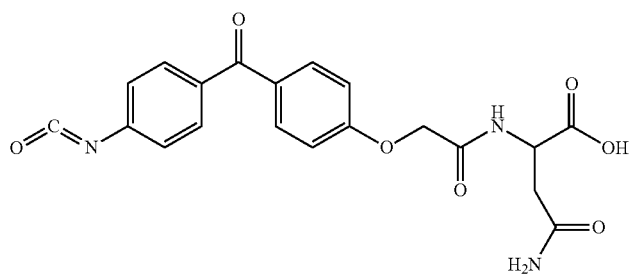 [SMILES: NC(=O)CC(NC(=O)COc1ccc(C(=O)c2ccc(N=C=O)cc2)cc1)C(=O)O]
47b 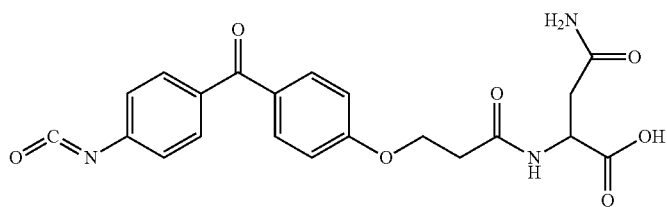 [SMILES: NC(=O)CC(NC(=O)CCOc1ccc(C(=O)c2ccc(N=C=O)cc2)cc1)C(=O)O]
48b 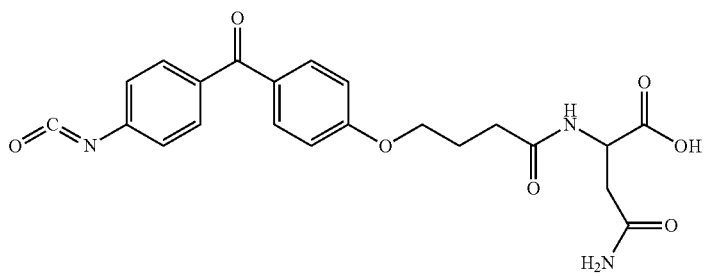 [SMILES: NC(=O)CC(NC(=O)CCCOc1ccc(C(=O)c2ccc(N=C=O)cc2)cc1)C(=O)O]
49b 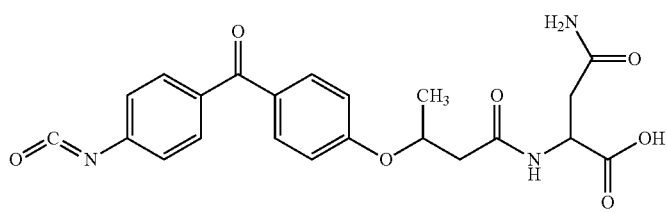
50b 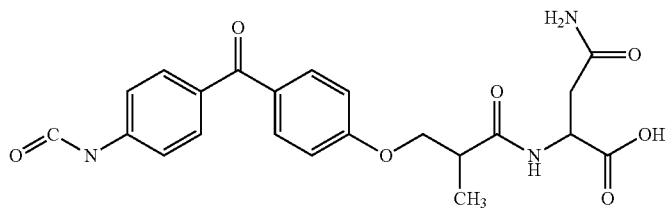 [SMILES: CC(COc1ccc(C(=O)c2ccc(NC=O)cc2)cc1)C(=O)NC(CC(N)=O)C(=O)O]
51b 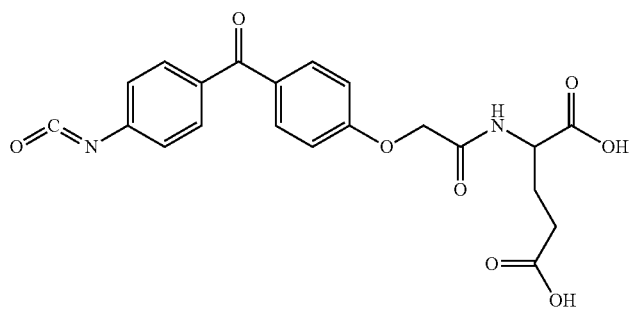 [SMILES: O=C=Nc1ccc(C(=O)c2ccc(OCC(=O)NC(CCC(=O)O)C(=O)O)cc2)cc1]

-continued
52b
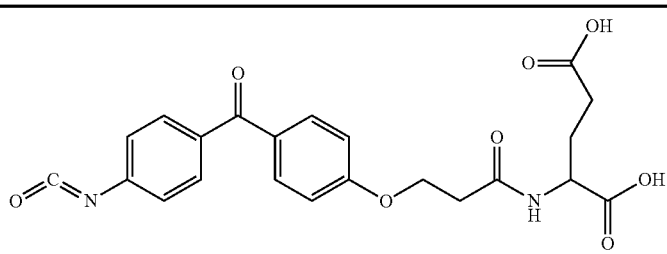
53b
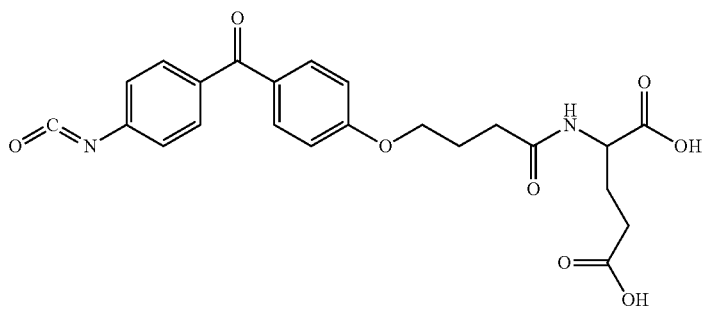 [SMILES: O=C=Nc1ccc(C(=O)c2ccc(OCCCC(=O)NC(CCC(=O)O)C(=O)O)cc2)cc1]
54b
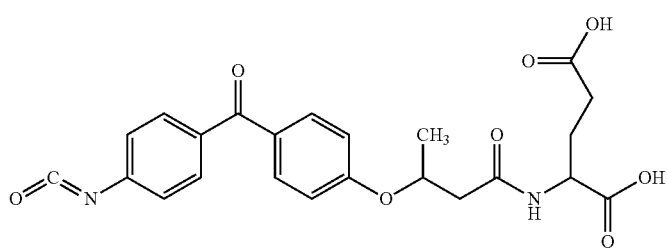 [SMILES: CC(CC(=O)NC(CCC(=O)O)C(=O)O)Oc1ccc(C(=O)c2ccc(N=C=O)cc2)cc1]
55b
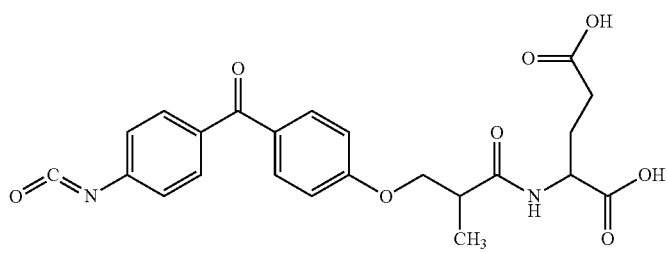 [SMILES: CC(COc1ccc(C(=O)c2ccc(N=C=O)cc2)cc1)C(=O)NC(CCC(=O)O)C(=O)O]
56b
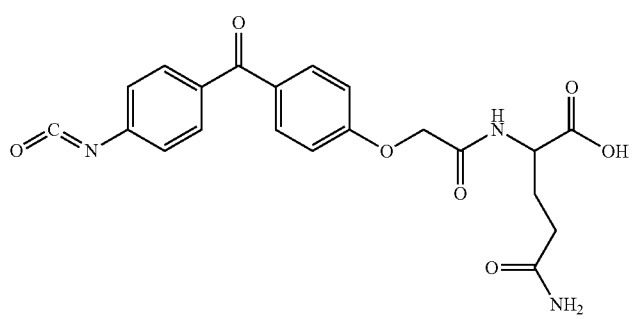 [SMILES: NC(=O)CCC(NC(=O)COc1ccc(C(=O)c2ccc(N=C=O)cc2)cc1)C(=O)O]
57b
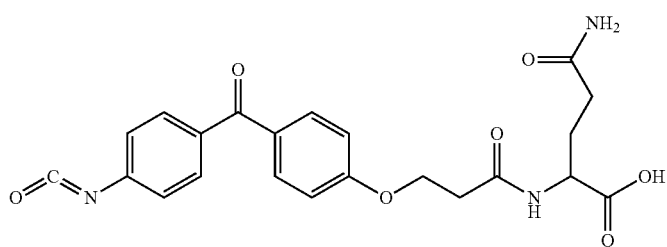

58b 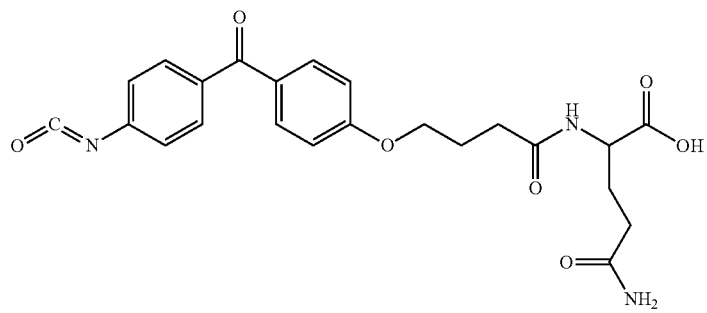
59b 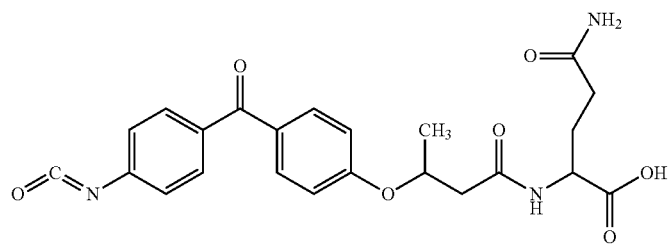
60b 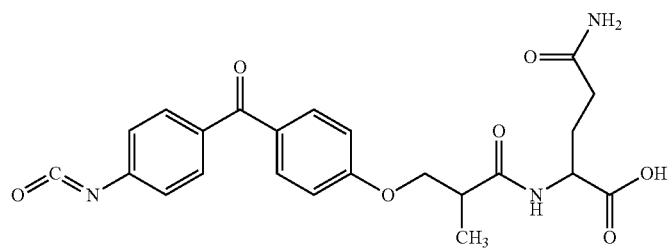
61b 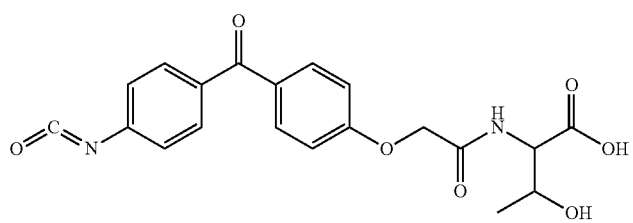 [SMILES: CC(O)C(NC(=O)COc1ccc(C(=O)c2ccc(N=C=O)cc2)cc1)C(=O)O]
62b 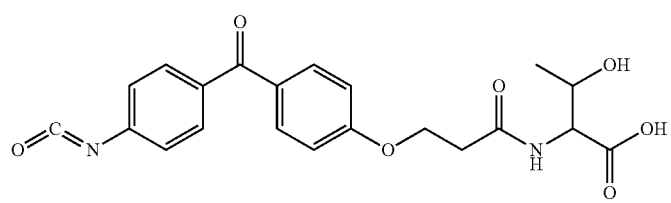 [SMILES: CC(O)C(NC(=O)CCOc1ccc(C(=O)c2ccc(N=C=O)cc2)cc1)C(=O)O]
63b 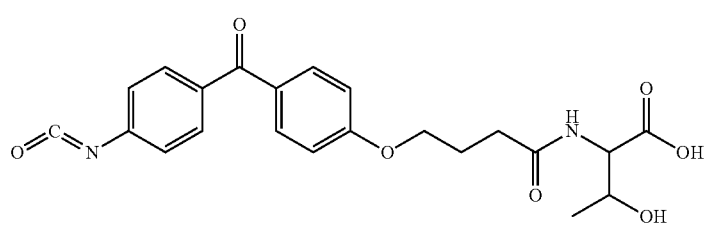 [SMILES: CC(O)C(NC(=O)CCCOc1ccc(C(=O)c2ccc(N=C=O)cc2)cc1)C(=O)O]

64b 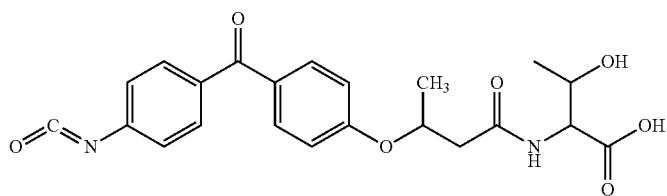 [SMILES: CC(CC(=O)NC(C(=O)O)C(C)O)Oc1ccc(C(=O)c2ccc(N=C=O)cc2)cc1]
65b 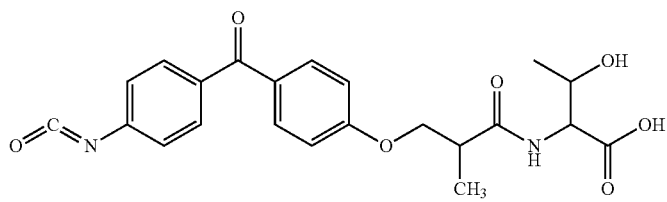 [SMILES: CC(COc1ccc(C(=O)c2ccc(N=C=O)cc2)cc1)C(=O)NC(C(=O)O)C(C)O]
66b 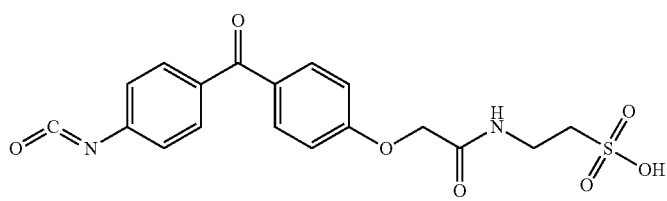 [SMILES: O=C=Nc1ccc(C(=O)c2ccc(OCC(=O)NCCS(=O)(=O)O)cc2)cc1]
67b 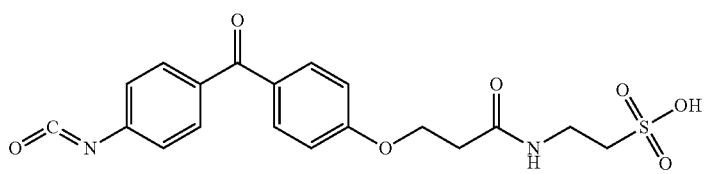 [SMILES: O=C=Nc1ccc(C(=O)c2ccc(OCCC(=O)NCCS(=O)(=O)O)cc2)cc1]
68b 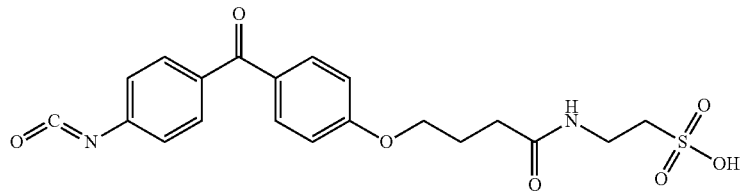 [SMILES: O=C=Nc1ccc(C(=O)c2ccc(OCCCC(=O)NCCS(=O)(=O)O)cc2)cc1]
69b 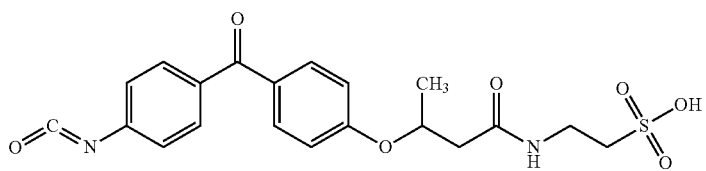 [SMILES: CC(CC(=O)NCCS(=O)(=O)O)Oc1ccc(C(=O)c2ccc(N=C=O)cc2)cc1]
70b 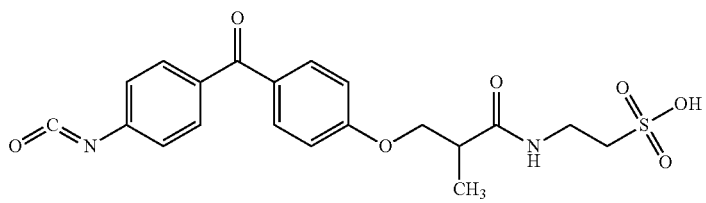 [SMILES: CC(COc1ccc(C(=O)c2ccc(N=C=O)cc2)cc1)C(=O)NCCS(=O)(=O)O]

as well as the pharmaceutically acceptable salts thereof, particularly the sodium salts.

Analogously, by reaction with other bases, such as TRIS (tris(hydroxymethyl)-aminomethane or 2-amino-2-(hydroxymethyl)-propane-1,3-diol), further salts of the example compounds can be obtained.

Therein, particularly the TRIS-salt exhibits a considerably higher water solubility at room temperature than the sodium salt.

Preparation Example

Synthesis of the Compound of Example 2A

The preparation of Example 2A proceeds according to the following schema:

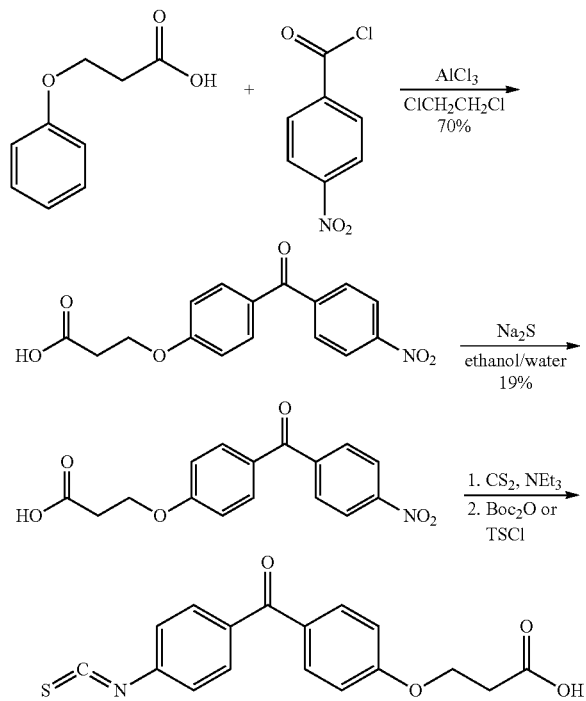

Figure 4:
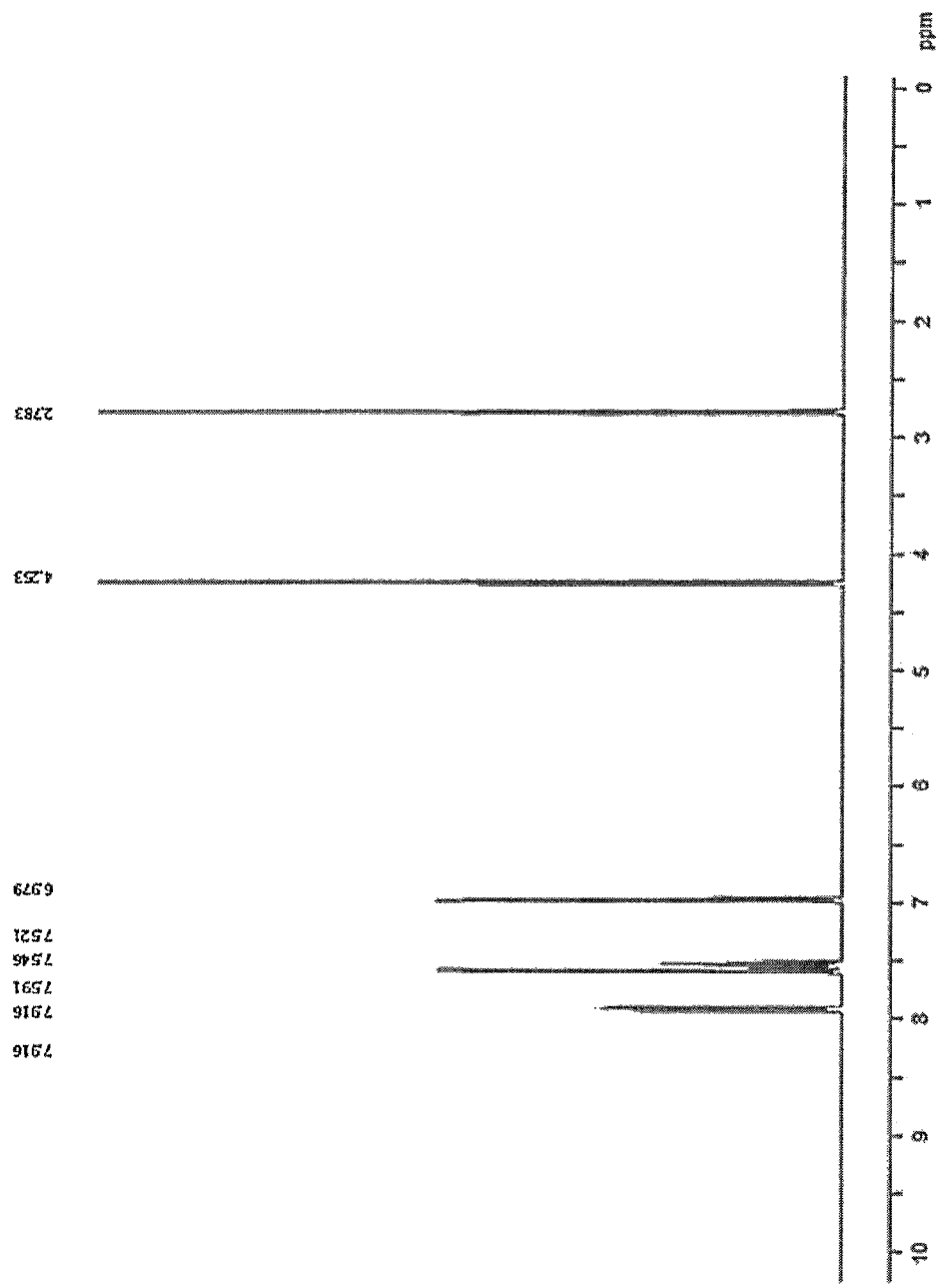

The $^1$H-NMR spectrum is shown in FIG. 4.

The preparation of the other examples proceeds analogously.

Pharmakological Activity Tests:

All the tests were carried out using female nude mice under standard conditions for the keeping of animals with controlled illumination and temperature. The animals were given water and food as desired.

Breast tumors (MAXF 401) were implanted subcutaneously into the rear members of the mice aged 10 weeks. The increase in the volume of the individual tumors was measured using microcallipers, and the size of the tumor was calculated according to the formula a*b$^2$/2 (where a is the largest diameter of the tumor and b is the vertical axis). When the tumor volume had increased to 80-120 mm$^3$, the animals were allocated at random into test groups of in each case 6 animals.

The test compound (in the form of sodium salts) was dissolved in a saline solution, and 5% Klucel (hydroxypropylcellulose) was added in order to dissolve the test compound in the carrier. The compound was administered by intraperitoneal injection. A volume of 10 ml/kg body weight was injected. Animals that received only the carrier served as control. The test compound was treated according to the scheme of twice weekly administration over a period of 5 weeks. The tumor volume and the body weight were checked twice weekly, and the relative tumor volumes were calculated as the ratio of tumor size to body weight. The test was finished when the tumor volume of the control group had reached a size which required the animals to be sacrificed in order to satisfy the regulations relating to animal protection.

On the basis of the relative tumor volumes of the animals treated with the test compound compared with the tumor volumes of the controls treated only with the carrier, the T/C values were calculated and were used as the index of anti-tumor activity. (The T/C index here represents the ratio of the tumor size of treated and untreated animals. The smaller the ratio, the better the activity. 100% would be no activity: tumor is the same size).

Table T/C value and mortality for the test compound of Example 2a.

| Test compound | T/C value | Mortality |
|---|---|---|
| Compound of Example 2a | 1.7 | 0/6 |

Anti-Tumor Activity:

FIG. 1 shows the selectivity of the anti-tumor activity of the compound of Example 2a (sodium salt) on different tumors.

The anti-tumor activity of the substance of Example 2a (sodium salt) was tested in a xenograft tumor panel. Therefore, xenografts of human tumors derived from the mentioned cancers were implanted in nude mice. The implantation and the determination of tumor volumes were carried out as described hereinbefore. Groups of 5 to 8 animals were used. The test compound was administered by ip injection twice weekly in the mentioned doses in the form of the sodium salt as an aqueous solution.

Figure 2:
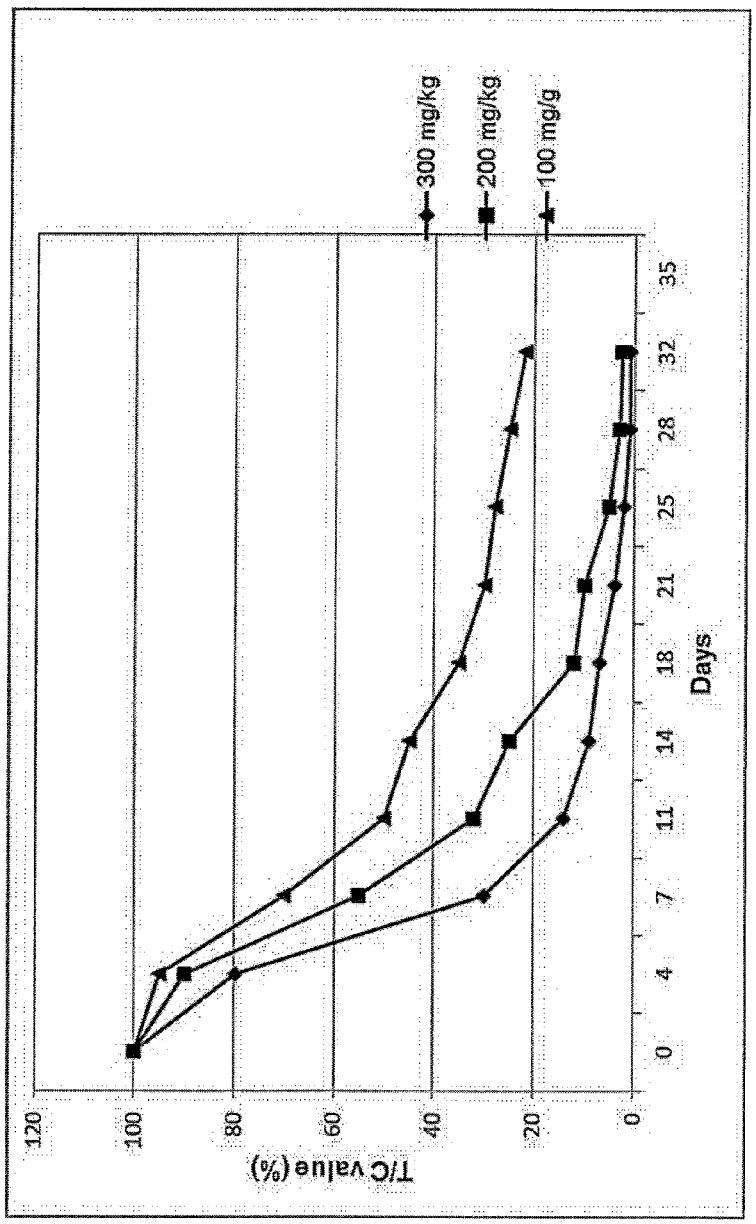
FIG. 2 depicts Dose-dependent anti-tumor activity of the compound of Example 2a (sodium salt) in breast tumors (MAXF 401—Xenograft in nude mice—treatment 2×/week (ip-injection).

FIG. 2 shows the dose dependent anti-tumor activity of the compound of Example 2a (sodium salt) in breast tumors (MAXF 401—xenograft in nude mice).

Therein, the anti-tumor activity of the compound of Example 2a (sodium salt) was examined in the MAXF-401 xenograft tumor model in the nude mouse. Subcutaneous implantation of the tumor and the determination of the tumor volume was carried out as described hereinbefore. The test compound was administered by ip injection twice weekly in the mentioned doses in the form of the sodium salt as an aqueous solution over a period of 4 weeks. The figure shows the dose-dependent progression over time of the anti-tumor activity of the test compound as the T/C value. A dose of 100 mg/kg was determined as the threshold dose, ≥200 mg/kg as the ED90 of the anti-tumor activity. At the dose ≥200 mg/kg, remission of the tumors was observed under therapy. The substance was well tolerated in the dose range used.

Figure 3:
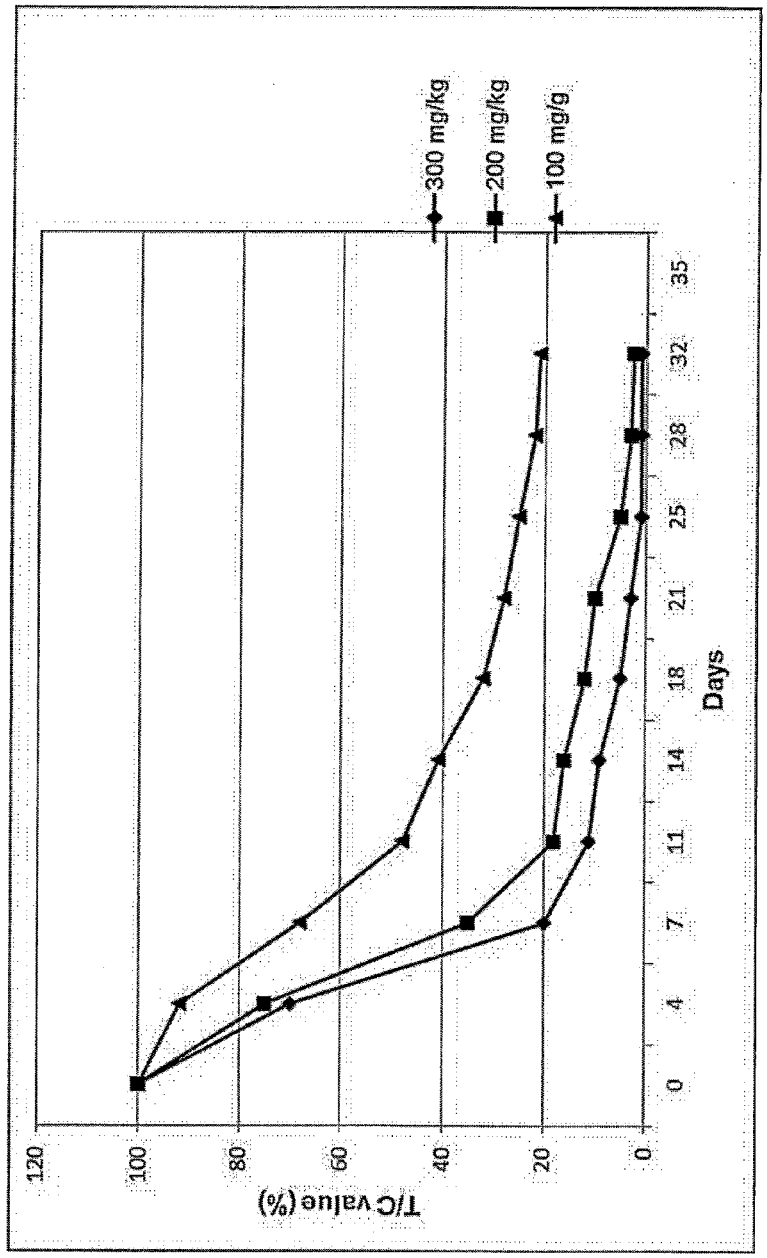
FIG. 3 depicts Dose-dependent anti-tumor activity of the compound of Example 2a (sodium salt) in a colon carcinoma Xenograft model (CXF 280—treatment 2×/week (ip-injection).

FIG. 3 shows the dose-dependency of the anti-tumor activity of the compound of Example 2a (sodium salt) in a colon carcinoma xenograft model (CXF 280—xenograft in nude mice).

The anti-tumor activity of the compound of Example 2a was thereby determined in the CXF280 xenograft tumor model in the nude mouse. Subcutaneous implantation of the tumor and the determination of tumor volumes were carried out as described hereinbefore. The test substance was administered by ip injection twice weekly in the mentioned doses in the form of the sodium salt as an aqueous solution, over a period of 4 weeks. Groups of in each case 8 animals were used. After administration in doses of 100, 200 or 300 mg/kg of Example 2a, a pronounced anti-tumor action was observed in all the doses used, with complete inhibition of tumor growth and the induction of remissions to obliteration of the tumor in the dose group of 200 mg/kg and 300 mg/kg.

ED90 doses were found at doses of 200 mg/kg. The compound was well tolerated in the dose range used and was not associated with a significant weight loss in the animals.

In summary, the compounds according to the invention, or the pharmaceutical compositions thereof, are found to be potent anti-tumor medicaments having improved therapeutic breadth and fewer side-effects.

TABLE

| Composition | Acute single-cell necrosis | Focal tubular necrosis |
|---|---|---|
| Control | 0/6 | 0/6 |
| Test compound, Example 2a | 0/9 | 0/9 |

No necrotic changes were found in the kidneys of the animals treated with the compound according to the invention. This confirms the excellent tolerability profile of the compounds according to the invention.

The invention claimed is:
1. Compounds of the formula (1):

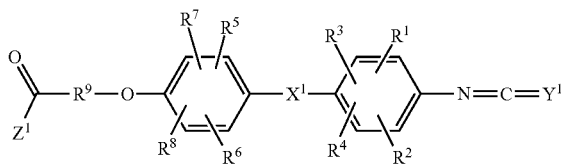

(2)

wherein
$Y^1$=S or O and wherein
$R^1, R^2, R^3, R^4, R^5, R^6, R^7$ and $R^8$ are identical or different and are in each case selected from the group consisting of:
hydrogen,
hydroxy,
halogen,
cyano,
nitro,
carboxyl,
aminocarbonyl,
sulfonic acid radical (—SO3H),
aminosulfonyl,
optionally substituted alkyl,
optionally substituted alkoxy,
optionally substituted alkenyl,
optionally substituted aryl,
optionally substituted alkylaryl;
$R^9$ is optionally substituted linear, branched or cyclic alkanediyl, optionally substituted linear, branched or cyclic alkenediyl, aryl or heterocyclyl;
$Z^1$ is selected from
hydroxy (—OH) or
a radical of the formula —N—$R^{10}R^{11}$, wherein
$R^{10}$ is hydrogen and $R^{11}$ is optionally substituted alkyl or hydroxyl, or
$R^{11}$ is hydrogen and $R^{10}$ optionally substituted alkyl or hydroxyl, or $R^{10}$ and $R^{11}$ are each alkyl, wherein at least one of the alkyl groups has at least one substituent, or
$R^{10}$ and $R^{11}$, together with the nitrogen atom to which they are bonded, form a saturated or unsaturated, optionally substituted 5- to 8-membered ring which can optionally contain further heteroatoms; and wherein
$X^1$ is selected from the group consisting of:
a single bond,
carbonyl,
sulfur,
oxygen,
sulfoxy,
sulfonyl,
azo and
an optionally substituted, saturated or unsaturated aliphatic radical having from 1 to 6 carbon atoms,
or pharmaceutically acceptable salts thereof.
2. The compounds according to claim 1, wherein $Z^1$ is hydroxy.
3. The compounds according to claim 1, wherein $Z^1$ is a radical of the formula —N—$R^{10}R^{11}$, wherein
$R^{10}$ is hydrogen and $R^{11}$ is substituted alkyl, or
$R^{11}$ is hydrogen and $R^{10}$ is substituted alkyl.
4. The compounds according to claim 3, wherein
substituted alkyl, is an alkyl group, which comprises at least one group of the formula —$X^2$—$R^{12}$, wherein $X^2$ is selected from the group consisting of:
carbonyl,
sulfoxy, and
sulfonyl, and
$R^{12}$ is selected from the group consisting of:
hydroxy,
optionally substituted amino, and
optionally substituted alkoxy.
5. The compounds according to claim 1, wherein
$R^{10}$ is hydrogen and $R^{11}$ is a radical A of a compound of the formula $H_2$N-A, or
$R^{11}$ is hydrogen and $R^{10}$ is a radical A of a compound of the formula $H_2$N-A, wherein
A is a radical that is derived by cleavage of the amino group (—$NH_2$) from a natural or synthetic amino acid, a natural or synthetic amino acid derivative or a polyamino acid or polyamino acid derivative.
6. The compounds according to claim 1, wherein
$Y^1$=S or O,
$R^1, R^2, R^3, R^4, R^5, R^6, R^7$ and $R^8$ are in each case hydrogen,
$R^9$ is linear, branched or cyclic alkanediyl,
$Z^1$ is hydroxy or a radical of the formula —N—$R^{10}R^{11}$, wherein
$R^{10}$ is hydrogen and $R^{11}$ is a radical A of a compound of the formula $H_2$N-A or
$R^{11}$ is hydrogen and $R^{19}$ is a radical A of a compound of the formula $H_2$N-A,
wherein
A is in each case a radical that is derived by cleavage of the amino group (—$NH_2$) from a natural or synthetic amino acid, a natural or synthetic amino acid derivative or a polyamino acid or polyamino acid derivative, and
$X^1$ is carbonyl (—CO—).
7. The compounds according to claim 1, wherein
$Y^1$=S or O,
$R^1, R^2, R^3, R^4, R^5, R^6, R^7$ and $R^8$ are in each case hydrogen,
$R^9$ is linear, branched or cyclic alkanediyl,
$Z^1$ is hydroxy, and $X^1$ is carbonyl (—CO—).
8. The compounds according to claim 1, selected from the group consisting of:
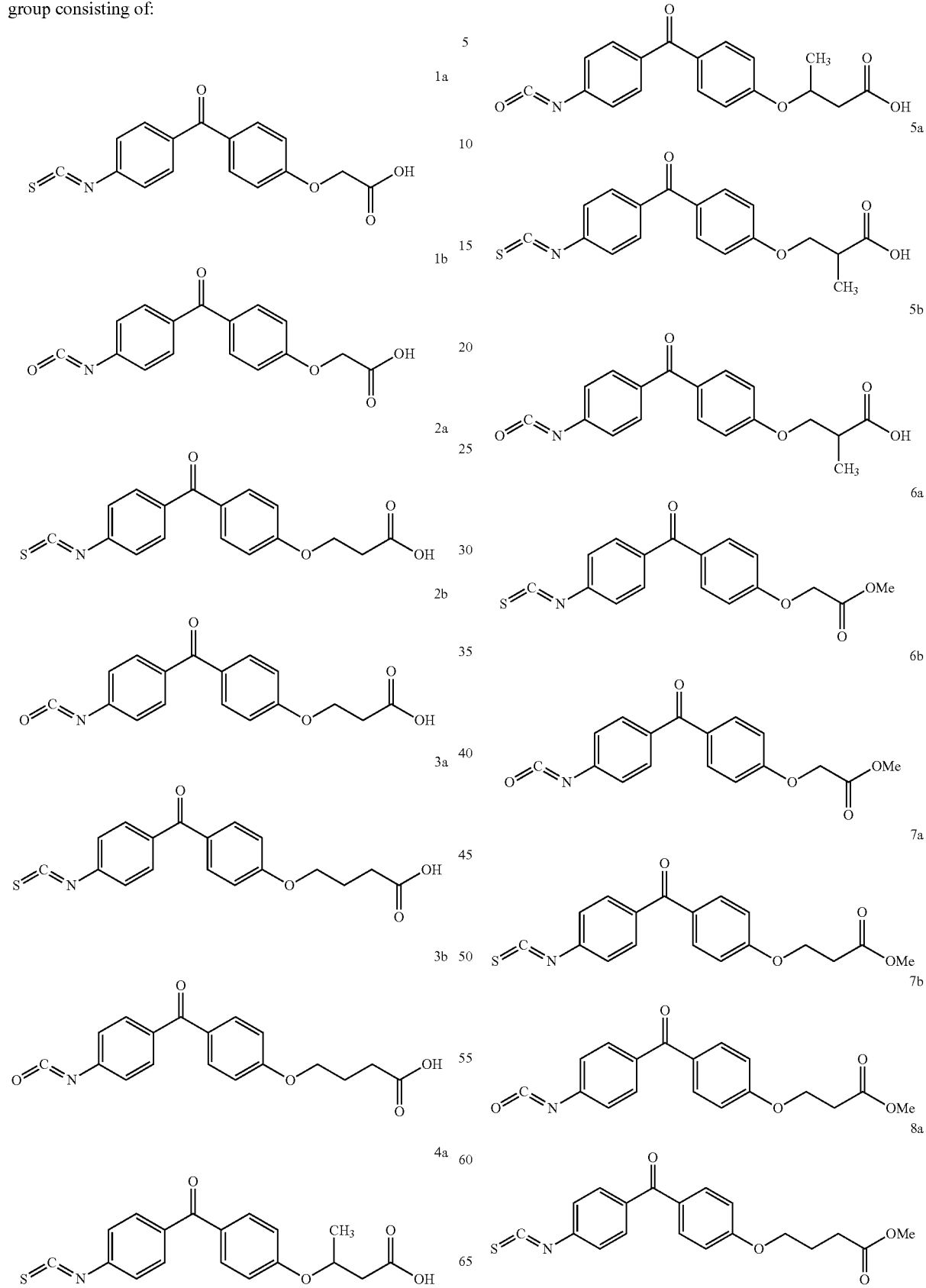

8b
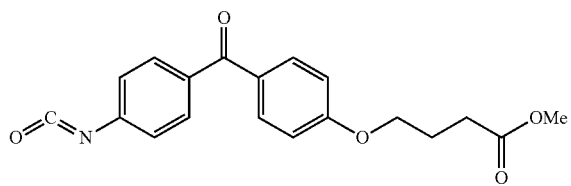
9a
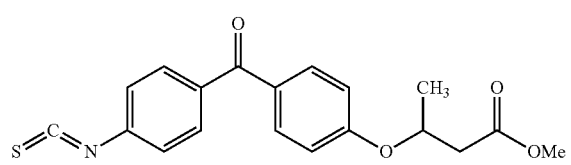
9b
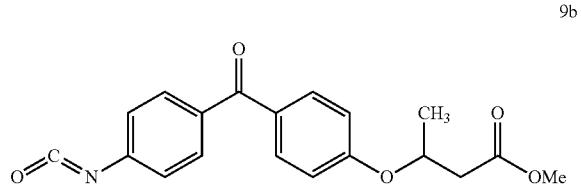
10a
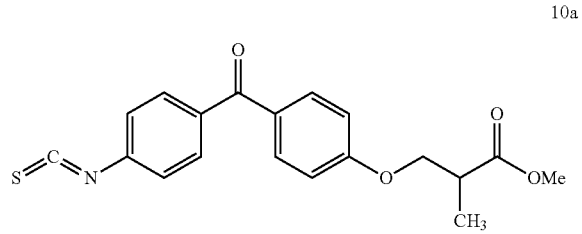
10b
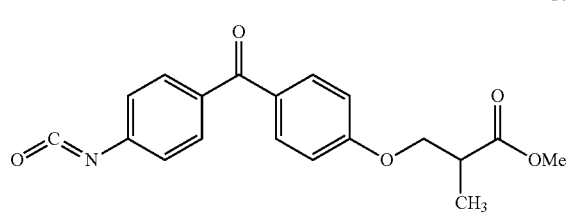
11a
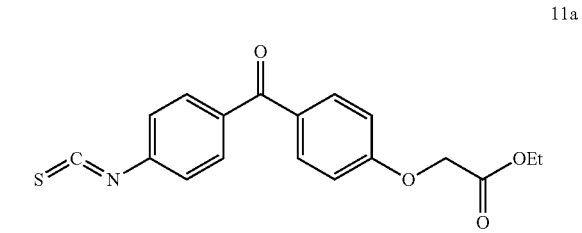
11b
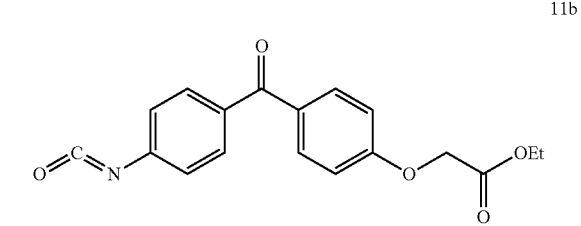
12a
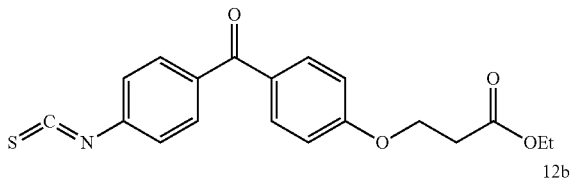
12b
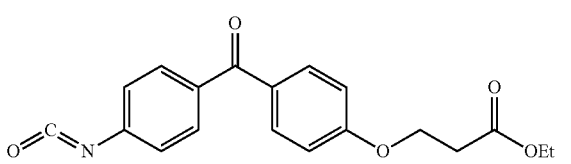
13a
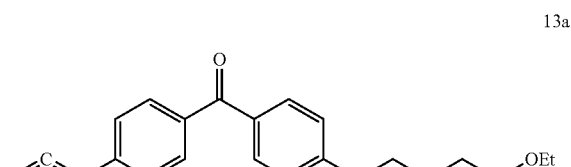
13b
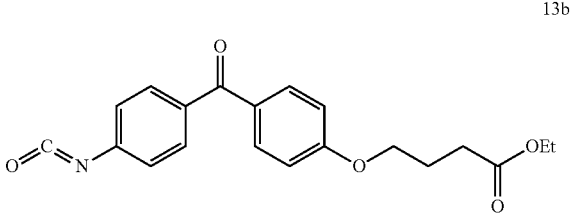
14a
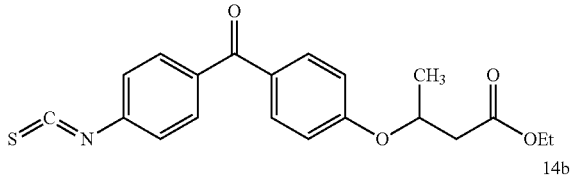
14b
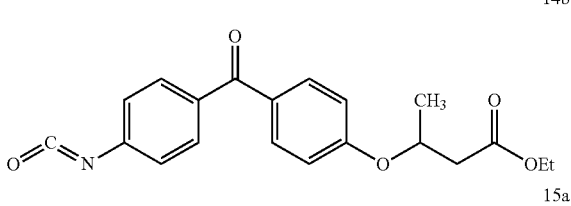
15a
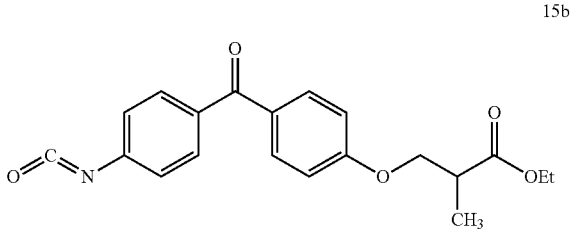
15b 16a 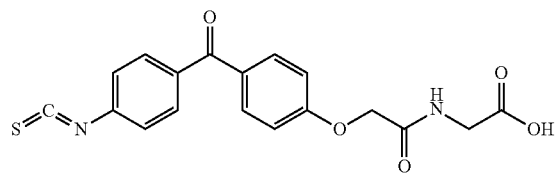
16b 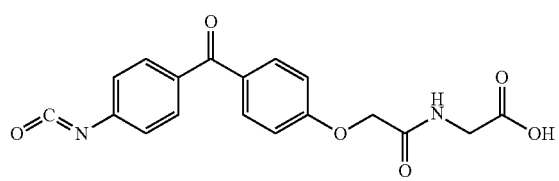
17a 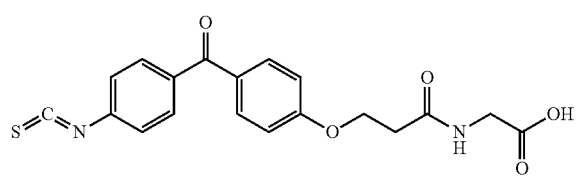
17b 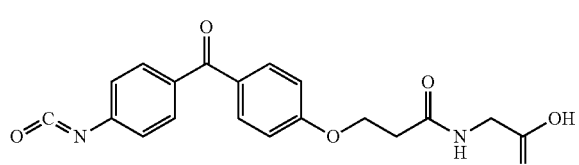
18a 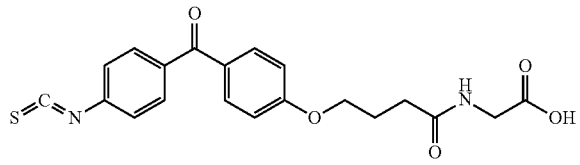
18b 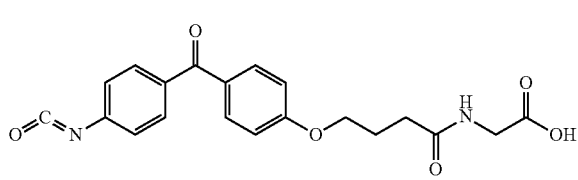
19a 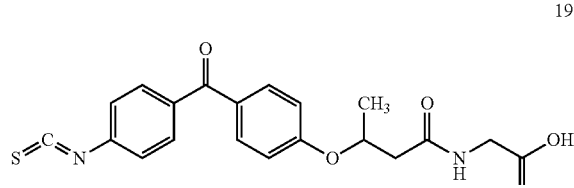
19b 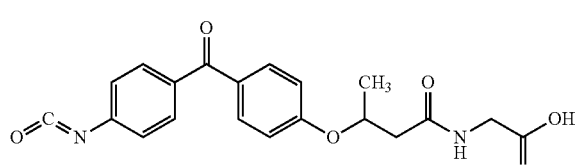
20a 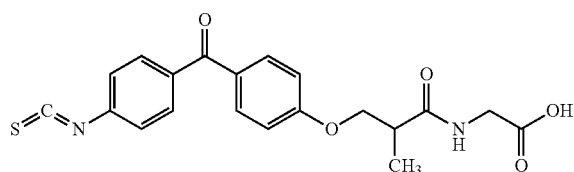
20b 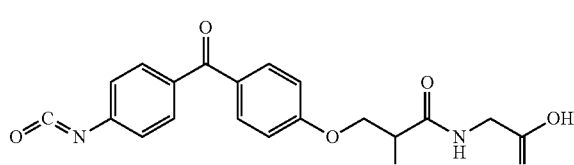
21a 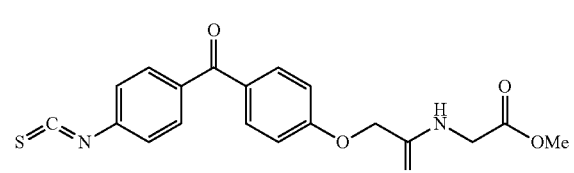
21b 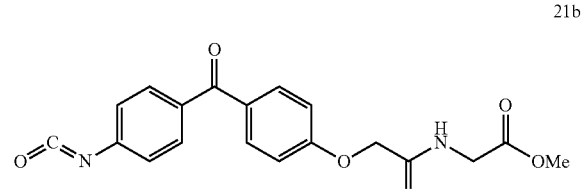
22a 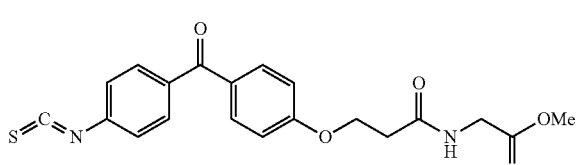
22b 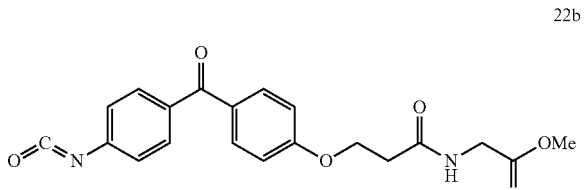
23a 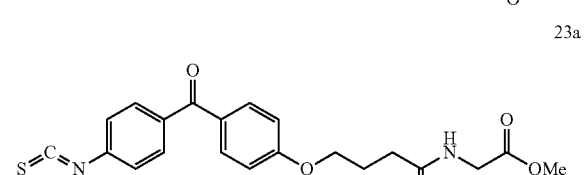
23b 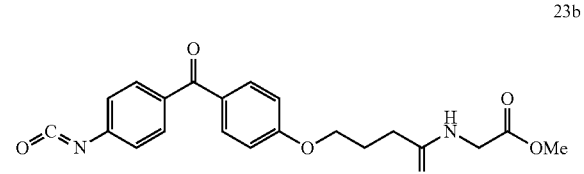

-continued

32a
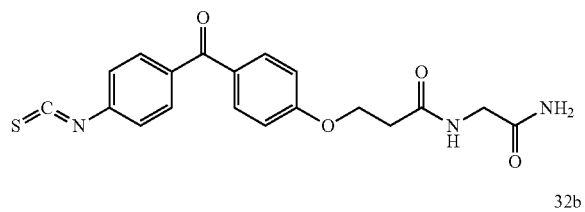
32b
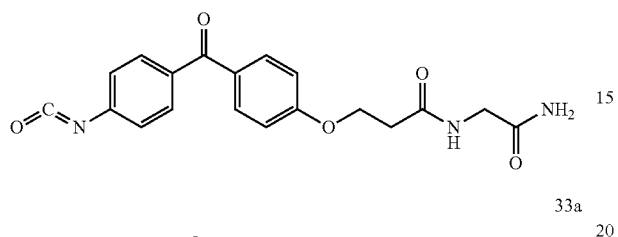
33a
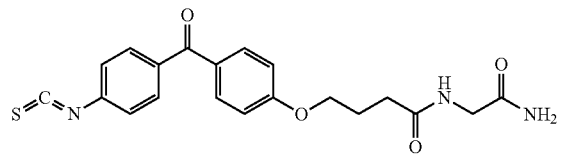
33b
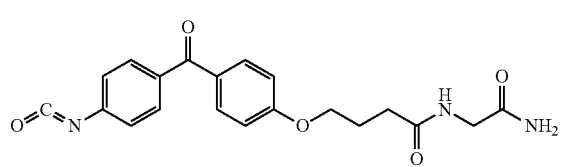
34a
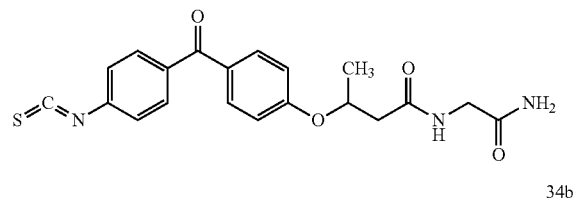
34b
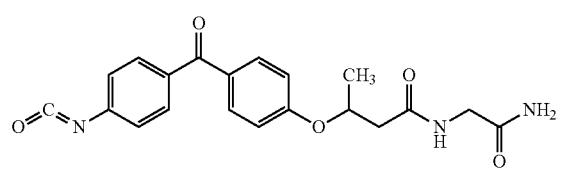
35a
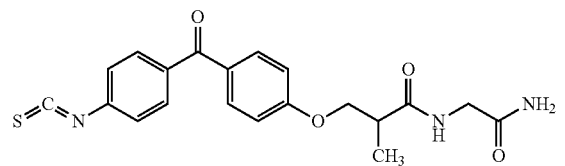
35b
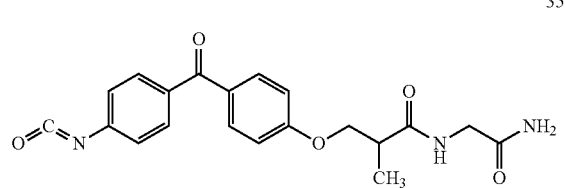
36a
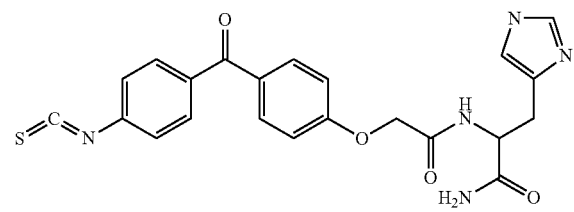
36b
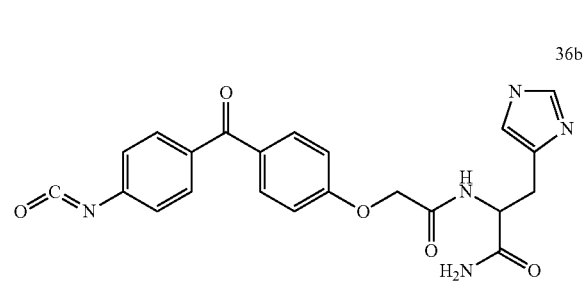
37a
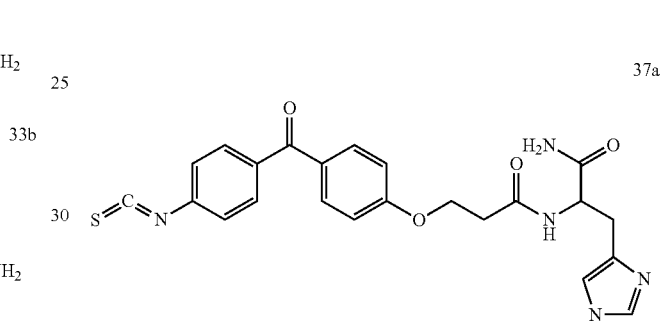
37b
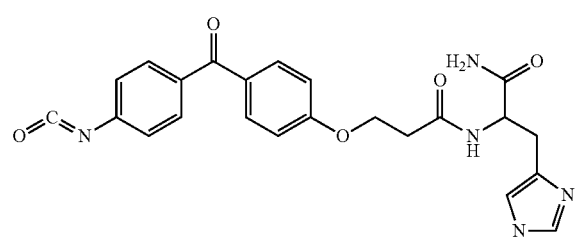
38a
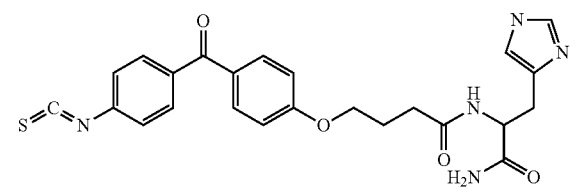
38b
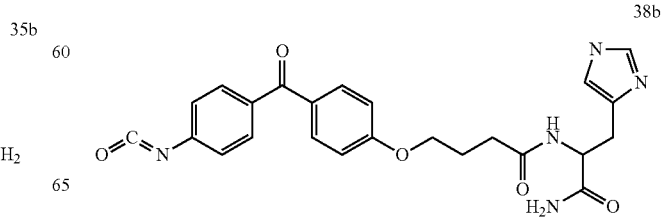

39a
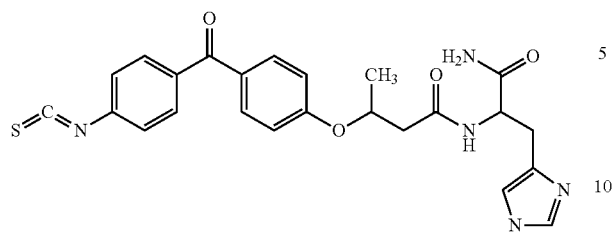
39b
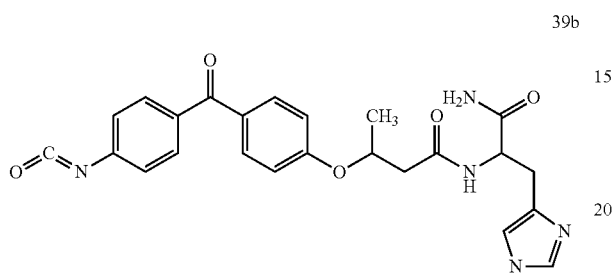
40a
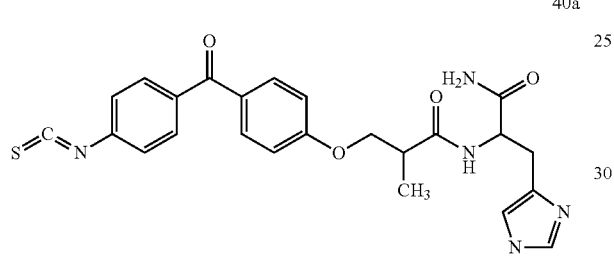
40b
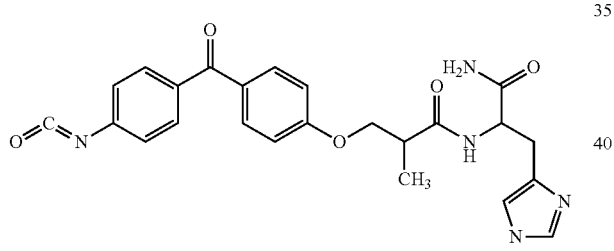
41a
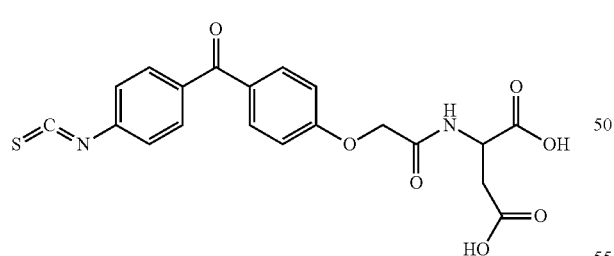
41b
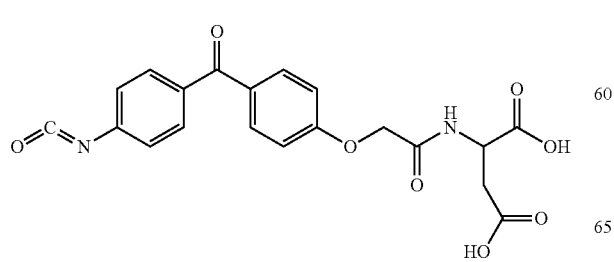
42a
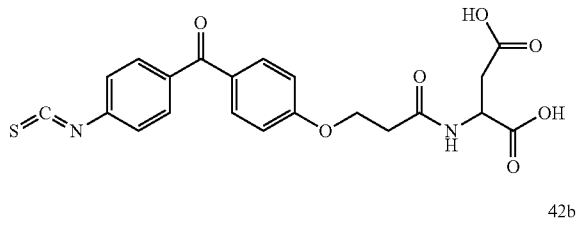
42b
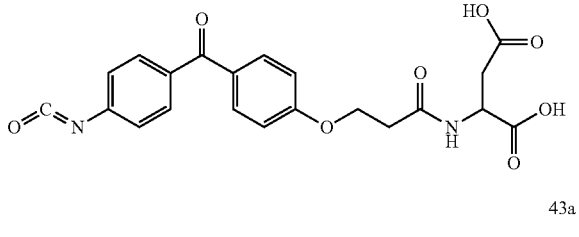
43a
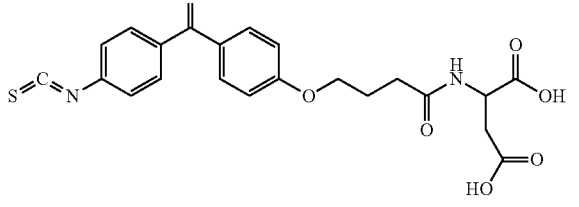
43b
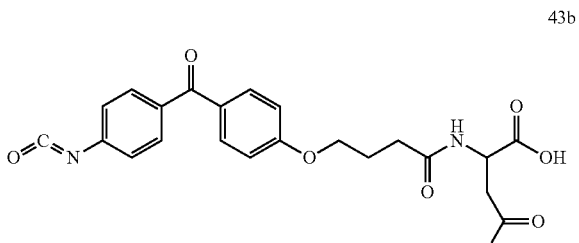
44a
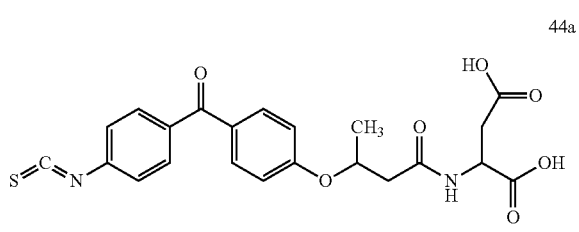
44b
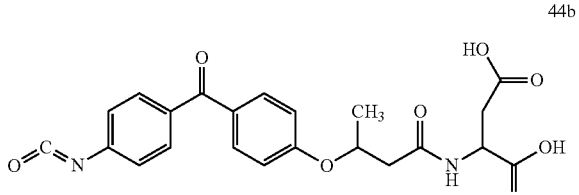
45a
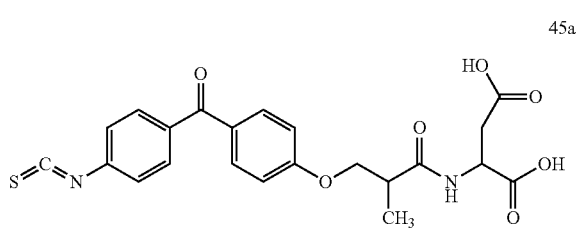

45b
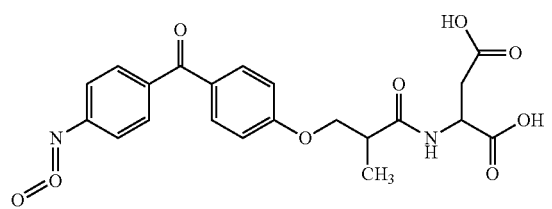
48b
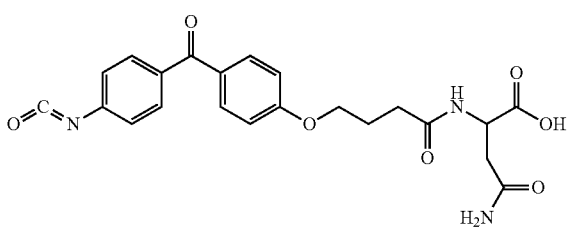
46a
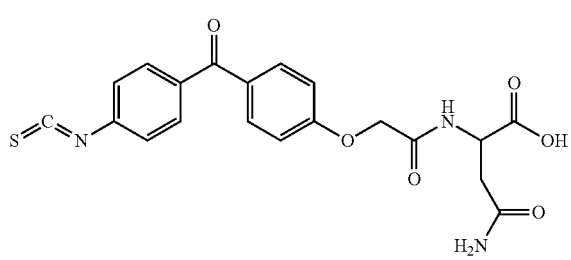
49a
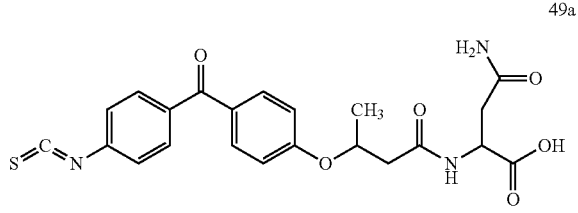
46b
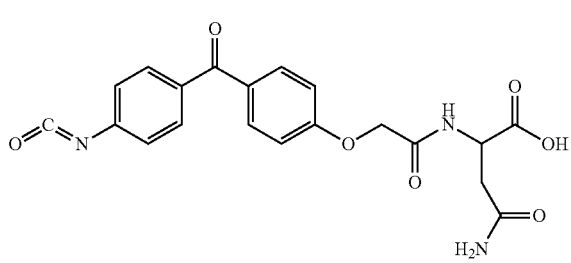
49b
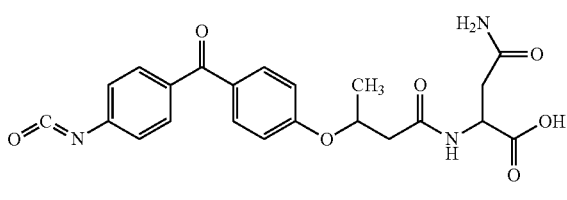
47a
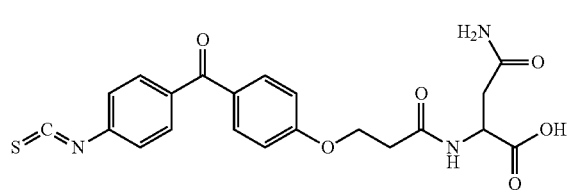
50a
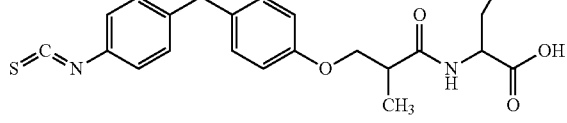
47b
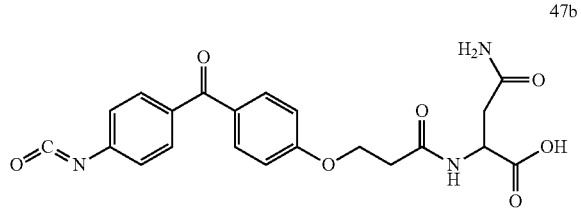
50b
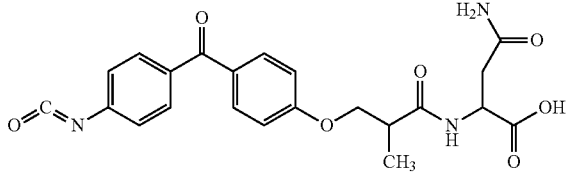
48a
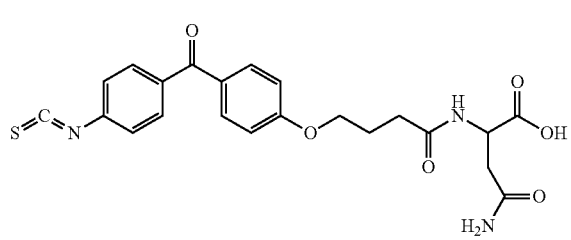
51a
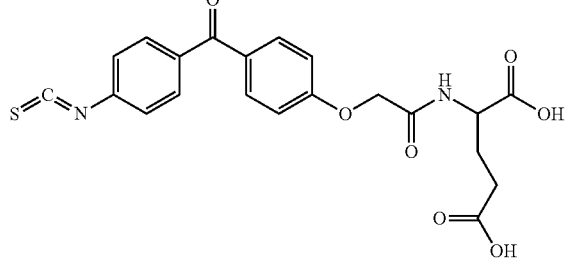

51b
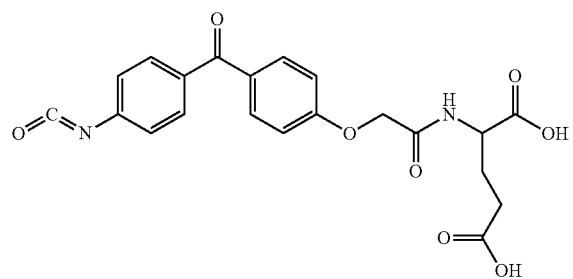
52a
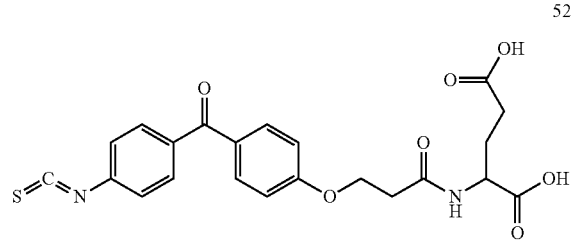
52b
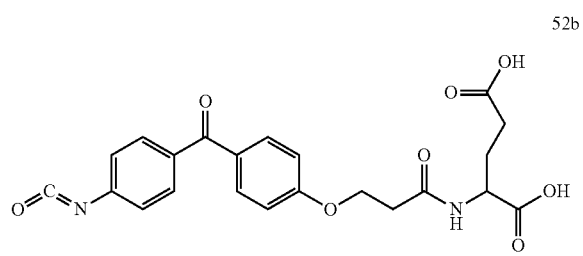
53a
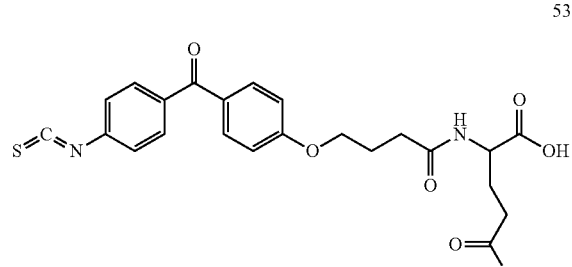
53b
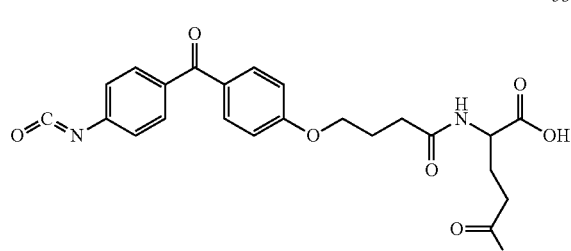
54a
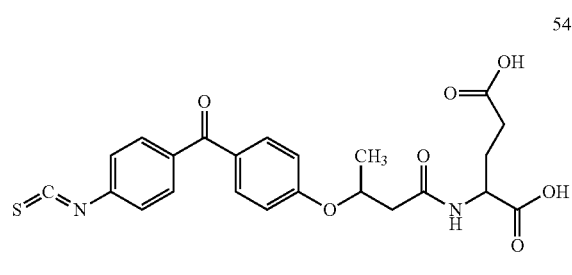
54b
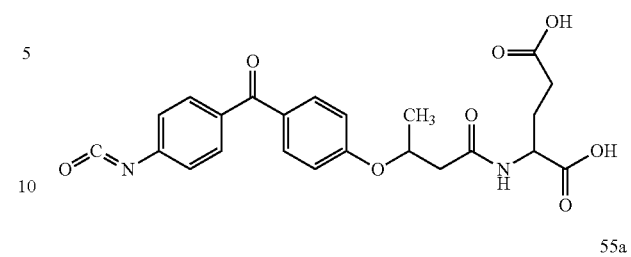
55a
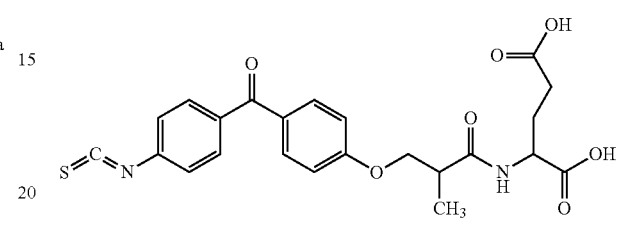
55b
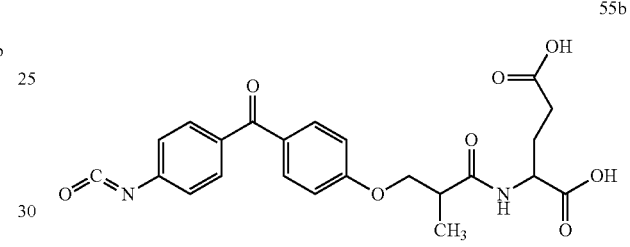
56a
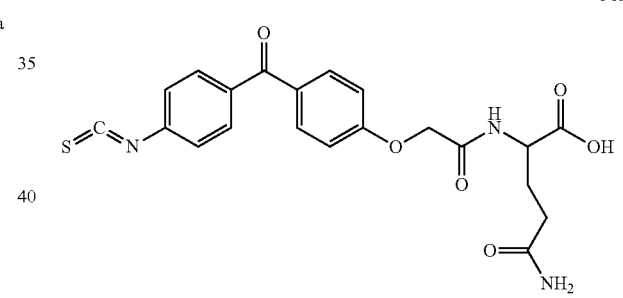
56b
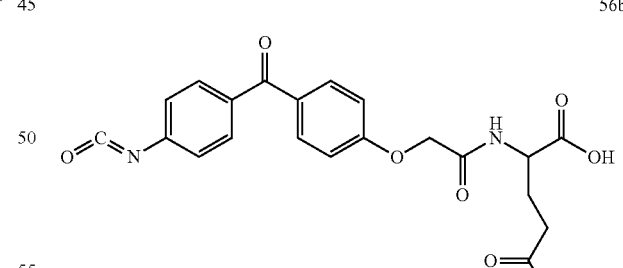
57a
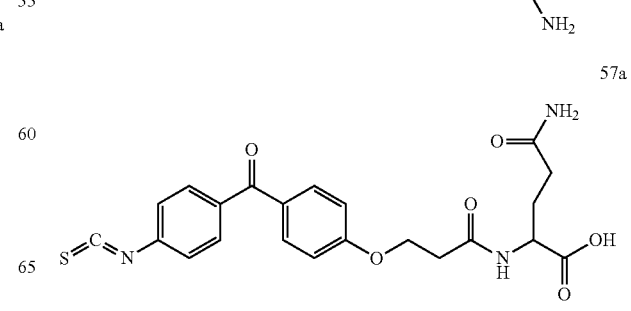

81 -continued
57b
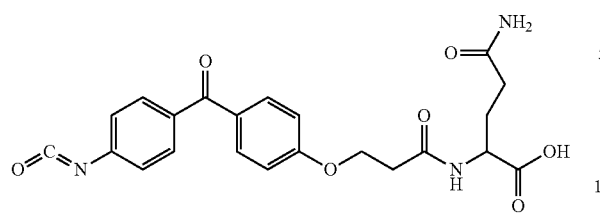
58a
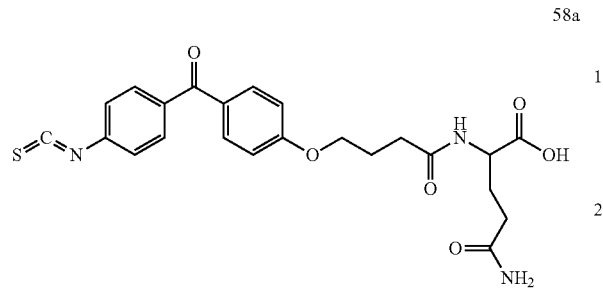
58b
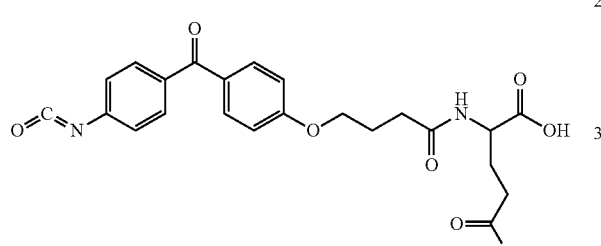
59a
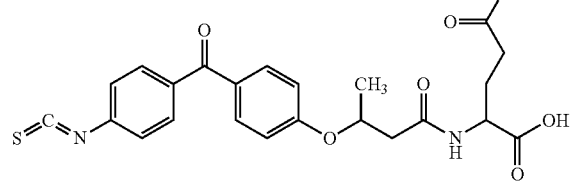
59b
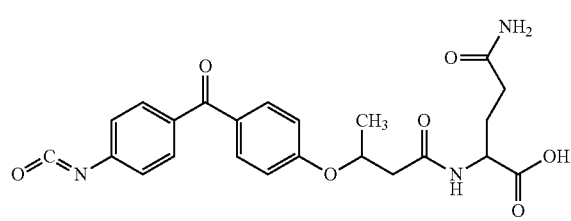
60a
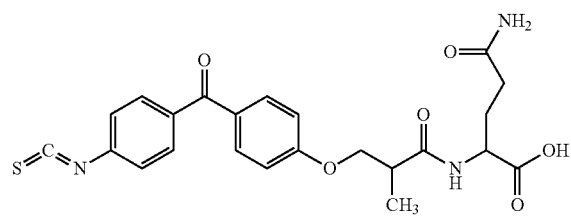
82 -continued
60b
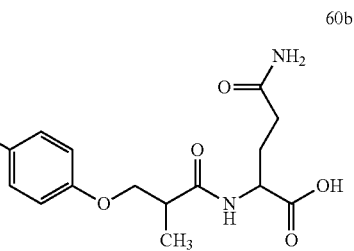
61a
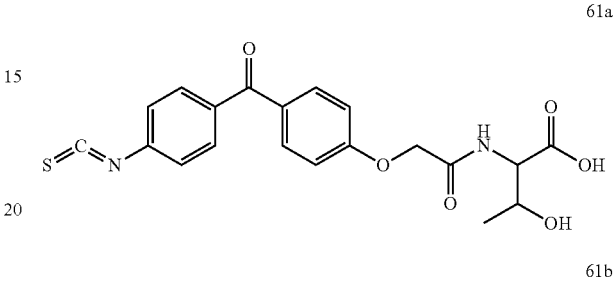
61b
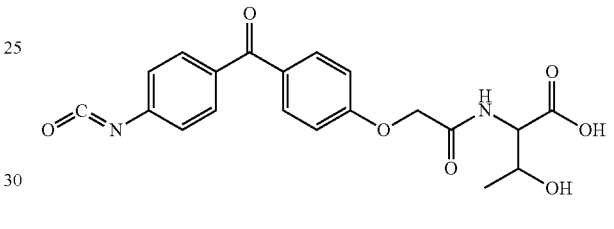
62a
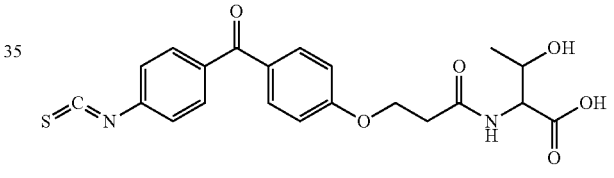
62b
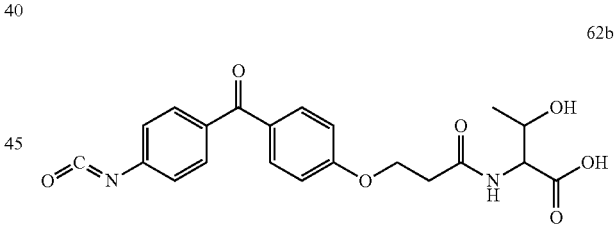
63a
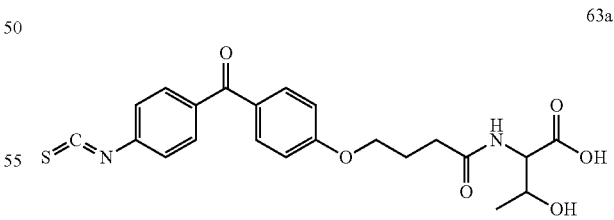
63b
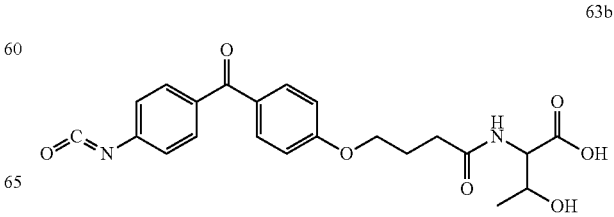

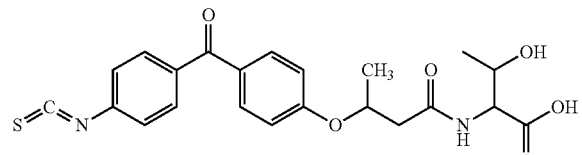
64a

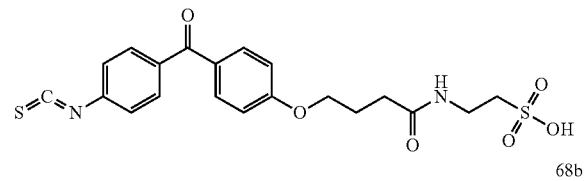
68a

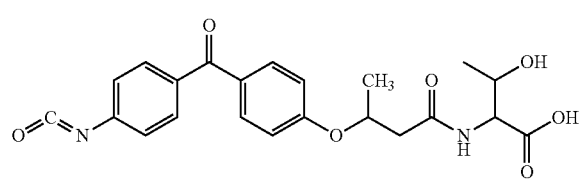
64b

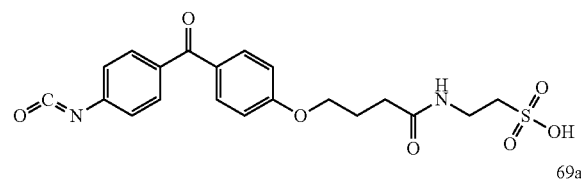
68b

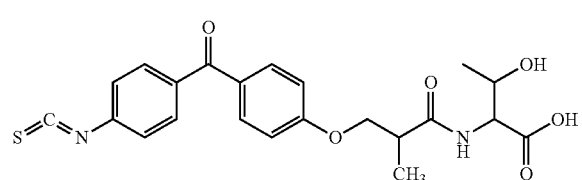
65a

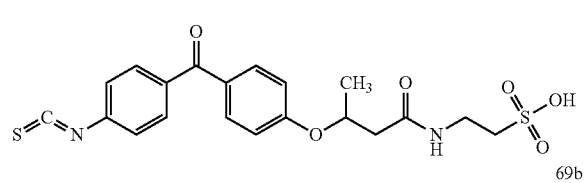
69a

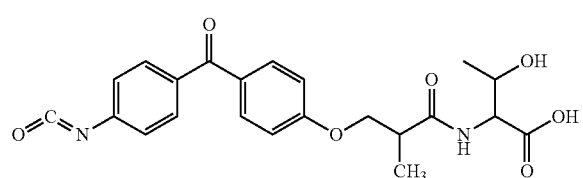
65b

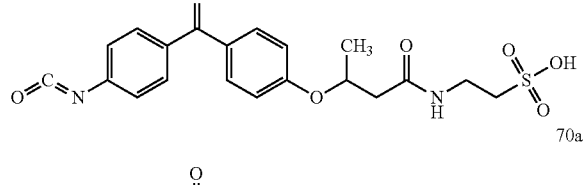
69b

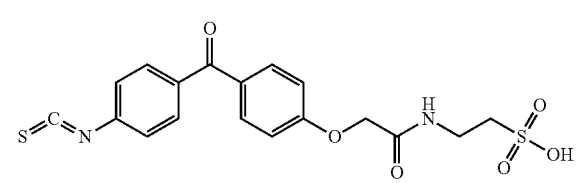
66a

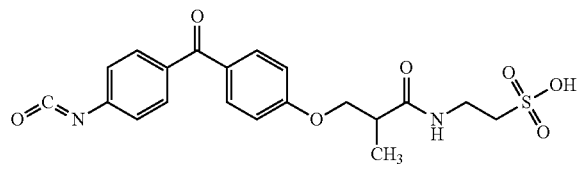
70a

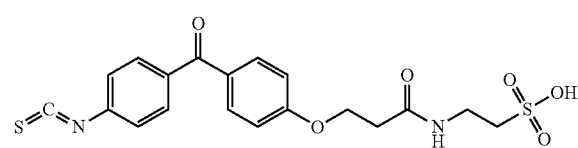
66b

70b

67a

67b or pharmaceutically acceptable salts of any of the foregoing.

9. A medicament comprising one or more of the compounds according to claim 1 and least one selected from the group consisting of an excipient, a binder, a disintegrator, a glidant, a lubricant, a preservative, a stabilizer, a suspending agent, a dispersing agent and a diluent.

10. A method of treating cancer, comprising administering to a patient in need thereof, compounds of the formula (1):

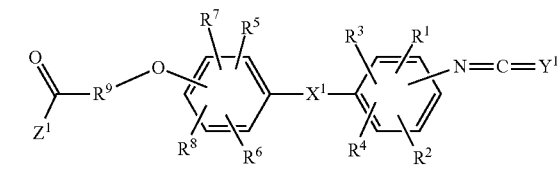

(1)

wherein $Y^1$=S or O and wherein $R^1$, $R^2$, $R^3$, $R^4$, $R^5$, $R^6$, $R^7$ and $R^8$ are identical or different and are in each case selected from the group consisting of:
hydrogen,
hydroxy,
halogen,
cyano,
nitro,
carboxyl,
aminocarbonyl,
sulfonic acid radical (—SO3H),
aminosulfonyl,
optionally substituted alkyl,
optionally substituted alkoxy,
optionally substituted alkenyl,
optionally substituted aryl,
optionally substituted alkylaryl;

$R^9$ is optionally substituted linear, branched or cyclic alkanediyl, optionally substituted linear, branched or cyclic alkenediyl, aryl or heterocyclyl;

$Z^1$ is selected from
hydroxy (—OH) or
a radical of the formula —N—$R^{10}R^{11}$, wherein
$R^{10}$ is hydrogen and $R^{11}$ is optionally substituted alkyl or hydroxyl, or
$R^{11}$ is hydrogen and $R^{10}$ optionally substituted alkyl or hydroxyl, or
$R^{10}$ and $R^{11}$ are each alkyl, wherein at least one of the alkyl groups has at least one substituent, or
$R^{10}$ and $R^{11}$, together with the nitrogen atom to which they are bonded, form a saturated or unsaturated, optionally substituted 5- to 8-membered ring which can optionally contain further heteroatoms; and wherein $X^1$ is selected from the group consisting of:
a single bond,
carbonyl,
sulfur,
oxygen,
sulfoxy,
sulfonyl,
azo and
an optionally substituted, saturated or unsaturated aliphatic radical having from 1 to 6 carbon atoms,
or pharmaceutically acceptable salts thereof.

11. The method of claim 10, wherein $Z^1$ is hydroxy.

12. The method of claim 10, wherein $Z^1$ is a radical of the formula —N—$R^{10}R^{11}$, wherein
$R^{10}$ is hydrogen and $R^{11}$ is substituted alkyl, or
$R^{11}$ is hydrogen and $R^{10}$ is substituted alkyl.

13. The method of claim 12, wherein
substituted alkyl, is an alkyl group, which comprises at least one group of the formula —$X^2$—$R^{12}$, wherein $X^2$ is selected from the group consisting of:
carbonyl,
sulfoxy, and
sulfonyl, and $R^{12}$ is selected from the group consisting of:
hydroxy,
optionally substituted amino, and
optionally substituted alkoxy.

14. The method of claim 10, wherein
$R^{10}$ is hydrogen and $R^{11}$ is a radical A of a compound of the formula $H_2$N-A, or
$R^{11}$ is hydrogen and $R^{10}$ is a radical A of a compound of the formula $H_2$N-A, wherein
A is a radical that is derived by cleavage of the amino group (—$NH_2$) from a natural or synthetic amino acid, a natural or synthetic amino acid derivative or a polyamino acid or polyamino acid derivative.

15. The method of claim 10, wherein the compounds have formula (2):

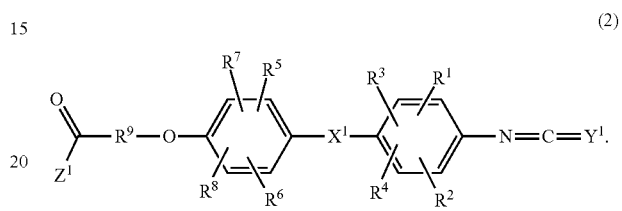

(2)

16. The method of claim 10, wherein
$Y^1$=S or O,
$R^1$, $R^2$, $R^3$, $R^4$, $R^5$, $R^6$, $R^7$ and $R^8$ are in each case hydrogen,
$R^9$ is linear, branched or cyclic alkanediyl,
$Z^1$ is hydroxy or a radical of the formula wherein
$R^{10}$ is hydrogen and $R^{11}$ is a radical A of a compound of the formula $H_2$N-A or
$R^{11}$ is hydrogen and $R^{10}$ is a radical A of a compound of the formula $H_2$N-A, wherein
A is in each case a radical that is derived by cleavage of the amino group (—$NH_2$) from a natural or synthetic amino acid, a natural or synthetic amino acid derivative or a polyamino acid or polyamino acid derivative, and
$X^1$ is carbonyl (—CO—).

17. The method of claim 10, wherein
$Y^1$=S or O,
$R^1$, $R^2$, $R^3$, $R^4$, $R^5$, $R^6$, $R^7$ and $R^8$ are in each case hydrogen,
$R^9$ is linear, branched or cyclic alkanediyl,
$Z^1$ is hydroxy, and
$X^1$ is carbonyl (—CO—).

18. The method of claim 10, wherein the compounds are selected from the group consisting of:

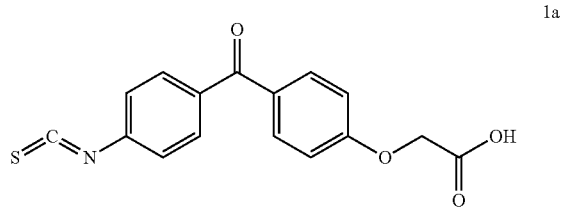

1a

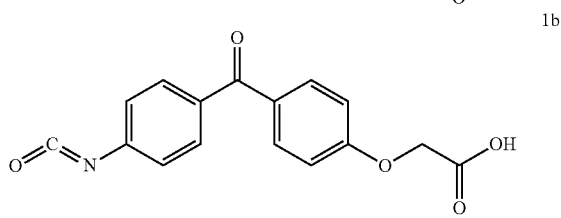

1b

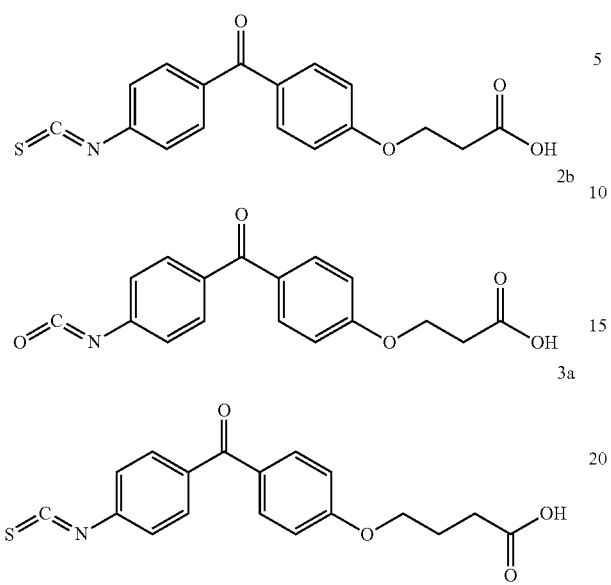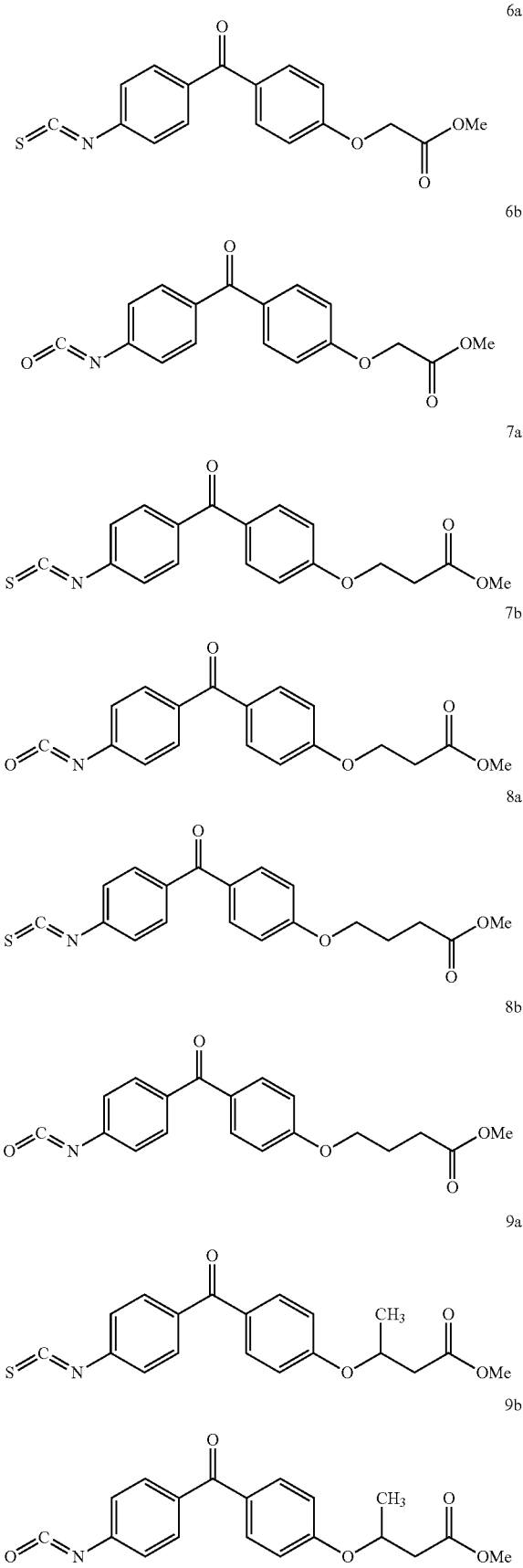

-continued
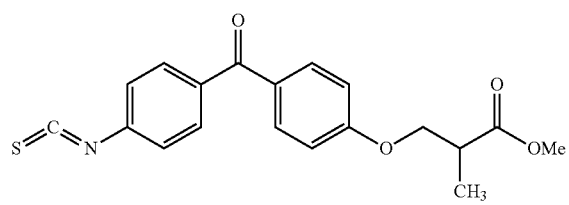
10a
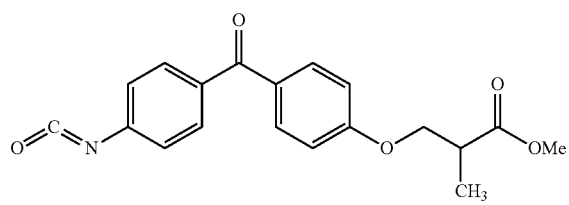
10b
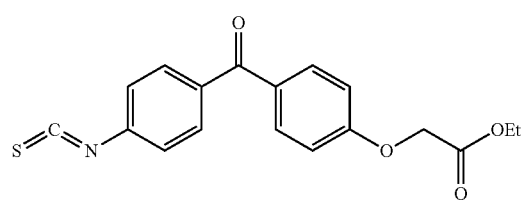
11a
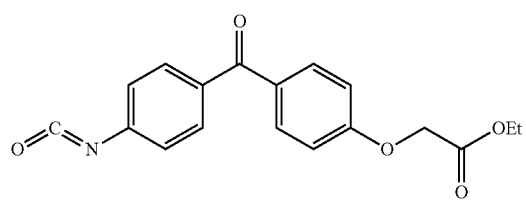
11b
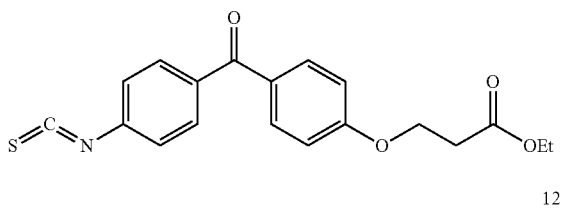
12a
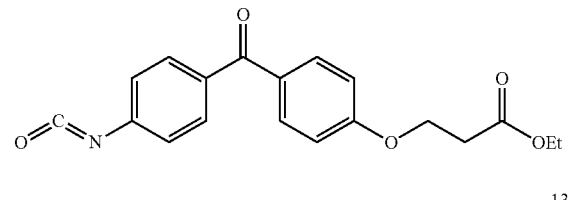
12b
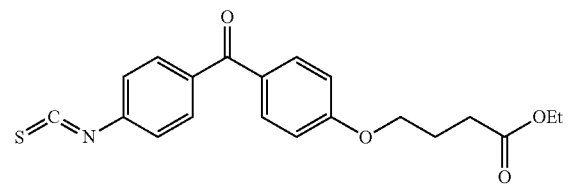
13a
-continued
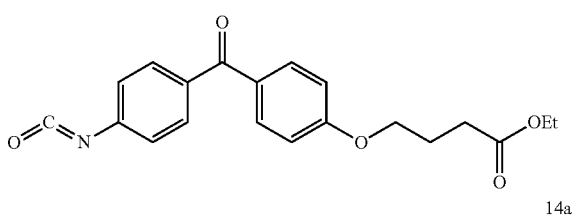
13b
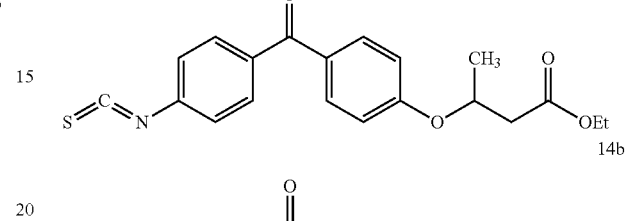
14a
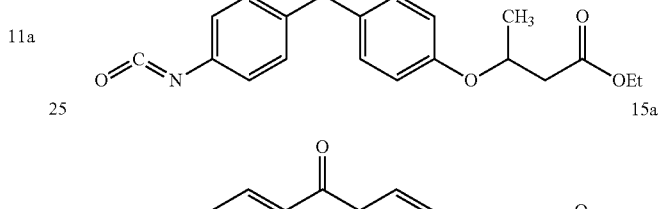
14b
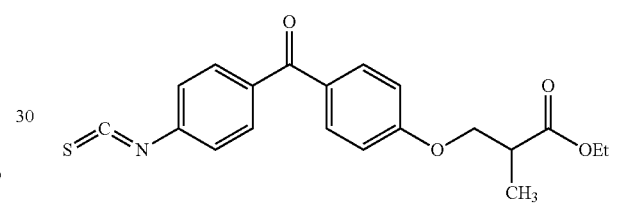
15a
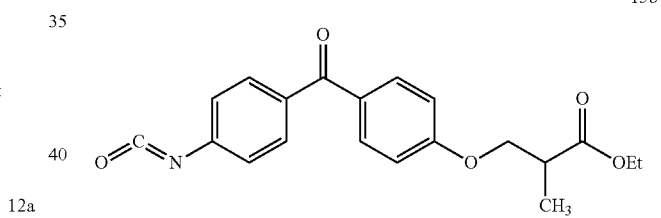
15b
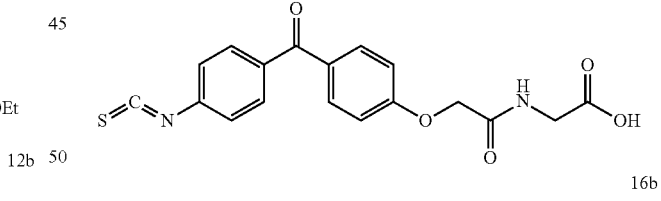
16a
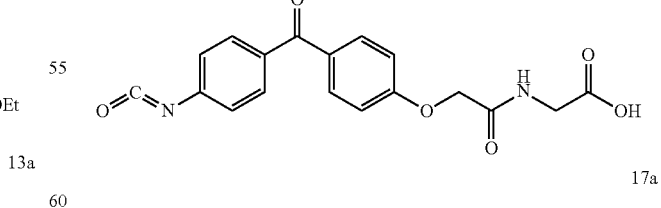
16b
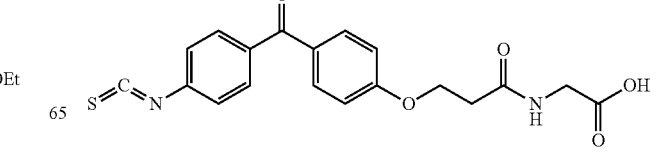
17a 17b
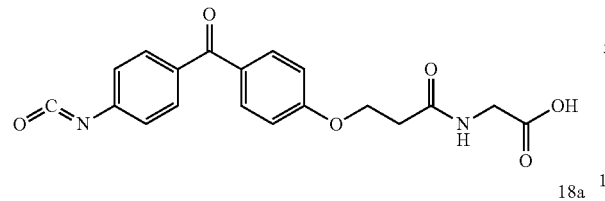
18a
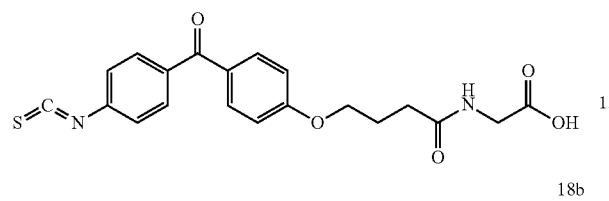
18b
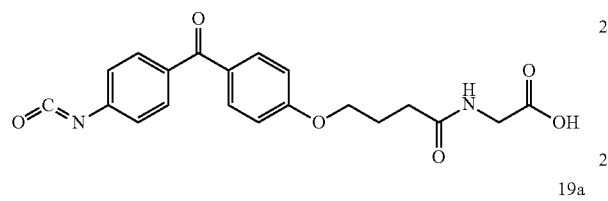
19a
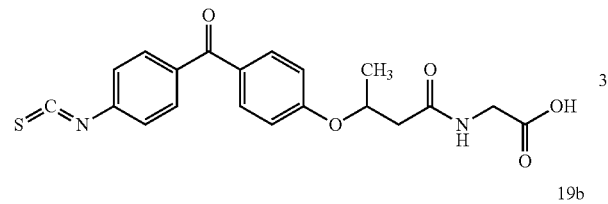
19b
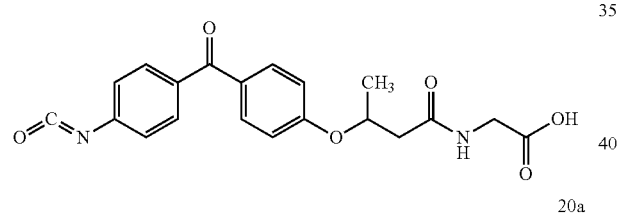
20a
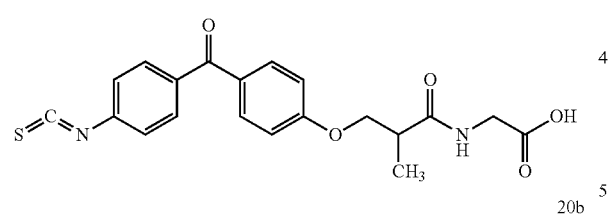
20b
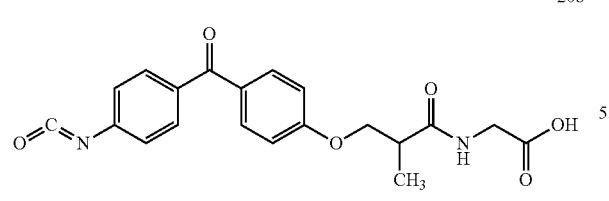
21a
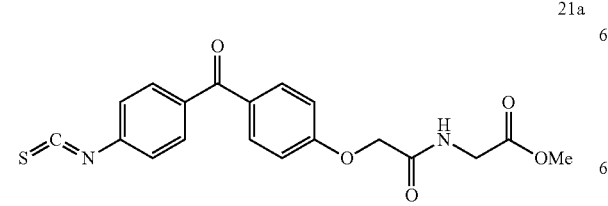
21b
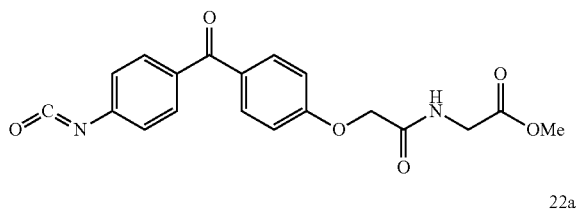
22a
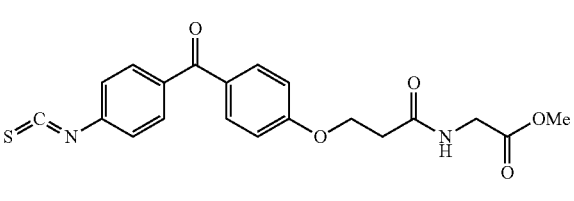
22b
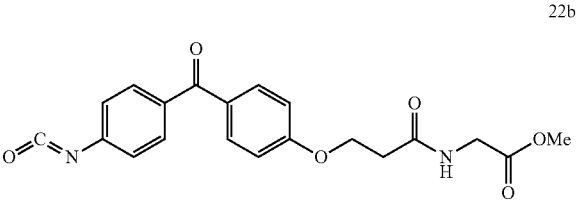
23a
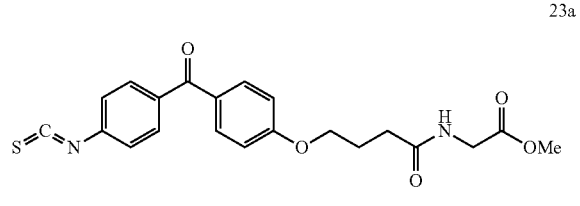
23b
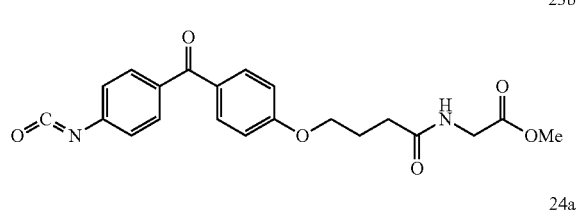
24a
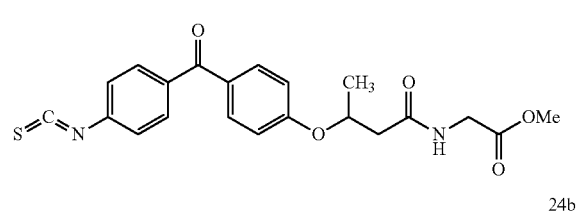
24b
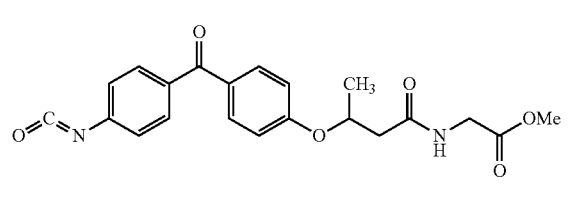
25a
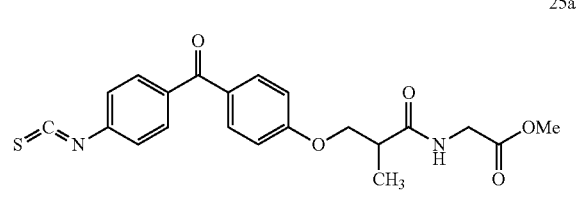

33b
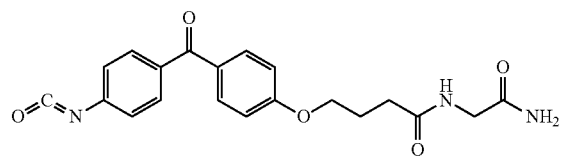
34a
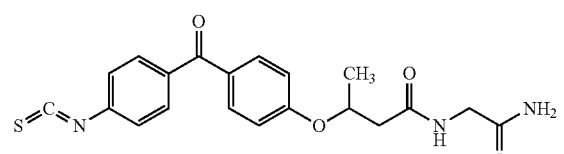
34b
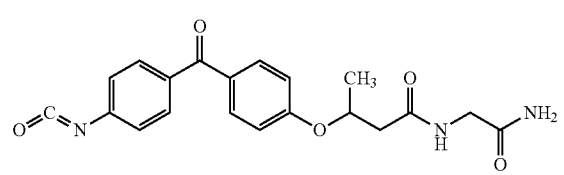
35a
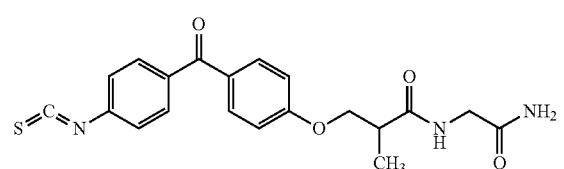
35b
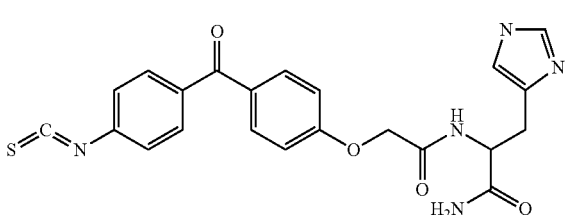
36a
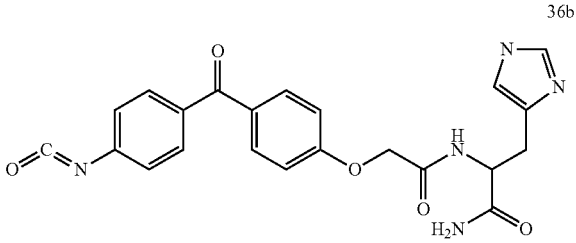
36b
37a
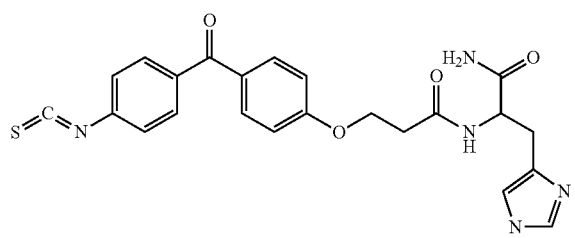
37b
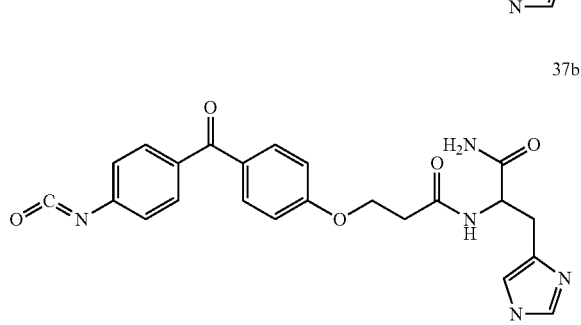
38a
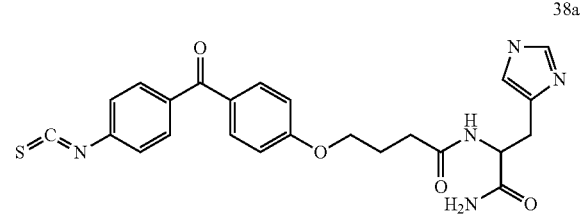
38b
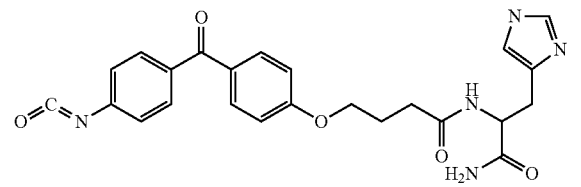
39a
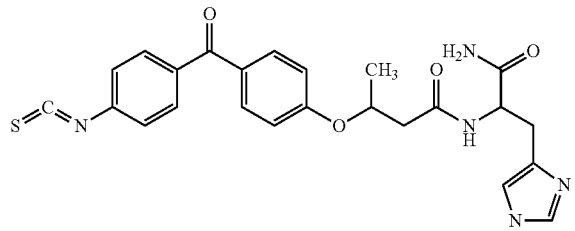
39b
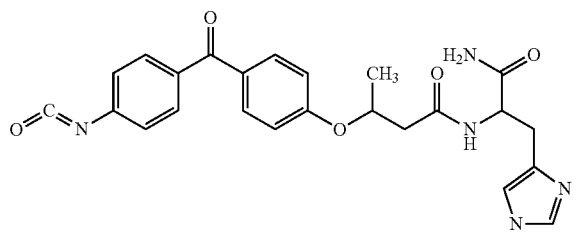

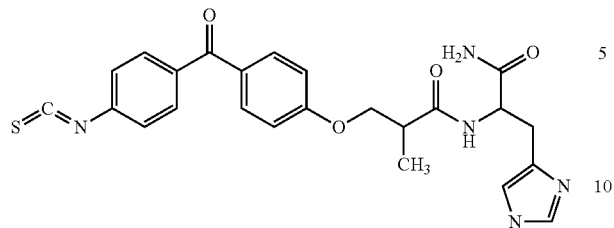
40a
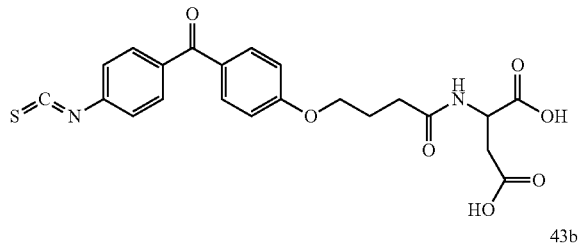
43a
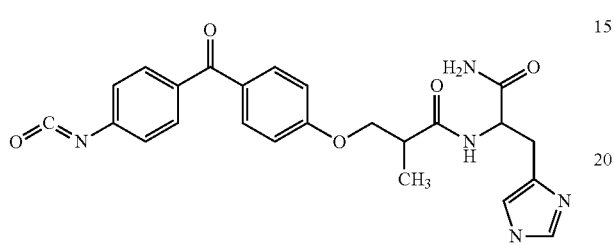
40b
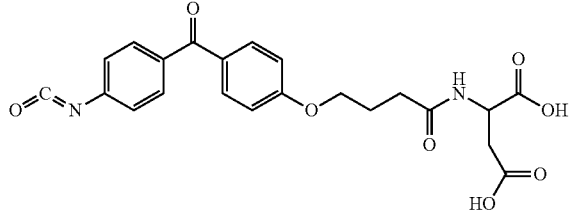
43b
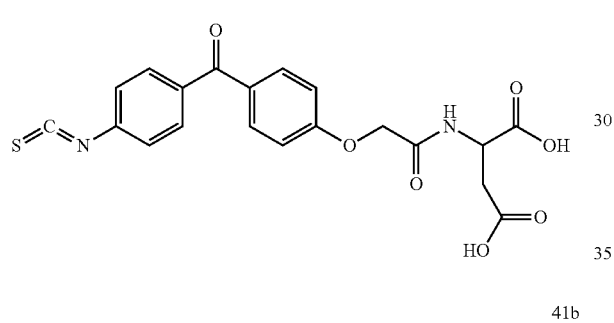
41a
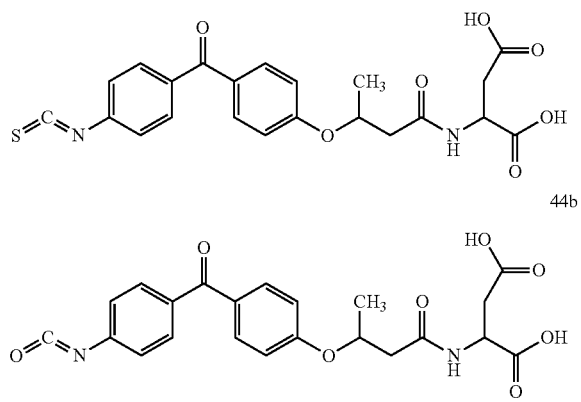
44a
44b
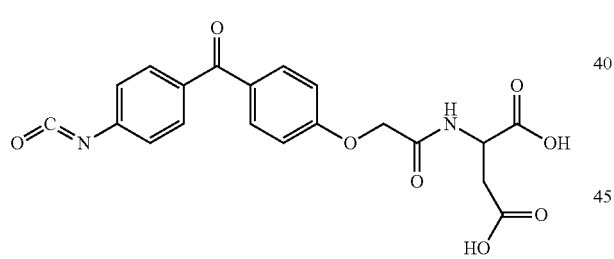
41b
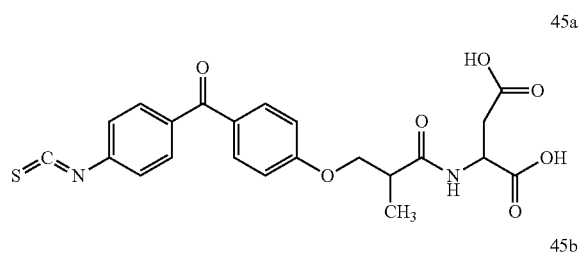
45a
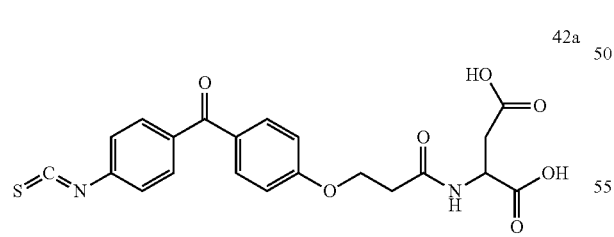
42a
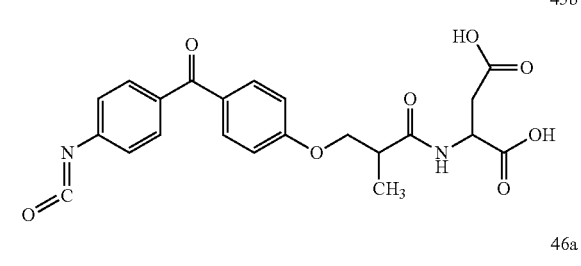
45b
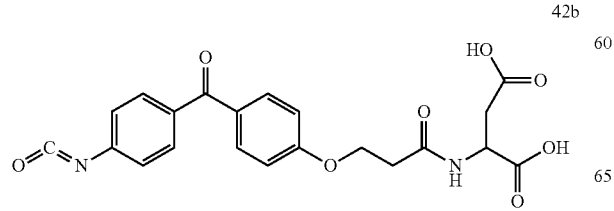
42b
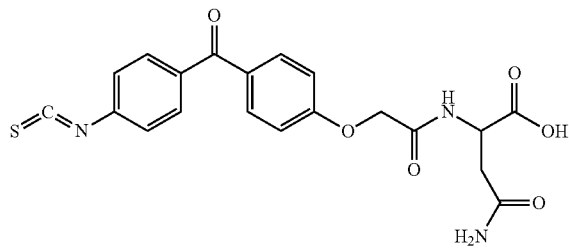
46a

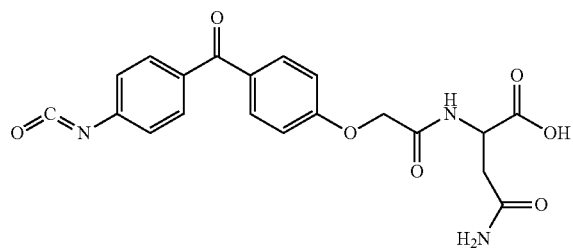
46b
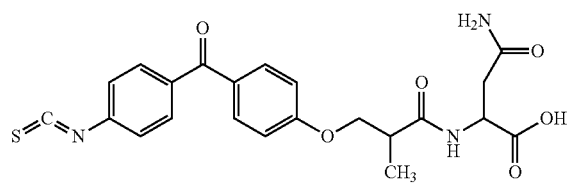
50a
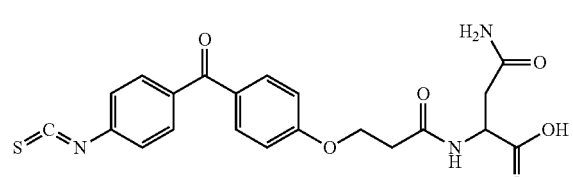
47a
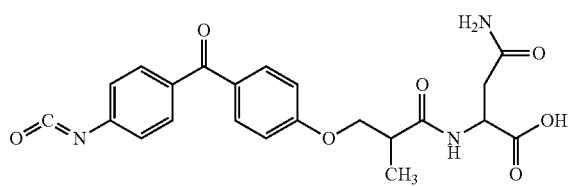
50b
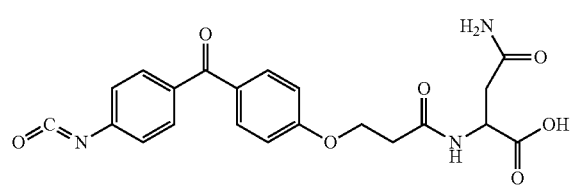
47b
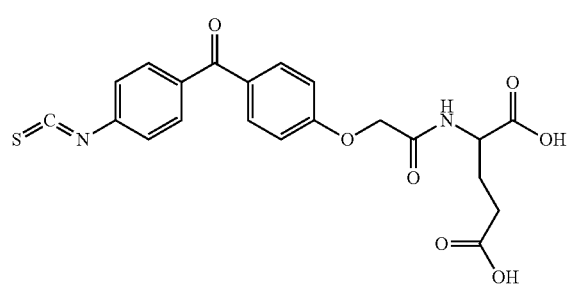
51a
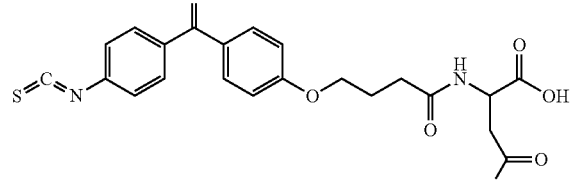
48a
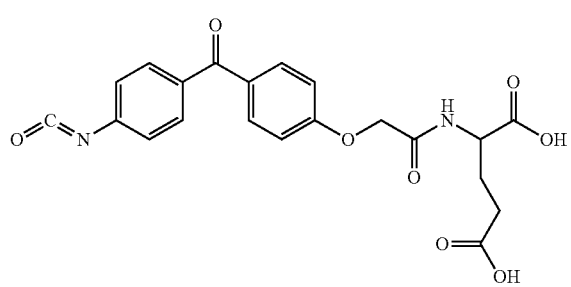
51b
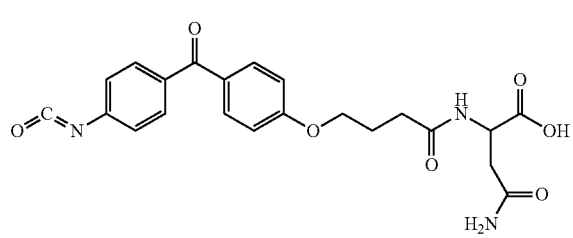
48b
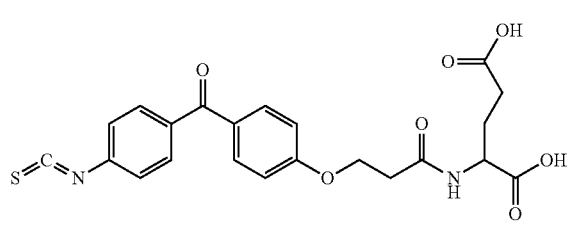
52a
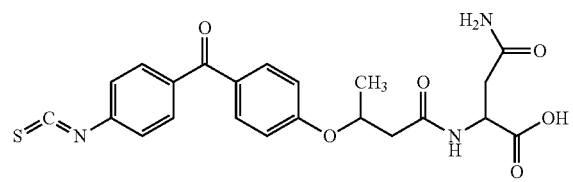
49a
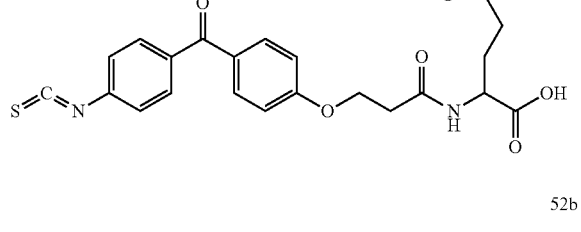
52b
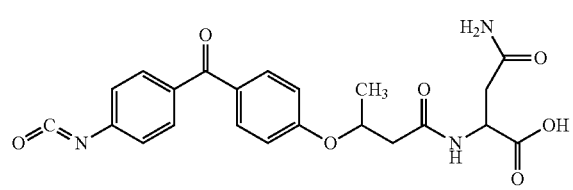
49b
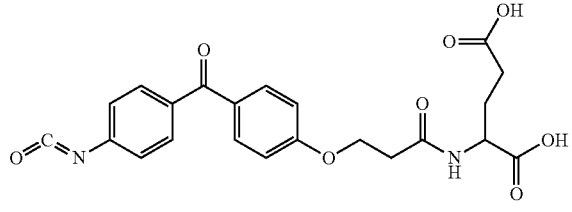

53a 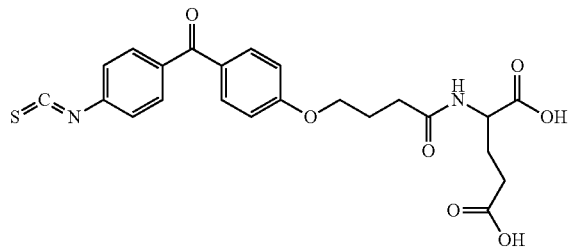
56a 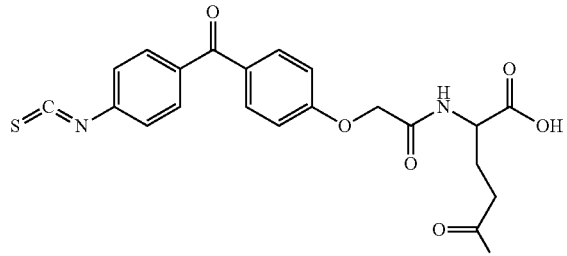
53b 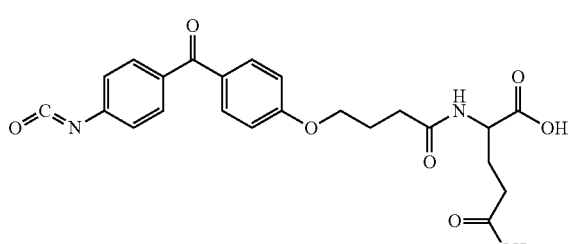
56b 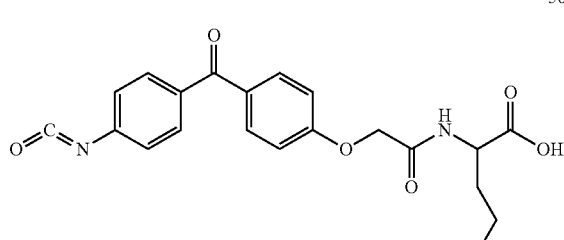
54a 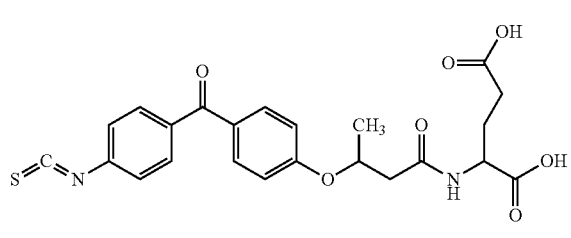
57a 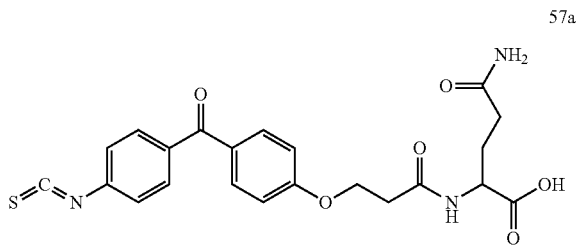
54b 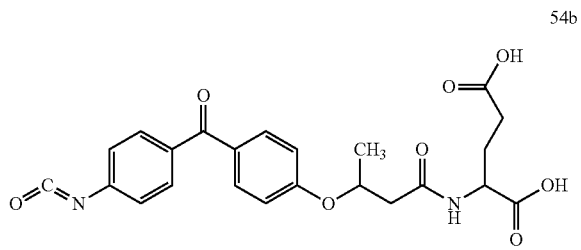
57b 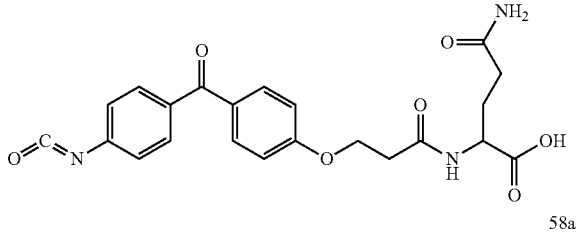
55a 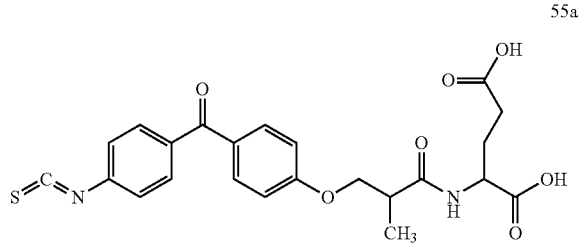
58a 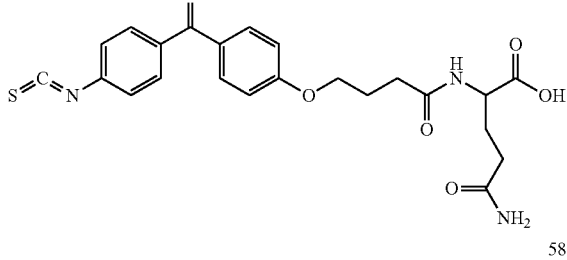
55b 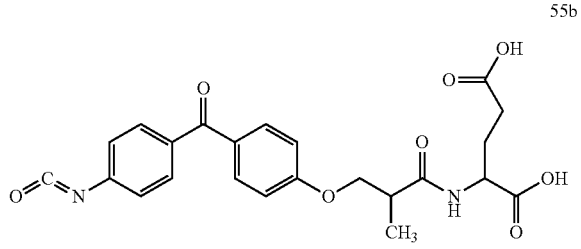
58b 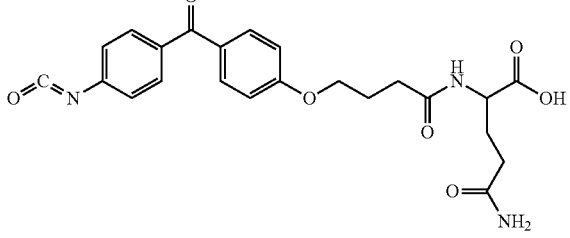

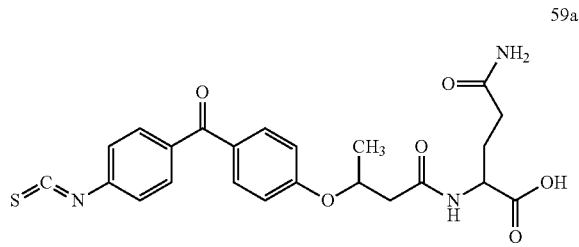
59a
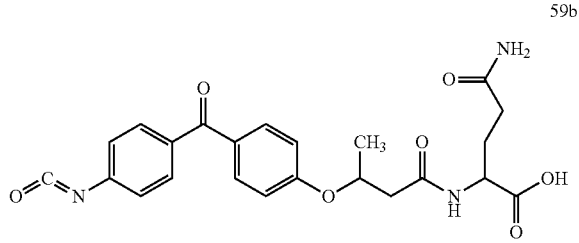
59b
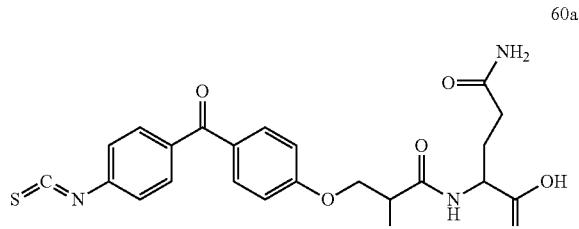
60a
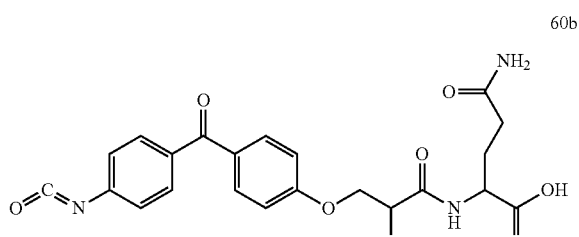
60b
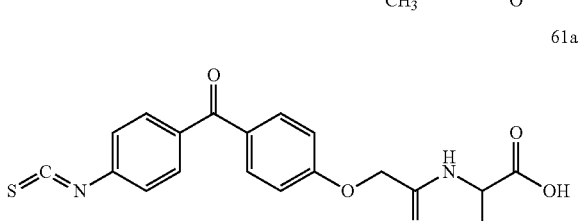
61a
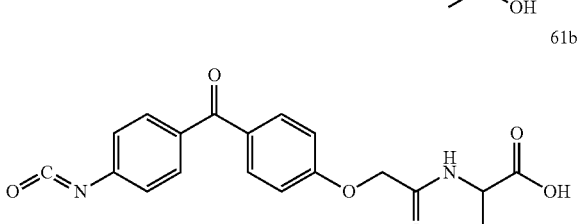
61b
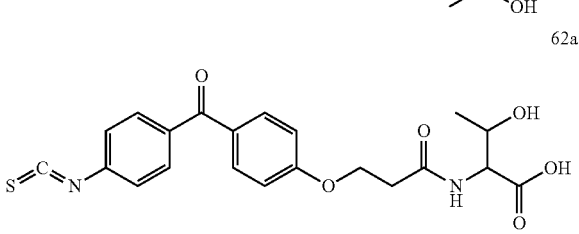
62a
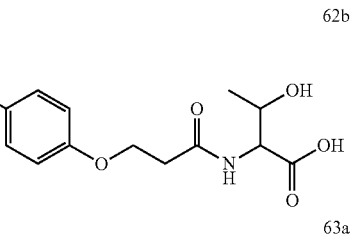
62b
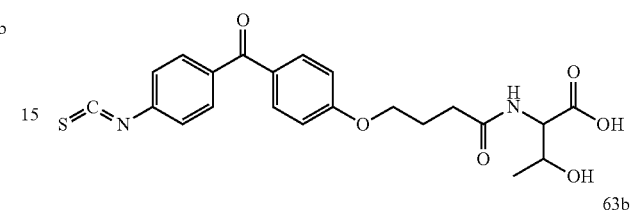
63a
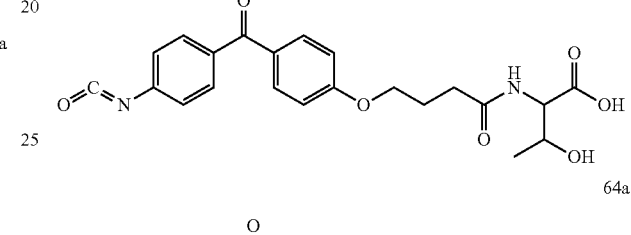
63b
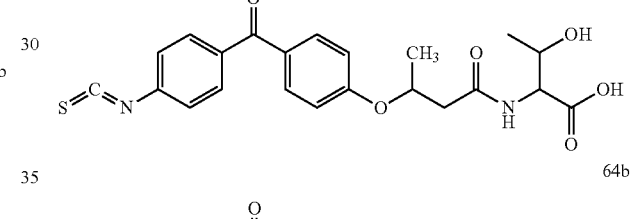
64a
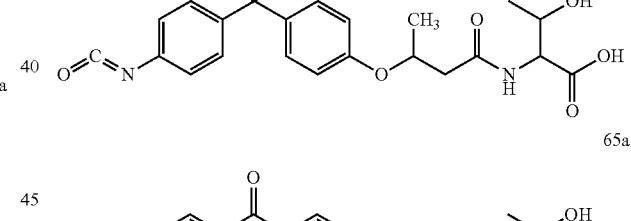
64b
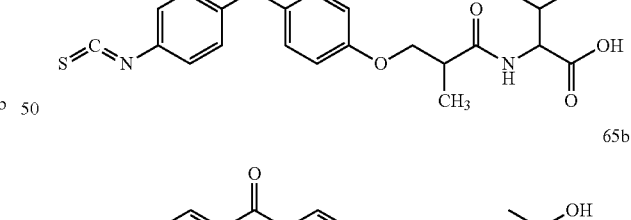
65a
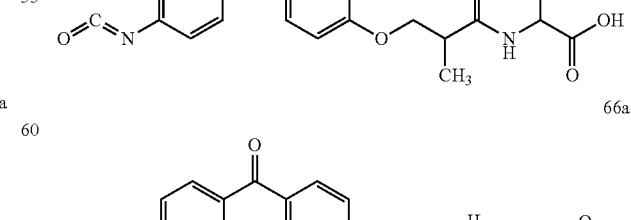
65b
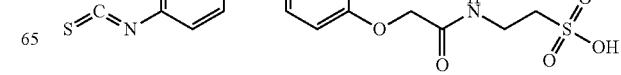
66a

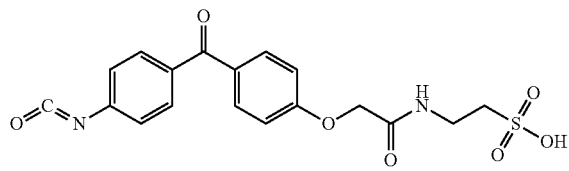
66b
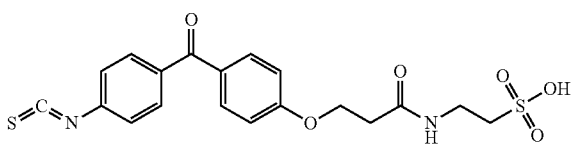
67a
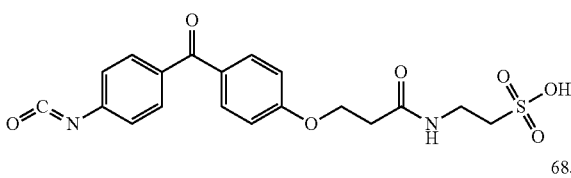
67b
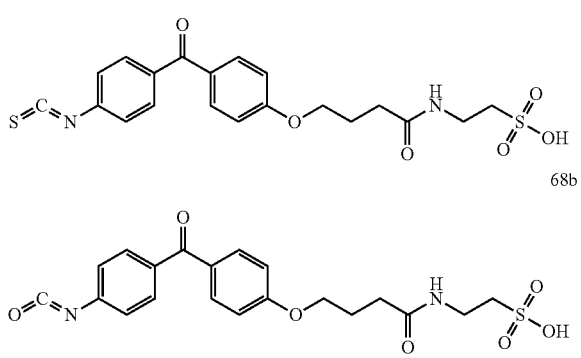
68a
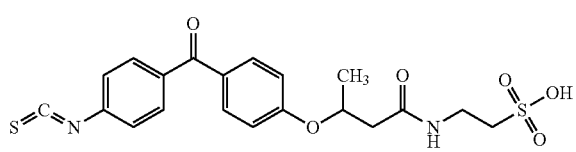
69a
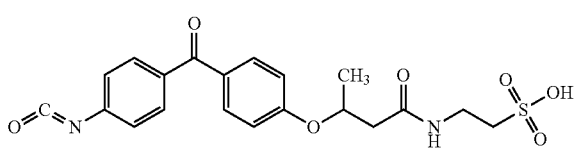
69b
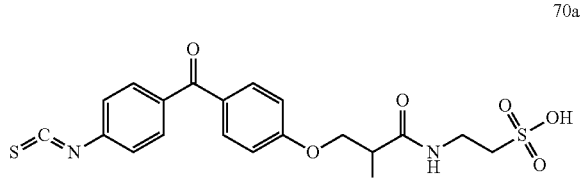
70a
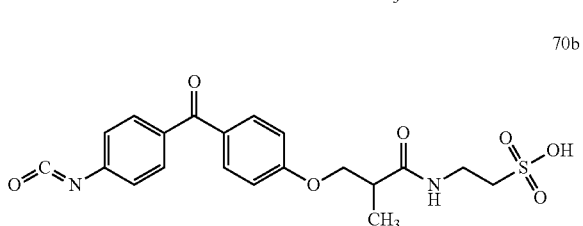
70b
or pharmaceutically acceptable salts of any of the foregoing.
* * * * *